(12) United States Patent
Yamauchi et al.

(10) Patent No.: US 6,355,669 B1
(45) Date of Patent: Mar. 12, 2002

(54) RETINOIC ACID AGONISTS AS PREVENTIVE AND THERAPEUTIC AGENTS FOR NEPHRITIS

(75) Inventors: Toshihiko Yamauchi; Akira Ishibashi; Naoki Tokuhara; Mitsuo Nagai, all of Tsukuba (JP)

(73) Assignee: Eisai Co., Ltd., Tokyo (JP)

(*) Notice: Subject to any disclaimer, the term of this patent is extended or adjusted under 35 U.S.C. 154(b) by 0 days.

(21) Appl. No.: 09/529,675

(22) PCT Filed: Sep. 22, 1998

(86) PCT No.: PCT/JP98/04266

§ 371 Date: Apr. 18, 2000

§ 102(e) Date: Apr. 18, 2000

(87) PCT Pub. No.: WO99/20309

PCT Pub. Date: Apr. 29, 1999

(30) Foreign Application Priority Data

Oct. 22, 1997 (JP) ............................................. 9-290073

(51) Int. Cl.⁷ ........................ A61K 31/40; A61K 31/34; C07D 405/00; C07D 307/78
(52) U.S. Cl. .................. 514/427; 514/429; 514/469; 548/517; 548/529; 549/469; 549/491
(58) Field of Search ................ 514/427, 429, 514/469; 548/517, 529; 549/469, 491

(56) References Cited

U.S. PATENT DOCUMENTS 5,081,271 A * 1/1992 Koichi et al. ................ 556/106
6,121,309 A   9/2000 Tagami et al. ............... 514/422

FOREIGN PATENT DOCUMENTS

| EP | 838453 | * | 4/1998 |
| EP | 889032 | * | 1/1999 |
| JP | 1-249783 |  | 10/1989 |
| WO | WO94/17796 |  | 8/1994 |
| WO | WO9702244 | * | 1/1997 |
| WO | 9702244 | * | 1/1997 |
| WO | WO97/24116 |  | 7/1997 |
| WO | 9315740 | * | 9/1997 |
| WO | 9734869 | * | 9/1997 |

OTHER PUBLICATIONS

Elder James T. et al.;"Retinoid induction of . . . human dermal . . . " J.Inv.Der.106/3, 517–21,Mar. 1996.*
Germuth, Immunopathology of the Renal Glomerulus pp 181–194.
Mangelsdorf The Retinoid Receptors 2nd ed. 1994, pp 319–349.
Brinckerhoff, Science 221, 756–758, 1983 Inflammation and Collagenase Production in Rats etc.
Racke J. Immunol. 154, 450–458 Retinoid Treatment of Experimental Allergic Encephalomyelitis.

Apfel Proc. Natl. Acad. Sci. 89 7129–7133 A retinoic acid Receptor α antagonist selectively etc.

Blomhoff J. Biol. Chem., 25 23988–23992, 1992 Vitamin A is a Key Regulator for Cell Growth etc.

Fahlman J. Immunol. 155 58–65, 1995 All–trans– and 9–cis–Retinoic Acid Inhibit Growth of Normal etc.

Kuwabara FEBS Letters 378 153–156, 1996 Novel Synthetic retinoic acid inhibits rat collagen etc.

Lomo J. Cell. Physiol. 175 68–77 1998 RAR–, not RXR, Ligands Inhibit Cell Activation and Prevent etc.

Buck J. Cell Biol. 115 851–859 1991 Differences in the Action and Metabolism between Retinol etc.

* cited by examiner

Primary Examiner—Richard L. Raymond
Assistant Examiner—Sudhaker B. Patel
(74) Attorney, Agent, or Firm—Nixon & Vanderhye

(57) ABSTRACT

The present invention provides a therapeutic or prophylactic agent as a substitute for conventional steroids or immunosuppressive agents to treat or prevent systemic erythematosus, glomerulonephritis, lupus nephritis, idiopathic thrombocytopenic purpura or autoimmune anemia. The agent comprises a retinoic acid receptor agonist, specifically a retinoic acid receptor subtype α (RARα) agonist, including for example:

(1) carboxylic acid compounds having condensed rings represented by the following formula:

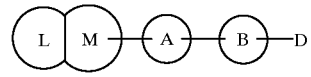

(wherein the rings L and M are condensed, are the same as or different from each other, and represent an aromatic hydrocarbon which may have a substituent group or a heterocycle which may have a substituent group; the rings A and B are independent of each other and represent an aromatic hydrocarbon ring or heterocycle which may have a substituent group; and D represents a carboxyl group which may have a protective group), (2) 4-{[(3,5-bistrimethylsilylphenyl)carbonyl]amino}benzoic acid, 4-{2-[5-(3-methoxymethyl-5,6,7,8-tetrahydro-5,5,8,8-tetramethylnaphthalene-2-yl)pyrrolyl]}benzoic acid, etc.

7 Claims, 3 Drawing Sheets

* p<0.05, One-way ANOVA test (Dunnett type multiple comparison)

* p<0.05, One-way ANOVA test (Dunnett type multiple comparison)

\* $p<0.05$, One-way ANOVA test (Dunnett type multiple comparison)

RETINOIC ACID AGONISTS AS PREVENTIVE AND THERAPEUTIC AGENTS FOR NEPHRITIS

This application is a 35 U.S.C. §371 of PCT/JP98/04266, filed Sep. 22, 1998.

FIELD OF THE INVENTION

The present invention relates to a therapeutic or prophylactic agent for glomerulonephritis, lupus nephritis, idiopathic thrombocytopenic purpura or autoimmune anemia, which comprises a retinoic acid receptor (RAR) agonist as an active ingredient. In particular, the present invention relates to a therapeutic or prophylactic agent for systemic erythematosus, glomerulonephritis, lupus nephritis, idiopathic thrombocytopenic purpura or autoimmune anemia, which comprises a retinoic acid receptor subtype α (RARα) agonist as an active ingredient.

PRIOR ART

1) Glomerulonephritis

Glomerulonephritis is generally called nephritis where continuous albuminuria and hematuria are clinically observed, and shows a morbid state in which renal functional disturbance and complications of edema, high blood pressure and cardiac insufficiency due to storage of sodium occur in some cases.

Pathogenically, glomerulonephritis can be defined as a glomerular disease showing an increase in mesangium (phonetic transcription) cells and/or substrate in renal glomeruli.

The most universal idea on the mechanism of the onset of glomerulonephritis is that immune reaction products occurring on glomeruli damage the glomeruli. It is also evident from the fact that the damage is caused by heteroantibody and host antibody in an animal experiment. Masugi experimentally created glomerulonephritis by intravenously administering duck-derived nephrotoxic serum against rabbit renal tissues into normal domestic rabbits, and domestic rabbit-derived nephrotoxic serum against rat renal tissues into rats, thus demonstrating that glomerulonephritis is generated by an immunological mechanism (Masugi, M., Beitr. Pathol. Anat., 91, 82–112, 1933, Masugi, M., Beitr. Pathol. Anat., 92, 429–466, 1934). Since fluorescent antibody techniques were introduced for renal materials in biopsy in the 1960's, there have been reported a large number of data suggesting that an immunological mechanism is involved in generating glomerulonephritis in humans as well. In nephritis caused by these immune reactions, sedimentation of an antigen-antibody immune complex (IC) onto glomeruli is particularly important.

From the previous results of studies on animal experiment models, nephritis caused by precipitation of IC in circulating blood and nephritis by formation of IC in situ are being considered. The former is nephritis caused by binding a protein antigen originally unrelated to glomerular tissues to its corresponding antibody in blood, to form IC which is then precipitated on a glomerular sling wall or on mesangium. The latter includes 2 types of nephritis: one is caused by IC formed by binding an antibody against a renal tissue antigen (unique component in glomerular basement membrane and glomerular cells) directly to glomeruli, and the other is caused by IC formed by precipitation of an extraneous antigen via electrical charge or other affinity on glomeruli and subsequent binding of its corresponding antibody to the glomeruli in situ. The site on which IC is precipitated includes mesangium observed in endothelial cells and IgA nephropathy, in addition to epithelial cells observed in human nephropathy originating in membrane. The factors determining the precipitation site include the size of immune complex, the electric charge of antigen, antibody and immune complex, the binding force between antigen and antibody, and type and subclass of antibody. These factors are involved in precipitating an immune complex in blood or forming an immune complex in situ followed by activation of complements to initiate inflammation reaction.

Major therapeutic agents used at present for glomerulus nephritis include anti-platelet agents, anti-coagulating agents, adrenocortical steroids and immunosuppressive agents. Among these, as described above, the immunological mechanism is involved considerably in the onset of nephritis so that conventional therapy for nephritis is based on adrenocortical steroids inhibiting immune response.

The nephrosis syndrome is a disease to which adrenocorticotrophic steroids are most suited. However, the glomerulus nephritis as a causative disease for the nephrosis syndrome has various types ranging from the primary to secondary one, thus revealing that thereactivity of steroids to the nephritis syndrome is varied depending on the type of nephritis. For example, the complete remission of minimal change nephrotic syndrome (MCNS) is achieved in 80 to 95% cases by steroids. However, the effect of therapy with steroid is hardly expected except for only the case of IgA nephropathy where the degree of albuminuria is moderate while renal function is maintained, and in only this case, the therapy with steroid is performed. About ⅔ of patients with acute nest-like glomerular sclerosis respond to steroids, but the other ⅓ patients are resistant to steroids and advance to terminal-stage renal insufficiency, and patients with chronic glomerular sclerosis are also hardly responsive to steroids. Although a reduction in albuminuria in nephropathy originating in membrane (glomerulonephritis originating in membrane) is recognized by use of steroids for aprolonged period of time, stringent evaluation of this therapy is still not be established. Further, secondary lupus nephritis is classified into I to IV types in renal biopsy, and the clinical effect of the steroids thereon is varied; the effect on the IV type (diffuse proliferation type) cannot be expected even by administering in a large amount, rather there is the possibility of aggravation.

An immunosuppressive agent is used in combination when therapy using only adrenocortical steroid is insufficient in the case of steroid-resistant and frequently relapsing nephrosis syndrome, rapidly progressive glomerulonephritis or lupus nephritis, or for the purpose of reducing the dose of the adrenocortical steroid. Generally used agents include cyclophosphamide, cyclosporin A and mizoribine. Cyclophosphamide is used frequently, but there occur various side effects depending on the dose. Major side effects include bone marrow inhibition, hepatic damage, alopecia, lung fibrosis, bleeding cystitis and hypofunction of sexual glands. Cyclosporin A shows an immunosuppressive action on T cells, but it has severe side effects include renal damage, hepatic damage, central nerve damage, infections and acute pancreatitis, among which the renal damage occurs depending on the blood concentration, thus making it necessary to monitor the blood concentration. Mizoribine has less side effects than other immunosuppressive agents, but is poor in effect on the diseases.

As described above, there are a large number of cases where the effects of the adrenocortical steroids used as the first choice in conventional therapy are not satisfactory, while the immunosuppressive agents used for compensating therefor have the problem of side effects.

2) Autoimmune Diseases in which Autoantibody is Involved

The autoantibody observed in autoimmune diseases is roughly divided into 2 groups depending on the characteristic distribution of its corresponding antigen in the body. The first group is an organ-specific autoantibody observed in organ-specific autoimmune diseases. This kind of autoantibody corresponds to anti-thyroid-stimulating hormone receptor antibody detected in patients with Basedow's disease, or to an anti-acetyl choline receptor antibody detected in patients with severe myasthenia. The second group is the one which reacts with antigen present in almost all organs in the body or in serum, and is called organ-unspecific autoantibody. The characteristic autoantibody in systematic autoimmune diseases such as glycogen storage disease is included in this group. These autoimmune antibodies directly damage organs or form an immune complex thereby generating the morbid state of autoimmune diseases. Further, even in autoimmune diseases wherein the relationship between the presence of autoantibody and the morbid state is not clear, the detection of autoantibody is revealed to be clinically important as being indicative of diagnosis, activity of the diseases, and judgement of therapeutic effect. Hereinafter, some typical autoimmune diseases in which autoantibody is involved are described.

Systemic lupus erythematosus (SLE) shows various symptoms, and symptoms and examination views adopted as classification criteria includes the following 11 items: 1) cheek erythema, 2) disk-shaped erythema, 3) hypersensitivity to light, 4) ulcer in the oral cavity, 5) arthritis, 6) serositis, 7) renal damage, 8) nerve damage, 9) blood abnormality, 10) immune abnormality, and 11) antinuclear antibody. These symptoms and abnormalities in examination are considered due to autoantibody. It is estimated that antinuclear antibody as typical autoantibody forms an immune complex and causes disturbance such as lupus nephritis via the III type allergy mechanism. Lupus nephritis is observed in 60% of patients with systematic erythematosus, and for the treatment, adrenocortical steroids are used. However, in the case of steroid-resistant lupus nephritis or when there occur severe side effects of steroids, administration of an immunosuppressive agent is taken into consideration. An immunosuppressive agent used frequently is azathiopurine or cyclophosphamide.

Idiopathic thrombocytopenic purpura (ITP) is a disease in which autoantibody against platelets is produced to destroy platelets. Clinical symptoms include the tendency of bleeding caused by a reduction in platelets, and bleeding occurs mainly under the skin and on the mucosa to cause purpura, petechia and blood spot. When platelets are significantly reduced, there occur complications of oral bleeding, nasal bleeding, genital bleeding, bloody excrements, retinal hemorrhage etc., and the most severe case, the complications are accompanied by cranial hemorrhage. For general treatment of ITP, an adrenocortical steroid is used as a first choice, followed by conducting pancreatectomy. However, there are not few cases showing resistance to this standard treatment, and in these cases, treatment by administration of an immunosuppressive agent or danazole is attempted, but the effectiveness is not so high.

In autoimmune hemolytic anemia, antibody against self-erythrocytes is produced to cause hemolysis, and anemia and jaundice are clinically observed. Treatment is based on administration of steroids, and an immunosuppressive agent is also used if response is poor, or to reduce maintenance dose of steroids. However, it was recognized that about ¼ of the patients are worsened during maintenance therapy.

In Basedow's disease, autoantibody against thyroid-stimulating hormone receptors stimulates the thyroid to cause hyperthyroidism. As clinical symptoms, diffuse struma, tachycardia, tremor of fingers are observed. For treatment, the inhibition of formation of the hormone by administering an anti-thyroid drug such as thiamazole or propyl thiouracil, by destruction of the thyroid gland with radioactive iodine, or by subtotal resection of the thyroid gland by operation is performed, but there is no established therapeutic method against the causative factor of the disease.

Accordingly, the object of the present invention is to provide a therapeutic or prophylactic agent as a substitute for conventional steroids or immunosuppressive agents to treat systemic erythematosus, glomerulonephritis, lupus nephritis, idiopathic thrombocytopenic purpura or autoimmune anemia.

Retinoic acid plays an important role for growth of animal and in maintaining functions, such as specific regulation of differentiation and proliferation of cells and morphological formation of vertebrates. In connection with these physiological actions, retinoic acid attracts attention as an anti-cancer agent or as a specific remedy for proliferated skin diseases (psoriasis and keratosis), and a number of retinoic acid analogues have been synthesized. In recent years, the presence of $\alpha$, $\beta$ and $\gamma$ subtypes of retinoic acid receptor was revealed (The Retinoids, 2nd ed., Raven Press, Ltd., New York, 1994, Sporn, M. B., Roberts, A. B., Goodman, D. S.). However, the physiological importance of each receptor has not been revealed yet.

On the other hand, the intimate involvement of vitamin A in the immune system has been known from of old. There are many reports in which retinoic acid as a product of metabolism of vitamin A acts for inhibition of the immune system. For example, Brinckerhoff et al. have reported that secondary inflammations in rat adjuvant arthritis as a model with human rheumatic arthritis are significantly suppressed by administering 13-cis-retinoic acid (Brinckerhoff, C. E., et al., Science 221, 756, 1983). Further, Racke et al. have reported that neural symptoms of mouse allergic cerebrospinal meningitis as a model with human multiple sclerosis is ameliorated by administering retinoids such as 13-cis-retinoic acid and 4-hydroxyretinamide (Racke, M. K., et al., J. Immunol., 154, 450–458, 1995). It is suggested that in these models, retinoids ameliorate the morbid state by inhibiting the activation of T-lymphocytes.

In addition, it is also reported that retinoids inhibit the activation of B lymphocytes. That is, it is reported that all-trans-retinoic acid inhibits polyclonal division of mouse B lymphocytes or human B lymphocytes (Apfel, C., Proc. Natl. Acad. Sci. USA, 89, 7129–7133, 1992, Blomhoff, H. K., et al., J. Biol. Chem., 25, 23988–23992, 1992 and Fahlman, C., et al., J. Immunol., 155, 58–65, 1995). Further, it is reported that Am80 which is a retinoic acid receptor subtype $\alpha$ (RAR$\alpha$) agonist strongly inhibited production of anti-collagen antibody titer in blood in a rat model with collagen arthritis (Kuwabara, K., et al., FEBS Letters, 378, 153–156, 1996).

It is shown that retinoids act on B lymphocyte via retinoic acid receptor (RAR) (Blomhoff, H. K., et al., J. Cell. Physiol., 175, 68–77, 1998). Further, it is suggested that RAR$\alpha$ has an important role in demonstrating the actions described above, from the following findings: (1) among RAR subtypes, RAR$\alpha$ and RAR$\gamma$ are expressed in human B lymphocytes, and in particular RAR$\alpha$ is strongly expressed, while RAR$\beta$ is not expressed (Blomhoff, H. K., et al. 1998, supra, and Buck, J. L., et al., J. Cell. Biol., 115, 851–859, 1991) and (2) the inhibitory action of retinoic acid on differentiation of mouse B lymphocytes was recovered almost perfectly by adding RARα antagonist (Ro 41-5253) (Apfel, C., 1992, supra).

As described above, retinoids inhibit the activation of B lymphocytes in addition to T lymphocytes, and this effect is suggested to be via RARα in particular among the RAR subtypes. However, even the reports mentioned above do not contain any description indicating a clear relationship between RAR or RARα and production of antibody by B lymphocytes.

WO94/17796, U.S. Pat. No. 4,703,110, JP-A 2-76862, JP-A 63-255277, JP-A 8-505359, WO97/24116 etc. disclose the use of retinoid-like active compounds for treating a wide variety of inflammatory, allergic and rheumatic immune diseases including cancers such as leukemia, breast cancer, prostate cancer, lung cancer, esophagus and respiratory tract cancer, skin cancer and bladder cancer; skin diseases such as psoriasis, keratosis, eczema, atopic dermatitis, acne and Darier's disease; autoimmune diseases such as chronic articular rheumatism and erythematosus; chronic polyarthritis, spinal arthritis and deformable arthritis. However, these publications neither suggest a therapeutic method against specific causative factors, for example by utilizing the inhibitory action of RAR agonist on production of autoantibody to treat autoimmune diseases in which the autoantibody is involved, nor contain any description of glomerulonephritis, lupus nephritis, idiopathic thrombocytopenic purpura and autoimmune anemia. However, in only WO97/34869 there appears a description of glomerulonephritis, but there is no disclosure on specific data suggesting or clearly showing the effect, nor is there a description of lupus nephritis, idiopathic thrombocytopenic purpura and autoimmune anemia. Further, there is none of the description that among RAR agonists, subtype α-agonist contributes particularly to prevention and treatment of systematic erythematosus and glomerulus nephritis.

DISCLOSURE OF THE INVENTION

The present inventors extensively studied retinoid compounds and found that RAR agonists have potent inhibitory action on production of antibody. On the basis of this finding, they further continued the study to find that among a plurality of subtype receptors, particularly RARα agonist acting on α-receptor is a major agonist contributing to the inhibitory action, thus completing the present invention.

The present invention relates to a therapeutic or prophylactic agent for a disease against which the inhibitory action of a retinoic acid receptor (RAR) agonist or a pharmacologically acceptable salt thereof as an active ingredient on production of antibody is effective. Further, the present invention relates to use of a retinoic acid receptor (RAR) agonist or a pharmacologically acceptable salt thereof for producing a therapeutic or prophylactic agent for a disease against which the inhibitory action thereof on production of antibody is effective.

That is, the present invention relates to a therapeutic or prophylactic agent for systematic erythematosus, glomerulonephritis, lupus nephritis, idiopathic thrombocytopenic purpura or autoimmune anemia, wherein a retinoic acid receptor (RAR) agonist, particularly an RARα agonist or a pharmacologically acceptable salt thereof, comprising compounds shown (1) to (12) below, is used as an active ingredient.

1) carboxylic acid compounds having condensed rings represented by the formula (I):

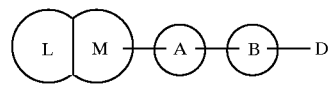

wherein the rings L and M are condensed, are the same as or different from each other and represent an aromatic hydrocarbon which may have a substituent group or a heterocycle which may have a substituent group, the rings A and B are independent of each other and represent an aromatic hydrocarbon ring or heterocycle which may have a substituent group, and D is a carboxyl group which may have a protective group, 2) carboxylic acid compounds having heterocycle disclosed in JP-A 9-71566, which are represented by the formula (II):

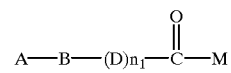

wherein A represents the following groups:

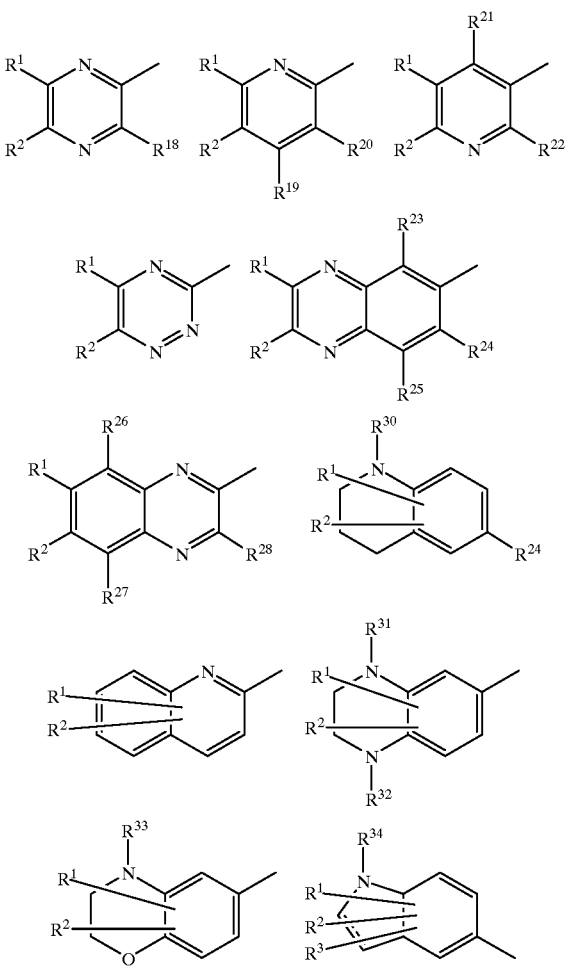

-continued

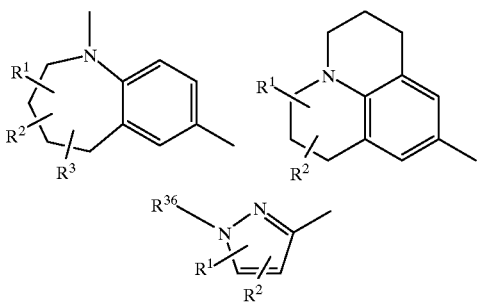

(wherein R¹ to R³, R¹⁸ to R²⁸ and R³⁰ to R³⁶ are the same as or different from and represent hydrogen atom, a halogen atom, a lower alkyl group or a phenyl group which may have a substituent group, and the formula ═══ represents a single or double bond), B represents a heteroarylene group which may have a substituent group, an arylene group which may have a substituent group, the group represented by the formula —CONH— or the group represented by the formula —CR⁶═CR⁷— (wherein R⁶ and R⁷ are the same as or different from each other and represent hydrogen atom, a lower alkyl group or a halogen atom), D represents an arylene group which may have a substituent group, a heteroarylene group which may have a substituent group or the group represented by the formula —CR⁶═CR⁷ (wherein R⁶ and R⁷ have the same meanings as defined above), n₁ is 0 or 1, and M represents hydroxyl group, a lower alkoxy group or the group represented by the formula —NR¹⁶R¹⁷ (wherein R¹⁶ and R¹⁷ are the same as or different from each other and represent hydrogen atom, hydroxyl group, a lower alkyl group, a hydroxyalkyl group, an aryl group or a heteroaryl group, or R¹⁶ and R¹⁷ may, together with a nitrogen atom to which they are bound, form a ring optionally containing an oxygen or sulfur atom, 3) 4-{2-[5-(5,6,7,8-tetrahydro-5,5,8,8-tetramethylnaphthalene-2-yl)pyrrolyl]}benzoic acid, 4-{2-[5-(5,6,7,8-tetrahydro-5,5,8,8-tetramethylnaphthalene-2-yl)franyl]}benzoic acid, 4-{2-[5-(5,6,7,8-tetrahydro-5,5,8,8-tetramethylnaphthalene-2-yl)thiophenyl]}benzoic acid or 4-{2-[5-(5,6,7,8-tetrahydro-5,5,8,8-tetramethylnaphthalene-2-yl)pyrazolyl]}benzoic acid disclosed in JP-A 2-240058, 4) 4-[2-(3,4-dihydro-2H-1-benzopyran-6 or 7-yl)propenyl]benzoic acid compounds, 4-[2-(3,4-dihydro-2H-1-benzothiopyran-6 or 7-yl)propenyl]benzoic acid compounds, 4-[2-(1,2,3,4-tetrahydroquinoline-6 or 7-yl)propenyl]benzoic acid compounds, 4-{[(3,4-dihydro-2H-1-benzopyran-6 or 7-yl)carbonyl]amino}benzoic acid compounds, 4-{[(3,4-dihydro-2H-1-benzothiopyran-6 or 7-yl)carbonyl]amino}benzoic acid compounds or 4-{[(1,2,3,4-tetrahydroquinoline-6 or 7-yl)carbonyl]amino}benzoic acid compounds disclosed in JP-A 2-76862, 5) 4-(trimethylsilyl-substituted phenyl)benzoic acid compounds disclosed in JP-A 1-249783, 6) [(3,4-dihydro-2H-1-benzopyran-6-yl)ethynyl]heteroaryl carboxylic acid compounds, [(3,4-dihydro-2H-1-benzothiopyran-6-yl)ethynyl]heteroaryl carboxylic acid compounds or [(1,2,3,4-tetrahydroquinoline-6-yl)ethynyl]heteroaryl carboxylic acid compounds disclosed in JP-A 63-255277, 7) (E)-[2-(5,6,7,8-tetrahydro-5,5,8,8-tetramethyl-2-naphthyl)propenyl]phenol compounds disclosed in JP-A 62-267245, 8) 4-{[(5,6,7,8-tetrahydro-5,5,8,8-tetramethyl-2-naphthyl)carbonyl]amino}benzoic acid compounds disclosed in JP-A 61-22047, 9) 9-(substituted phenyl)-3,7-dimethyl-nona-2,4,6,8-tetraene-1-one acid compounds disclosed in JP-A 49-126637, 10) all-trans-retinoic acid, 11) 4-{2-[5-(5,6,7,8-tetrahydro-3,5,5,8,8-pentamethylnaphthalene-2-yl)pyrrolyl]}benzoic acid or 4-{2-[5-(3-methoxymethyl-5,6,7,8-tetrahydro-5,5,8,8-tetramethylnaphthalene-2-yl)pyrrolyl]}benzoic acid, and 12) 4-{[(5,6,7,8-tetrahydro-5,5,8,8-tetramethylnaphthalene-2-yl)carbonyl]amino}benzoic acid compounds, 4-{[(2,2,4,4-tetramethylchroman-2-yl)carbonyl]amino}benzoic acid compounds or 4-{[(2,6-di-t-butylpyrido-4-yl)carbonyl]amino}benzoic acid compounds disclosed in WO97/24116.

In the present invention, preferable compounds include: all-trans-retinoic acid; 4-{[(3,5-bistrimethylsilylphenyl)carbonyl]amino}benzoic acid compounds disclosed in JP-A 1-249783; 4-{[(5,6,7,8-tetrahydro-5,5,8,8-tetramethyl-2-naphthyl)carbonyl]amino}benzoic acid or 4-{[(5,6,7,8-tetrahydro-5,5,8,8-tetramethyl-2-naphthyl)amino]carbonyl}benzoic acid disclosed in JP-A 61-22047; and the compound group represented by the following general formula:

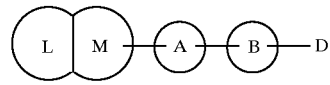

wherein L, M, A, B and D have the same meanings as defined above,

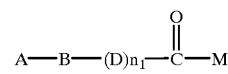

wherein A, B, D, M and n₁ have the same meanings as defined above.

More preferable compounds are the compound group shown in (1) to (20) below:

(1) 4-{2-[5-(5,8-dimethylnaphthalene-2-yl)pyrrolyl]}benzoic acid, (2) 4-{2-[5-(8-methylnaphthalene-2-yl)pyrrolyl]}benzoic acid, (3) 4-{2-[5-(8-ethylnaphthalene-2-yl)pyrrolyl]}benzoic acid, (4) 4-{2-[5-(8-isopropylnaphthalene-2-yl)pyrrolyl]}benzoic acid, (5) 4-{2-[5-(8-isopropenylnaphthalene-2-yl)pyrrolyl]}benzoic acid, (6) 4-{2-[5-(8-penylnaphthalene-2-yl)pyrrolyl]}benzoic acid, (7) 4-{2-[5-(4,7-dimethylbenzofuran-2-yl)pyrrolyl]}benzoic acid, (8) 4-{2-[5-(4,7-dichlorobenzofuran-2-yl)pyrrolyl]}benzoic acid, (9) 4-{2-[5-(5-chloro-7-ethylbenzofuran-2-yl)pyrrolyl]}benzoic acid, (10) 4-{2-[5-(4,7-dimethylbenzothiophene-2-yl)pyrrolyl]}benzoic acid, (11) 4-{2-[5-(3-fluoro-4,7-dimethylbenzofuran-2-yl)pyrrolyl]}benzoic acid, (12) 4-{2-[5-(7-ethyl-4-methylbenzofuran-2-yl)pyrrolyl]}benzoic acid, (13) 4-{2-[5-(7-fluoro-4-trifluoromethylbenzofuran-2-yl)pyrrolyl]}benzoic acid, (14) 4-{2-{5-[3-(1-ethyl-5-isopropylpyrazolyl)]pyrrolyl}}benzoic acid, (15) 4-{2-{5-[7-(1,5-dimethyl-2,3,4,5-tetrahydro-1H-benzazepinyl}pyrrolyl}benzoic acid, (16) 4-{4-{2-[2-(5,6,7,8-tetrahydro-5,5,8,8-tetramethylquinoxalynyl)]furyl}}benzoic acid, (17) 4-{2-{5-[2-(8,8-dimethyl-5,6,7,8-tetrahydroquinoxalynyl)]pyrrolyl}}benzoic acid, (18)

4-{[(5,6,7,8-tetrahydro-5,5,8,8-tetramethyl-2-naphthalenyl)amino]carbonyl}benzoic acid, (19) 4-{[(3,5-bistrimethylsilylphenyl)carbonyl]amino}benzoic acid and (20) 4-{2-[5-(3-methoxymethyl-5,6,7,8-tetrahydro-5,5,8,8-tetramethylnaphthalene-2-yl)pyrrolyl]}benzoic acid.

In the present invention, the term "may have a substituent group" means that the group may be substituted by the group selected from hydroxyl group; thiol group; nitro group; cyano group; halogen atom such as fluorine atom, chlorine atom, bromine atom and iodine atom; lower alkyl group such as methyl, ethyl, n-propyl and isopropyl; lower alkoxy group such as methoxy, ethoxy, n-propoxy, isopropoxy and butoxy group; halogenated alkyl group such as fluoromethyl group, difluoromethyl group, trifluoromethyl group and 2,2,2-trifluoroethyl group; alkylthio group such as methylthio group, ethylthio group and isopropylthio group; acyl group such as acetyl group, propionyl group and benzoyl group; hydroxyalkyl group such as hydroxymethyl group, hydroxyethyl group and hydroxypropyl group; amino group; monoalkyl amino group such as methyl amino group, ethyl amino group and isopropyl amino group; dialkyl amino group such as dimethyl amino group and diethyl amino group; carboxyl group; alkoxy carbonyl group such as methoxy carbonyl group, ethoxy carbonyl group and propyl carbonyl group; carbamoyl group; alkyl carbamoyl group such as methyl carbamoyl group and dimethyl carbamoyl group; acyl amino group such as acetyl amino group and benzoyl amino group; alkyl sulfonyl group such as sulfamoyl group, methyl sulfonyl group and ethyl sulfonyl group; unsubstituted or substituted aryl sulfonyl group such as benzene sulfonyl group and p-toluene sulfonyl group; unsubstituted or substituted aryl group such as phenyl group, tolyl group and anisolyl group; unsubstituted or substituted heteroaryl group such as pyrrole group, pyrazolyl group, imidazolyl group, triazolyl group, tetrazolyl group, thiazolyl group, pyridyl group, pyrimidyl group and pyrazinyl group; carboxy alkyl group; alkyloxycarbonyl alkyl group such as methoxycarbonyl methyl group, ethoxycarbonyl methyl group and methoxycarbonyl ethyl group; carboxyalkoxy group such as carboxymethoxy group; aryl alkyl group such as benzyl group and 4-chlorobenzyl group; heteroaryl alkyl group such as pyridyl methyl group and pyridyl ethyl group; and alkylene dioxy group such as methylene dioxy group and ethylene dioxy group.

The aromatic hydrocarbon means benzene, naphthalene, anthracene etc.

The heterocycle means a group derived from a monocyclic ring containing 1 to 3 atoms of at least one member selected from the group consisting of sulfur atom, oxygen atom and nitrogen atom. For example, it means a pyrrole ring, thiophene ring, furan ring, thiazole ring, oxazole ring, isothiazole ring, isoxazole ring, imidazole ring, pyrazole ring, thiadiazole ring, oxadiazole ring, triazole ring, pyridine ring, pyridazine ring, pyrimidine ring, pyrazine ring etc.

The halogen atom means a fluorine atom, chlorine atom and iodine atom.

The lower alkyl group means a $C_1$ to $C_6$ linear or branched alkyl group such as methyl group, ethyl group, n-propyl group, n-butyl group, isopropyl group, isobutyl group and n-hexyl group.

The arylene group means the above aromatic hydrocarbon group having two bonds available for bonding.

The heteroarylene group means the above heterocyclic group having two bonds available for bonding.

The compound of formula (I) can be obtained easily by an ordinarily used method or a combination of ordinarily used methods. One example is as follows:

The compound wherein ring A is a pyrrole ring can be obtained in the following method.

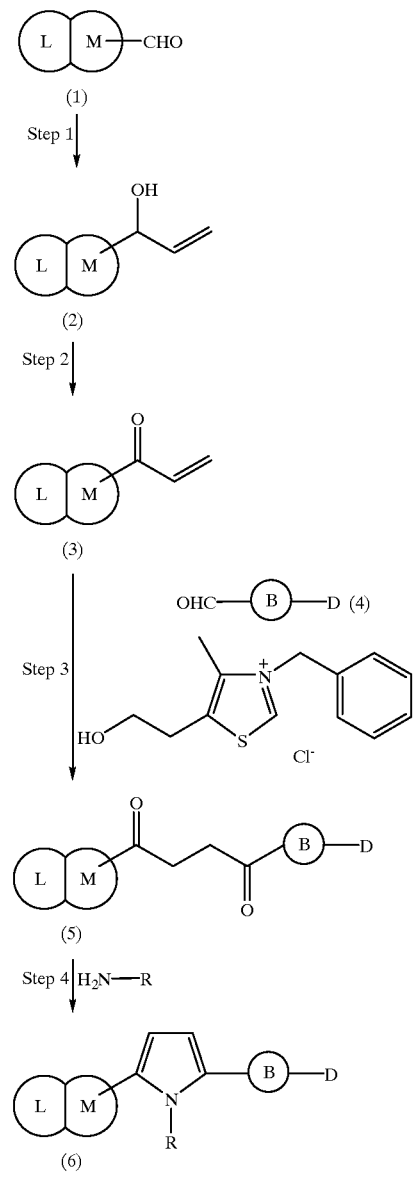

(Step 1)

In this reaction, the aldehyde (1) is reacted in a usual manner with an organometallic reagent to give the allyl alcohol (2).

The organometallic reagent includes e.g. a Grignard reagent, an organic lithium reagent, an organic zinc reagent and an organic copper complex. In the presence of a catalytic amount of copper iodide, the desired product can be produced in higher yield. The reaction solvent maybe any solvents which is inert to the reaction, and preferable examples include ether solvents such as ether and tetrahydrofuran. The reaction temperature is in the range of about −78° C. to the boiling point of the solvent, and preferably about −78° C. to 20° C.

(Step 2)

In this step, the allyl alcohol (2) obtained in step 1 is oxidized in a conventional manner to give the vinyl ketone (3).

The oxidation may be conducted in any ordinarily used methods, preferably using a suitable oxidizing agent. The examples of oxidizing agent used include activated manganese dioxide, chlorochromate pyridium, dichromate pyridium, a Dess-Martin reagent, a Swern oxidizing agent, TEMPO (sodium 2,2,6,6-tetramethyl-1-piperidinyloxy hypochlorite)-copper chloride, TEMPO-NaOCl etc. The reaction solvent may be any solvents which is inert to the reaction, and preferable examples include dichloromethane, chloroform, acetone etc. The reaction temperature is in the range of about −78° C. to the boiling point of the solvent, and preferably about −78° C. to 20° C.

(Step 3)

In this step, the diketone compound shown in the formula (5) is obtained by the method of Stetter 5 described in Org. Synth. 65, 26 by use of the vinyl ketone (3) obtained in step 2 and the aldehyde (4).

In this reaction, use of a thiazolium salt catalyst brings preferable results. For this reaction, a base such as triethylamine and sodium acetate is preferably used. A reaction solvent such as methanol, ethanol, N,N-dimethylformamide, etc. is used. The reaction temperature is preferably about 60° C. to the boiling point of the solvent.

(Step 4)

In this step, the diketone (5) obtained in step 3 is treated in a usual manner to give the pyrrole compound represented by the formula (6).

For example, by the reaction with an ammonium salt such as ammonium acetate or with a primary amine, the desired compound (6) can be obtained. In this case, an alcohol solvent such as methanol and ethanol, acetic acid or the like is used as the reaction solvent. The reaction temperature is preferably about 70° C. to the boiling point of the solvent.

The pyrrole (6) obtained in step 4 is hydrolyzed in a usual manner whereby its corresponding carboxylic acid compound can be obtained. In this case, use of a base brings good results. As the base, an aqueous solution of lithium hydroxide, sodium hydroxide, potassium hydroxide or the like gives rise to good results. The reaction solvent is preferably alcohol solvent such as methanol and ethanol or ether solvent such as tetrahydrofuran. The reaction temperature is preferably about 20° C. to the boiling point of the solvent.

Processes for producing the other compound group are disclosed in JP-A 9-71566, JP-A 2-240058, JP-A 2-768.62, JP-A 1-249783, JP-A 63-255277, JP-A 61-22047, and WO97/24116.

The compounds of the present invention are administered orally or parenterally. The compound group of the present invention can be administered in forms such as tablets, powder, granulates, capsules, syrups, troches, suppositories, injections, intravenous drip infusions, ointments, nasal drops, poultices and lotions.

The dose varies depending on the severeness of symptoms, the age, sex, weight and sensitivity of the patient, the administration method, administration time, administration intervals, the properties of the pharmaceutical preparation used, and its active ingredient, and there is no particular limit to the dose. Usually, the daily dose for an adult is 0.1 to 2000 mg, preferably 0.1 to 1000 mg. Usually this daily dose is administered in one portion or in divided portions. When administered in the form of an injection, usually 1 to 1000 μg/kg, preferably 1 to 300 μg/kg is administered.

EXAMPLES

Figure 1:
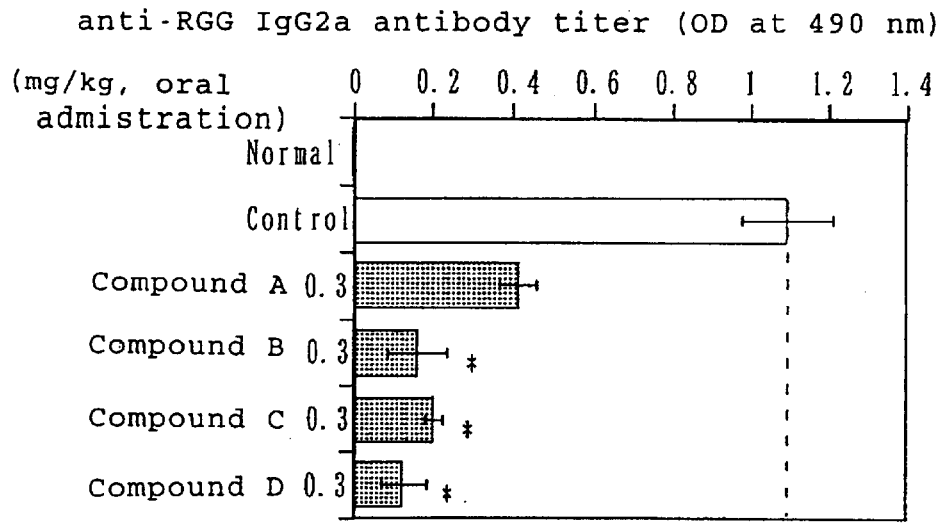
FIG. 1 shows the effect of compounds A, B, C and D on production of anti-rabbit γ-globulin (RGG) antibody in rats.

Hereinafter, the effects of the compounds of the present invention on nephritis and autoimmune diseases in which autoantibody is involved are described more in detail by reference to Examples.

In the test compounds used in the following experiment, compound A is 4-{2-[5-(4,7-dimethylbenzofuran-2-yl) pyrrolyl]}benzoic acid, compound B is 4-{2-[5-(7-fluoro-4-trifluoromethylbenzofuran-2-yl)pyrrolyl]}benzoic acid, compound C is 4-{2-[5-(3-fluoro-4,7-dimethylbenzofuran-2-yl)pyrrolyl]}benzoic acid, compound D is 4-{2-[5-(7-ethyl-4-methylbenzofuran-2-yl)pyrrolyl]}benzoic acid, compound E is 4-{2-{5-[2-(8,8-dimethyl-5,6,7,8-tetrahydroquinoxalynyl)]pyrrolyl}}benzoic acid, compound F is 4-{2-{5-[7-(1,5-dimethyl-2,3,4,5-tetrahydro-1H-benzazepinyl)]pyrrolyl}}benzoic acid, compound G is 4-{2-{5-[3-(1-ethyl-5-isopropylpyrazolyl]pyrrolyl}}benzoic acid, compound H is 4-{2-[5-(3-methoxymethyl-5,6,7,8-tetrahydro-5,5,8,8-tetramethylnaphthalene-2-yl) pyrrolyl}}benzoic acid, and compound I is 4-{[(3,5-bistrimethylsilylphenyl)carbonyl]amino}benzoic acid.

Example 1

A Rat Model with Accelerated Nephritis

Sprague-Dawley strain rats were immunized by subcutaneously administering rabbit γ-globulin in a dose of 4 mg/rat along with Freund's complete adjuvant into the bottoms of their both hind legs. On the 5th day after the rats were immunized, 1 ml of anti-rat glomerular basement membrane rabbit serum diluted 6- or 8-fold was administered via tail veins into the animals. On the 8th day, the rats were forced to be orally administered 8 ml sterilized water and then placed in a metabolism cage, and their urine was collected for 24 hours during which the animals were allowed neither food nor water. As the indicator of the model with accelerated Masugi nephritis, the amount of proteins excreted in urine for 24 hours was used.

The test compounds A, B, C, D, E, F, H and I were suspended respectively in 0.5% aqueous methyl cellulose solution and orally administered into the rats once every day from the day on which the animals were immunized with rabbit γ-globulin to the day before urine was collected from the animals. The medium was administered into the control group.

The results are shown in Table 1. Compounds A, B, C, D and H, in a dose of 0.3 mg/kg, inhibited albuminuria by 60 to 90% or more as compared with the control group. Further, compounds E, F and I, in a dose of 1 mg/kg, inhibited albuminuria by 70 to 80% or more as compared with the control group.

TABLE 1

Effect of Compounds A, B, C, D, E, F, H and I on the model with Accelerated Masugi Nephritis

| Test Compound | Dose (mg/kg) | Number of Animals | Degree of Inhibition of Albuminuria (%) |
| --- | --- | --- | --- |
| Compound A | 0.3 | 5 | 69.2 |
| Compound B | 0.3 | 5 | 90.7 |

TABLE 1-continued

Effect of Compounds A, B, C, D, E, F, H and I on the model with Accelerated Masugi Nephritis

| Test Compound | Dose (mg/kg) | Number of Animals | Degree of Inhibition of Albuminuria (%) |
|---|---|---|---|
| Compound C | 0.3 | 5 | 87.7 |
| Compound D | 0.3 | 5 | 80.3 |
| Compound E | 1.0 | 7 | 85.8 |
| Compound F | 1.0 | 7 | 71.1 |
| Compound H | 0.3 | 7 | 61.3 |
| Compound I | 1.0 | 7 | 89.4 |

Example 2
A Rat Model Producing Antibody

Sprague-Dawley strain rats were immunized by subcutaneously administering rabbit γ-globulin in a dose of 4 mg/rat along with Freund's complete adjuvant into the bottoms of their both hind legs. On the 14th day after the rats were immunized, blood was collected from their tail veins and examined for anti-rabbit γ-globulin antibody titer in serum by the ELISA method.

The test compounds A, B, C and D were suspended respectively in 0.5% aqueous methyl cellulose solution and orally administered once every day for 14 days from the day on which the animals were immunized with rabbit γ-globulin. The medium was administered into the control group.

The results are shown in Table 1.

Compounds B, C and D inhibited significantly in a dose of 0.3 mg/kg the anti-rabbit γ-globulin IgG2a antibody titer on the 14th day after immunization. Compound A showed a tendency to inhibit the antibody titer in a dose of 0.3 mg/kg.

Example 3
A Mouse Model Producing Antibody

BALB/c mice were immunized by administering dinitrophenylated keyhole limpet hemocyanin (DNP-KLH) as antigen intraperitoneally into them in a dose of 100 μg/mouse along with Freund's complete adjuvant. On the 10th day after the day on which the mice were immunized, blood was collected from the orbital venous plexus of the animals under anesthesia with ether and examined for anti-dintrophenyl (DNP) IgG2a antibody titer in serum by the ELISA method.

The test compounds B, E, F, G and H were suspended in 0.5% aqueous methyl cellulose solution and orally administered into the animals once every day for 10 days from the day when the animals were immunized with DNP-KLH. The medium was administered into the control group.

Figure 2:
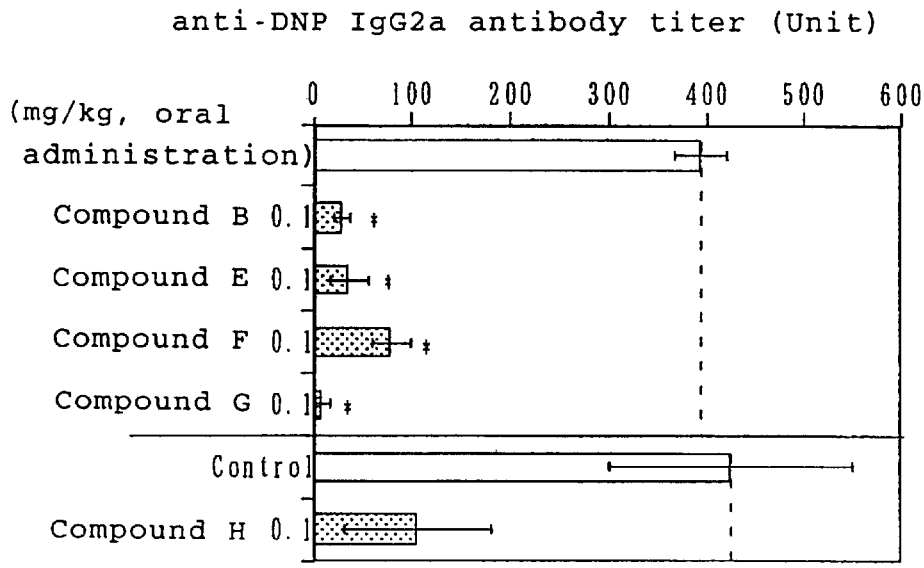
FIG. 2 shows the effect of compounds B, E, F, G and H on production of anti-dinitrophenyl (DNP) antibody in mice.

The results are shown in FIG. 2.

In a dose of 0.1 mg/kg, compounds B, E, F and G significantly inhibited anti-DNP IgG2a. In a dose of 0.1 mg/kg, compound H showed a tendency to inhibit anti-DNP IgG2a.

Figure 3:
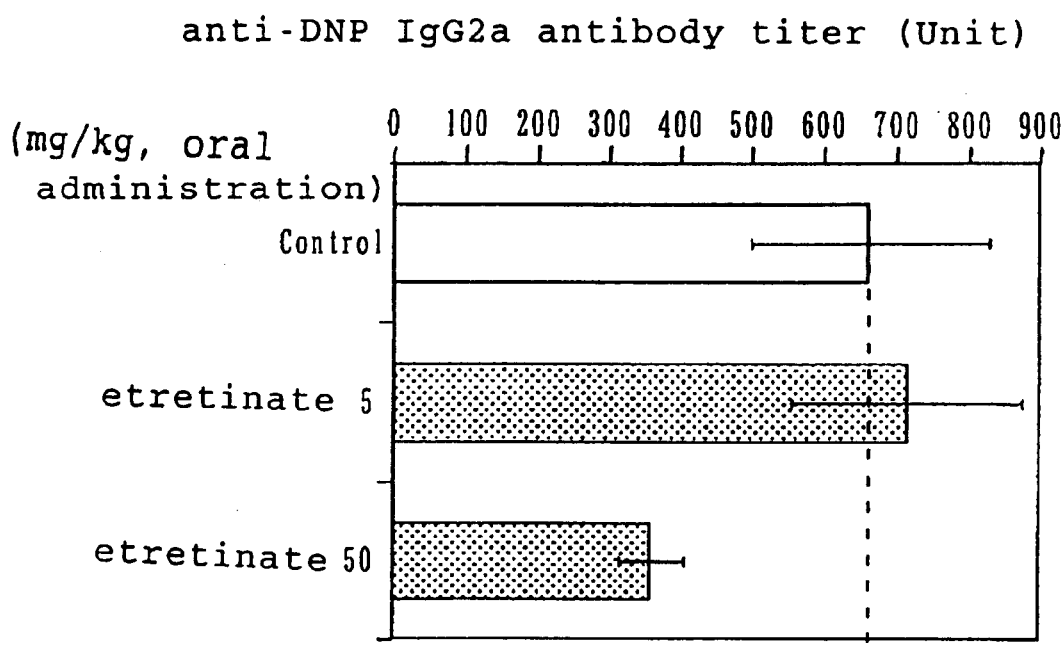
FIG. 3 shows the effect of etretinate on production of anti-dinitrophenyl (DNP) antibody in mice.

The RARα-selective agonists used here exhibited a potent inhibitory action on production of the antibody, as demonstrated above. Further, the action of etretinate (Tigason, Japan Roche), that is, an agonist unselective for RAR subtype, was examined by administration thereof in the same manner as for the above-described test compounds. 50 mg/kg etretinate also showed a tendency to inhibit production of the antibody in mice, but this effect was considerably lower than that of the RARα-selective agonists described above (FIG. 3). Accordingly, it was suggested that the inhibitory action of the retinoids on production of the antibody is a unique action which is significantly augmented by raising their selectivity for RARα.

Example 4
A Mouse Model with Spontaneous Onset of SLE

In this experiment, female (NZB×NZW) F1 mice were used. Administration of each test compound was initiated at the age of 16 weeks, and blood was collected at predetermined intervals from the orbital venous plexus of the animals under anesthesia with ether and examined for anti-DNA (single-stranded chain: ss, double stranded chain: ds) antibody titer in serum. Further, urine was collected and measured for urine protein.

The test compounds A, B and D were suspended in 0.5% aqueous methyl cellulose solution and orally administered daily once into the animals for 6 days/week for 18 weeks. The medium was administered into the control group.

Figure 4:
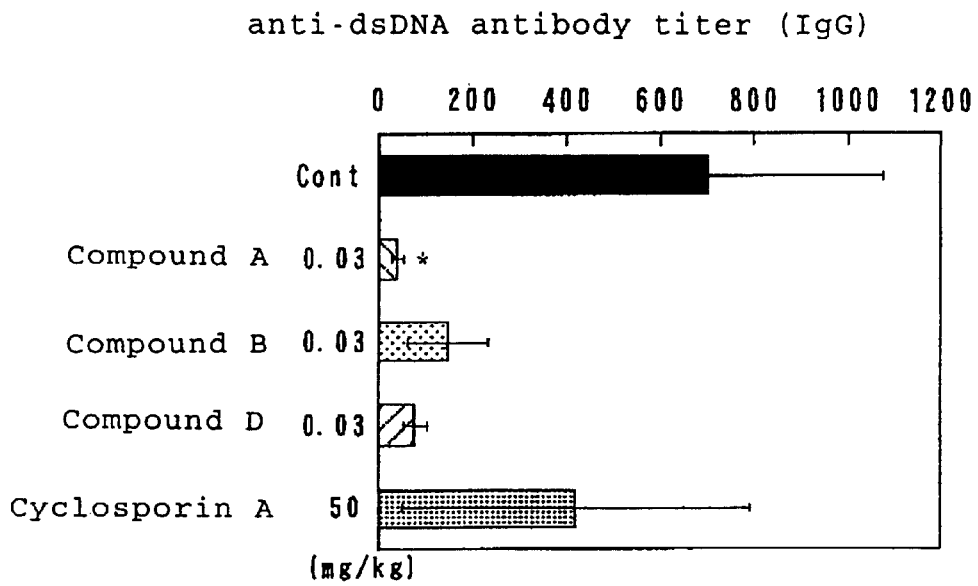
FIG. 4 shows the effect of compounds A, B and D on production of anti-DNA antibody in (NZB×NZW) F1 mice.
Figure 4:
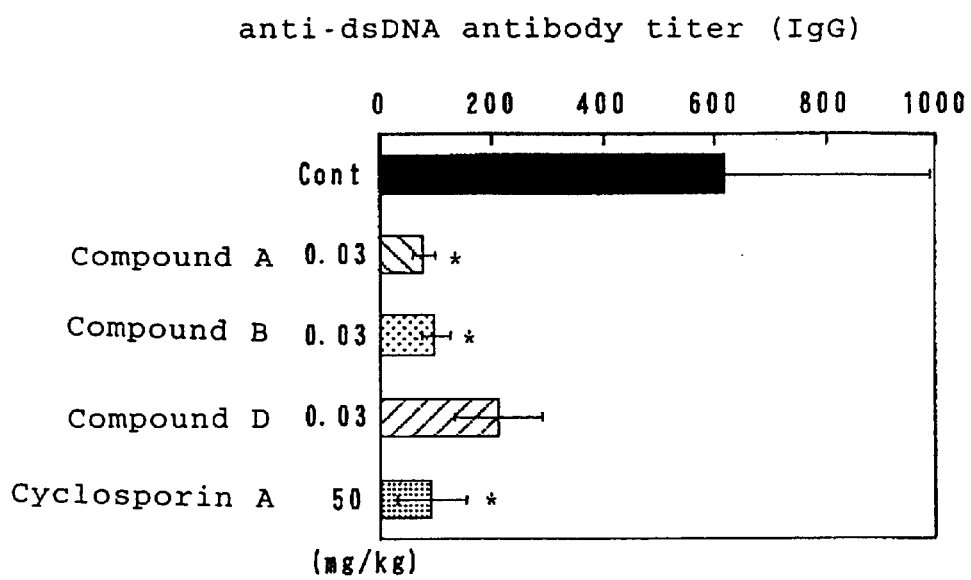

The effect of each compound on production of anti-DNA antibody after 16 weeks of administration (in 32-week-old animals) is shown in FIG. 4.

Production of anti-ds DNA antibody was inhibited by 80% or more by compounds A, B, and D, among which compound A showed significant inhibition in a dose of 0.03 mg/kg. Production of anti-ss DNA antibody was inhibited by 70% or more by compounds A, B, and D, among which compounds A and B showed significant inhibition in a dose of 0.03 mg/kg.

On the other hand, cyclosporin A which was examined in the same manner showed, in a dose of 50 mg/kg, about 85% significant inhibition on production of anti-ss DNA antibody, but did not inhibit production of anti-ds DNA antibody.

The effect of each compound on the onset of albuminuria after 18 weeks of administration (in 34-week-old animals) is shown in Table 2.

TABLE 2

Effects of Compounds A, B and D on Urine Protein in (NZB×NZW)F1 Mice

| Test Compound | Dose (mg/kg) | Number of Animals | Concentration of Urine Protein (mg/ml) | | | | | Level of Significance (p <0.05) |
|---|---|---|---|---|---|---|---|---|
| | | | >10 | >3 | >1 | >0.3 | <0.3 | |
| Control group | | 8 | 1 | 3 | 0 | 1 | 3 | |
| Compound A | 0.03 | 8 | 0 | 1 | 1 | 0 | 6 | |
| Compound B | 0.03 | 8 | 0 | 0 | 0 | 0 | 8 | * |

TABLE 2-continued

Effects of Compounds A, B and D on Urine Protein in (NZB×NZW)F1 Mice

| Test Compound | Dose (mg/kg) | Number of Animals | Concentration of Urine Protein (mg/ml) | | | | | Level of Significance (p <0.05) |
|---|---|---|---|---|---|---|---|---|
| | | | >10 | >3 | >1 | >0.3 | <0.3 | |
| Compound D | 0.03 | B | 0 | 0 | 0 | 0 | 8 | * |
| Cyclosporin A | 50 | 8 | 0 | 0 | 2 | 1 | 5 | |

Kruskal-Wallis H Test (Dunnett type multiple comparison)

The onset of albuminuria was inhibited by compounds A, B and D in a dose of 0.03 mg/kg, among which compounds B and D showed complete inhibition in a dose of 0.03 mg/kg. On the other hand, cyclosporin A showed inhibition in a dose of 50 mg/kg, though it was not statistically significant.

From the results described above, it was revealed that the RAR agonists, particularly RARα agonists strongly inhibit the production of antibody in normal rats and mice and the production of autoantibody in autoimmune mice. It was further revealed that glomerulonephritis and lupus nephritis in rats and mice were significantly inhibited via this potent inhibitory action on production of antibody.

The action of major compounds represented by the formulae (I) and (II) and compound I regarded as RARα agonist on each RAR subtype receptor was examined in the following manner.

Reference Example 1
RAR Binding Assay

Cells constantly expressing RARα, β and γ proteins were prepared by introducing human RARα, β and γ genes into BHK (baby hamster kidney) cells. A nuclear fraction of these cells was used to construct an experimental system for measuring the specific binding of all-trans-retinoic acid to RAR, and in this experimental system, the ability of each test compound to bind to PAR was examined by measuring the degree of inhibition of binding. Further, the ability of each test compound to bind to each receptor subtype was compared to determine the selectivity of the compound for RAR subtype.

(1) Experimental Method
a) Preparation of a Nuclear Extract Fraction $5 \times 10^8$ BHK cells having the RAR gene introduced into them were suspended in 15 ml solution A (5 mM sodium phosphate (pH 7.4), 10 mM monothioglycerol, 10% (v/v) glycerol, 1 mM phenyl methyl sulfonyl fluoride (PMSF), 10 µg/ml aprotinin, 25 µg/ml leupeptin), then homogenized therein and centrifuged, and the supernatant was removed. The resulting pellet was suspended in 15 ml buffer B (10 mM Tris-HCl (pH 8.5), 10 mM monothioglycerol, 10% (v/v) glycerol, 1 mM PMSF, 10 µg/ml aprotinin, 25 µg/ml leupeptin, 0.4 M potassium chloride), then left at 4° C. for 1 hour and ultracentrifuged at 100,000×g, 4° C. for 1 hour. The resulting supernatant was frozen and stored as a nuclear extract fraction at −80° C. until use (Methods in Enzymology, 189, 248).

b) Receptor Binding Assay

180 µl of the extract fraction and 10 µl diluted solution of all-trans-retinoic acid or a test compound were added to each well on a 96-well plate made of polypropylene, and further 10 µl of 10 nM $^3$H-all-trans-retinoic acid was added thereto and left at 4° C. for 16 hours. 3% charcoal-0.3% dextran solution was added to the reaction solution and centrifuged whereby free $^3$H-all-trans-retinoic acid was separated, and the count in the supernatant was determined by a scintillation counter. The count when a 500-fold excess of non-labeled all-trans-retinoic acid was added was subtracted as unspecific binding from the value obtained, to determine the amount of each compound binding specifically to RAR.

(2) Experiment Results

The concentration ($IC_{50}$) of each compound at which the binding of $^3$H-all-trans-retinoic acid was inhibited by 50% was determined and the results are shown in Tables 3-1 and 3-2.

TABLE 3-1

| Compound | Receptor binding assay $IC_{50}$ (nM) | | |
|---|---|---|---|
| | RAR-α | RAR-β | RAR-γ |
| 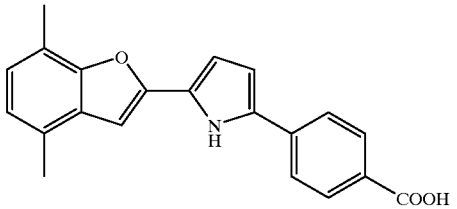 Compound A | 1.4 | 340 | >>500 |

TABLE 3-1-continued
| Compound | Receptor binding assay IC$_{50}$ (nM) | | |
|---|---|---|---|
| | RAR-α | RAR-β | RAR-γ |
| | 1.0 | 500 | >>500 |
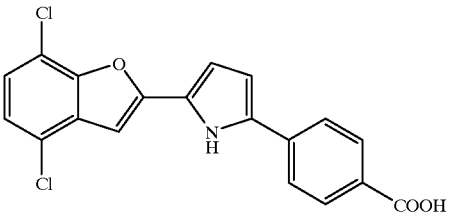
| | 3.8 | >500 | >>500 |
|---|---|---|---|
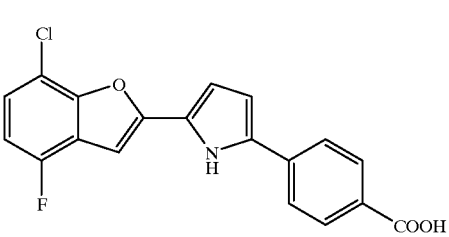
| | 0.6 | 107 | 195 |
|---|---|---|---|
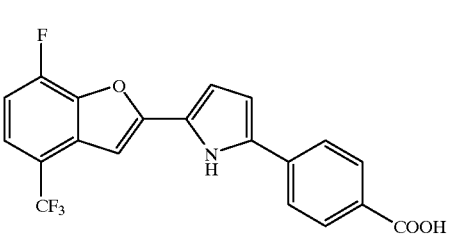
Compound B
| | <0.5 | 49 | 225 |
|---|---|---|---|
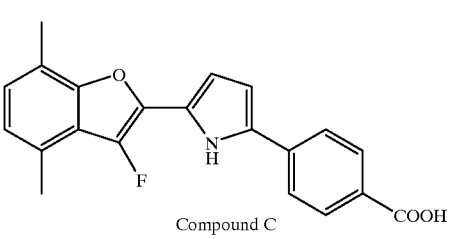
Compound C
| | <0.5 | 160 | 270 |
|---|---|---|---|
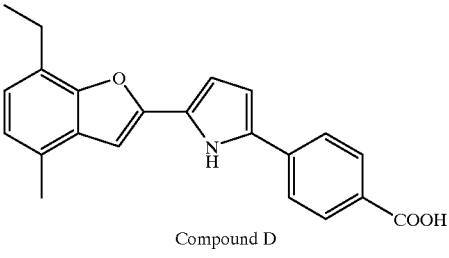
Compound D TABLE 3-2
| Compound | Receptor binding Assay IC$_{50}$ (nM) | | |
|---|---|---|---|
| | RAR-α | RAR-β | RAR-γ |
| 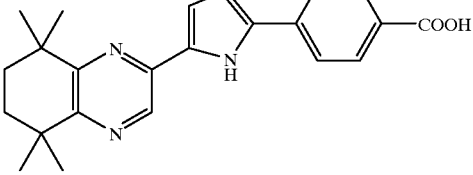 | 0.6 | 56 | 140 |
| 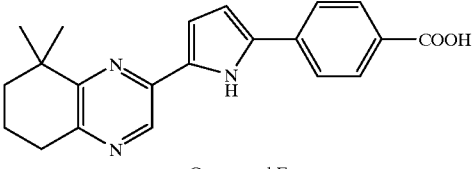 Compound E | not tested | not tested | not tested |
| 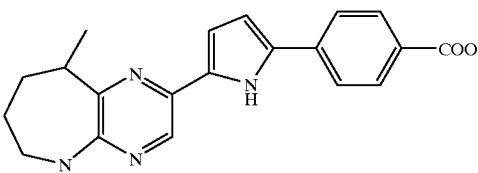 Compound F | 1.0 | 58 | 130 |
| 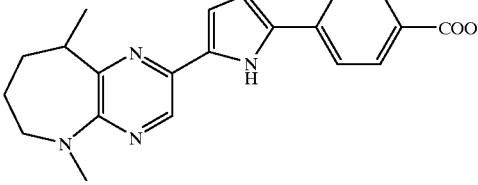 Compound G | not tested | not tested | not tested |
| 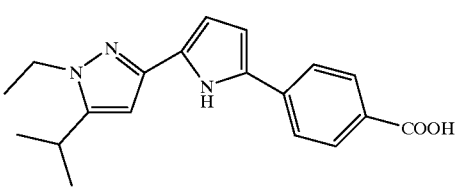 Compound H | 10 | 230 | 83 |
| 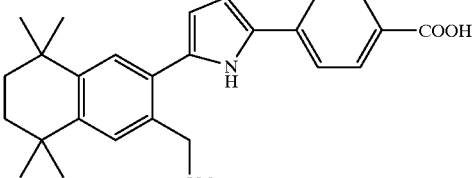 Compound I | 6.4 | >>500 | >>500 |

Referential Example 2
Transcription-Promoting Activity Via RAR

A human RAR expression vector and a secretory alkali phosphatase (PLAP) gene vector (PLAP vector) having a response sequence integrated upstream for allowing RAR-bound PLAP to be expressed depending on ligand, were tentatively introduced into COS-1 (renal cell line derived from African green monkey). The PLAP, which was produced depending on ligand and secreted into a culture liquid, was measured by chemiluminescence techniques to examine the transcription-promoting activity of each test compound. Further, the ability of the test compound to promote the transcription of each receptor subtype was compared to determine the selectivity of the compound for RAR subtype.

(1) Experimental Method $2.5 \times 10^4$ COS-1 cells were plated onto a 60-mm Petri dish, and after 4 days, the cells were transformed by lipofection with 4 μg expression vector for human RARα, RARβ or RARγ and 4 μg PLAP vector. After 1 day, the cells were recovered and plated at a density of $2 \times 10^4$ cells/well on a 96-well culture plate. After 4 hours, the medium was exchanged with a charcoal treated FBS-containing medium, then a diluted solution of all-trans-retinoic acid or a test compound was added thereto, and after 36 hours, the supernatant was recovered from the cell culture. The recovered sample was treated for 10 minutes at 65° C. to eliminate unspecific activity. 15 μl of the sample was mixed with 60 μl of 28 mM sodium carbonate buffer (pH 10) and reacted with 75 μl of a chemifluorescent substrate Smilight™ (Sumitomo Metal Industries, Ltd.) at 37° C. for 30 minutes to determine the fluorescence.

(2) Experimental Results

The concentration ($ED_{30}$) of each test compound showing 30% activity, where it was assumed that the average transcriptional activity induced by and 3 μM all-trans-retinoic acid was 100%, was determined. Then, the relative $ED_{30}$ of each compound, where it was assumed that the $ED_{30}$ of all-trans-retinoic acid for each receptor was 1, is shown as Relative $ED_{30}$* in Tables 4-1 and 4-2.

TABLE 4-1

| Compound | Receptor binding assay $IC_{50}$ (nM) | | |
|---|---|---|---|
| | RAR-α | RAR-β | RAR-γ |
| 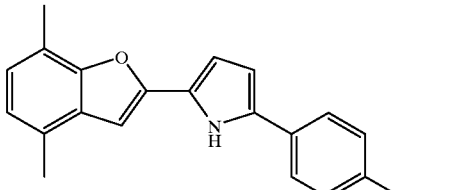 Compound A | 0.4 | 13 | 191 |
| 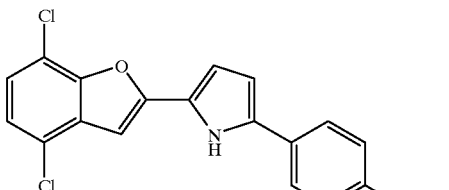 | 1.0 | 160 | 1400 |
| 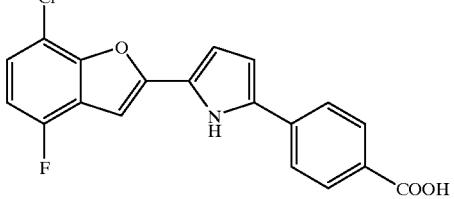 | 0.33 | 91 | 790 |
| 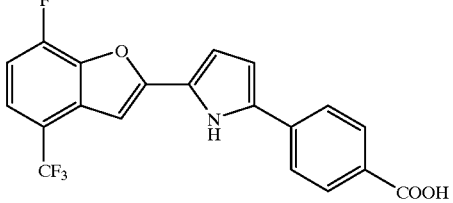 Compound B | 0.33 | 8.1 | 95 |

TABLE 4-1-continued

| Compound | Receptor binding assay IC$_{50}$ (nM) | | |
|---|---|---|---|
| | RAR-α | RAR-β | RAR-γ |
| | 0.39 | 2.8 | 31 |
| Compound C | | | |
| Compound D | 0.26 | 24 | 120 |

TABLE 4-2

| Compound | Transcription promoting activity ED$_{30}$* | | |
|---|---|---|---|
| | RAR-α | RAR-β | RAR-γ |
| | 0.21 | 1.4 | 1.9 |
| Compound E | 0.2 | 11 | 170 |

TABLE 4-2-continued

| Compound | Transcription promoting activity $ED_{50}$* | | |
|---|---|---|---|
| | RAR-α | RAR-β | RAR-γ |
| 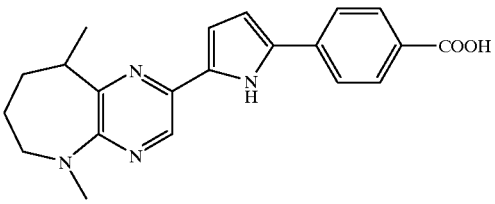
Compound F | 1.4 | 7.4 | 20 |
| 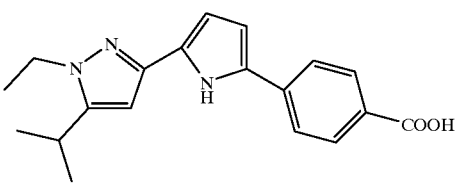
Compound G | 0.85 | 14 | 89 |
| 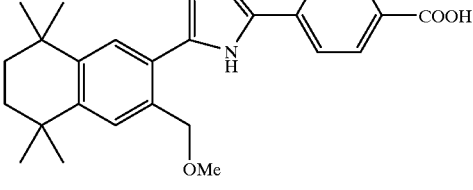
Compound H | 1.9 | 29 | 62 |
| 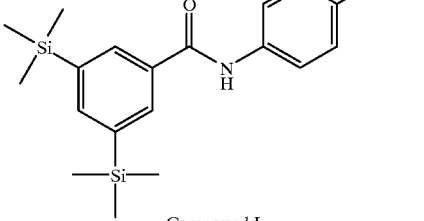
Compound I | 6 | 420 | 7800 |

From the above results, it is evident that these compounds have RAR agonist action and are particularly highly selective for RARα.

Some other compounds are described on pp. 85–88 in the Retinoids, 2nd ed. supra, Graupner, G., Malle, G. et al., Biochemical and Biophysical Research Communications, 179, 1554–1561, 1991, or Bruno A. Bernard et al., Biochemical and Biophysical Research Communications, 186, 977–983, 1992.

Reference Example 3
Involvement of RARα in Production of Antibody in Mouse Spleen Cells The action of all-trans retinoic acid on in vitro production of antibody in BALB/c mouse spleen cells was examined, and whether this action is via RARα or not was examined using Ro-41-5253 that is an RARα-selective antagonist (Apfel, C., Proc. Natl. Acad. Sci. USA, 89, 7129–7133, 1992).

(1) Experimental Method

Spleen cells from 7-week-old female BALB/c mouse were cultured at 37° C. in the presence of 5% $CO_2$ for 5 days along with 5 μg/ml lipopolysaccharide (LPS) in RPMI 1640 medium containing 10% fetal bovine serum. After culture, the total amount of IgG in the supernatant was quantified by specific ELISA techniques. The action of all-trans retinoic acid on this production of antibody was examined in the presence or absence of Ro-41-5253.

(2) Experimental Results
The results are shown in Table 5.

TABLE 5

Action of All-Trans-Retinoic Acid and RARα-Selective
Antagonist on in vitro Production of Antibody in Mice

| All-trans retinoic acid (nM) | Ro-41-5253 (nM) | | | |
|---|---|---|---|---|
| | 0 | 20 | 200 | 2000 |
| | Total IgG (ng/ml) | | | |
| 0 | 21.6 | 29.2 | 30.2 | 18.0 |
| 0.1 | 11.3 | 9.8 | 26.4 | 23.4 |
| 1 | 7.3 | 6.4 | 7.2 | 21.5 |

0.1 and 1 nM all-trans-retinoic acid inhibited in vitro production of antibody in mice. This inhibitory action was completely recovered by adding 200 nM and 2000 nM Ro-41-5253 that is an RARα-selective antagonist, thus indicating that the inhibition of production of antibody by the retinoide is a specific action via RARα.

Hereinafter, synthesis examples of mainly the compounds represented by the formula (I) are described, but as a matter of course the compounds encompassed by the present invention are not limited thereto.

Synthetic Example 1

4-{2-[5-(5,8-dimethylnaphthalene-2-yl)pyrroryl]}benzoic acid (A) 2-Acryloyl-5,8-dimethylnaphthalene 25 g of 5,8-dimethyltetralon was dissolved in 200 ml methanol in a nitrogen atmosphere, and 3.0 g of sodium borohydride was added thereto at 0° C. The mixture was stirred at 0° C. for 30 minutes, followed by adding an aqueous saturated ammonium chloride solution and then water. The resulting precipitates were filtered, washed with water and then dried to give 23.7 g alcohol compound. 23.7 g of the alcohol compound was dissolved in 60 ml N,N-dimethylformamide in a nitrogen atmosphere, and 25 ml phosphorus oxychloride was added dropwise thereto at 0° C. After the completion of the dropwise addition, the reaction mixture was heated under stirring at 100° C. for 2 hours. After the mixture was left standing for cooling to room temperature, ice-cold water and 9 g of sodium acetate were added thereto, and the resulting mixture was extracted with hexane (200 ml×4). The organic layers were combined, washed with brine, dried over anhydrous magnesium sulfate and then filtered. The resulting filtrate was concentrated to give 21.3 g aldehyde compound as a crude product.

20.9 g of the aldehyde compound was dissolved in 300 ml dioxane in a nitrogen atmosphere, then 50.9 g of dichlorodicyanobenzoquinone was added thereto, and the mixture was heated under reflux for 1.5 hours. After the mixture was left standing for cooling to room temperature, 500 ml toluene was added thereto, and the resulting precipitates were filtered off and washed with toluene several times. The filtrate was concentrated and the resulting crude product was purified by silica gel column chromatography to give 10.3 g of 5,8-dimethyl-2-naphthaldehyde as colorless crystals.

$^1$H-NMR (CDCl$_3$, 400 MHz) δ; 2.69(s,3H), 2.76(s,3H), 7.31(d,1H,J=7.2 Hz), 7.37(d,1H,J=7.2 Hz), 7.99(dd,1H,J=1.6,8.8 Hz), 8.11(d,1H,J=8.4 Hz), 8.51(d,1H,J=1.6 z), 10.2 (s,1H).

3.7 g of 5,8-dimethyl-2-naphthaldehyde was dissolved in 80 ml ether, and 30 ml (1.0 M) vinyl magnesium bromide solution in tetrahydrofuran was added thereto at −78° C., and the temperature was gradually raised to −30° C. The solution was quenched with an aqueous saturated ammonium chloride solution and then extracted with ethyl acetate (100 ml×2). The organic layers were combined, washed with brine, dried over anhydrous magnesium sulfate and then filtered. The resulting filtrate was concentrated to give 5.0 g allyl alcohol as a crude product.

The resulting product was dissolved in 30 ml dichloromethane, then 30 g activated manganese dioxide was added thereto, and the mixture was stirred for 40 hours at room temperature. After it was filtered through Celite, the filtrate was concentrated. The resulting crude product was purified by silica gel column chromatography to give 1.8 g of the title compound and simultaneously 1.2 g of the starting material was recovered.

$^1$H-NMR (CDCl$_3$, 400 MHz) δ; 2.68(s,3H), 2.74(s,3H), 6.00(dd,1H,J=1.6,10.4 Hz), 6.50(dd,1H,J=1.6,17.2 Hz), 7.27–7.39(m,3H), 8.06–8.10(m,2H), 8.64(s,1H).

(B) Methyl 4-[4-(5,8-dimethylnaphthalene-2-yl)-4-oxo-butanoyl]benzoate (Method 1)

A mixture of 1.8 g of 2-acryloyl-5,8-dimethylnaphthalene, 1.4 g of methyl tere-aldehyde-phthalate, 0.23 g of sodium acetate, 0.23 g of 3-benzyl-5-(2-hydroxymethyl)-4-methylthiazolium chloride and 100 ml ethanol was heated under reflux for 10 hours. The resulting crystals were filtered, washed with ethanol, and then dried to give 1.26 g of the title compound as colorless crystals.

(Method 2)

A mixture of 1.0 g of 5,8-dimethyl-2-naphthaldehyde, 1.2 g of methyl 4-acryloyl-benzoate, 0.28 g of 3-benzyl-5-(2-hydroxymethyl)-4-methylthiazolium chloride, 0.88 ml triethylamine and 20 ml N,N-dimethylformamide was heated under stirring at 70° C. for 3 hours. After the reaction solution was left standing for cooling to room temperature, water was added thereto, and the reaction solution was extracted with ethyl acetate (20 ml×3). The organic layers were combined, washed with brine, dried over anhydrous magnesium sulfate and filtered. Then, the filtrate was concentrated and the resulting crude crystals were washed with a mixed solvent of n-hexane and ethyl acetate to give 0.82 g of the title compound as colorless crystals.

$^1$H-NMR (CDCl$_3$, 400 MHz) δ; 2.68(s,H), 2.75(s,3H), 3.54(t,2H,J=6.4 Hz), 3.66(t,2H,J=6.4 Hz), 3.96(s,3H), 7.28 (d,1H,J=7.2 Hz), 7.33(d,1H,J=7.2 Hz), 8.06–8.18(m,6H), 8.75(d,1H,J=1.6 Hz).

(C) Methyl 4-{2-[5-(5,8-dimethylnaphthalene-2-yl)pyrrolyl]}benzoate

A mixture of 0.5 g of methyl 4-[4-(5,8-dimethylnaphthalene-2-yl)-4-oxo-butanoyl]benzoate, 2.0 g of ammonium acetate and 20 ml methanol was heated under reflux for 5 hours. The reaction solution was left standing for cooling to room temperature, and the resulting yellow crystals were filtered, washed with methanol and then dried to give 0.47 g methyl ester compound as yellow crystals.

$^1$H-NMR (CDCl$_3$, 400 MHz) δ; 2.67(s,3H), 2.73(s,3H), 3.93(s,3H) 6.76(m,2H), 7.18(d,1H,J=7.1 Hz), 7.23(d,1H,J= 7.1 Hz), 7.63(d,2H,J=8.6 Hz), 7.74(dd,1H,J=1.6,9.2 Hz), 8.03–8.09(m,4H) 8.84(s,1H).

(D) 4-{2-[5-(5,8-Dimethylnaphthalene-2-yl)pyrrolyl]}benzoic acid

A mixture of 0.68 g of the methyl ester compound, 40 ml ethanol and 4 ml of 5 N aqueous solution of sodium hydroxide was refluxed for 1 hour. The resulting pale yellow suspension was dissolved by adding water thereto, followed by adding 6 N hydrochloric acid (about 3.5 ml) and 40 ml water. The resulting crystals were filtered, washed with water and then dried to give 0.52 g of the title compound as yellow crystals.

$^1$H-NMR (DMSO-$d_6$, 400 MHz) δ; 2.59(s,3H), 2.69(s, 3H), 6.81(m,2H), 7.16(d,1H,J=7.1 Hz), 7.22(d,1H,J=7.1 Hz), 7.87–8.00(m,6H), 8.36(s,1H), 11.6(s,1H).

Synthetic Example 2

4-{2-[5-(5,7-dimethylnaphthalene-2-yl)pyrrolyl]}benzoic acid (A) 2-Acryloyl-5,7-dimethylnaphthalene The title compound was obtained in the same manner as in Synthetic Example 1 (A).

$^1$H-NMR (CDCl$_3$, 400 MHz) δ; 2.50(s,3H), 2.68(s,3H), 5.97(dd,1H,J=1.6,10.8 Hz), 6.49(dd,1H,J=1.6,17.2 Hz), 7.29(s,1H), 7.32(dd,1H,J=10.8,17.2 Hz), 7.59(s,8 H), 8.00 (m,2H), 8.37(s,1H)

(B) Methyl 4-[4-(5,7-dimethylnaphthalene-2-yl)-4-oxo-butanoyl]benzoate

The title compound was obtained in the same manner as in Method 1 of Synthetic Example 1 (B).

$^1$H-NMR (CDCl$_3$, 400 MHz) δ; 2.51(s,3H), 2.6(s,3H), 3.53(t,2H,J=6.1 Hz), 3.63(t,2H,J=6.1 Hz), 3.96(s,3H), 7.30 (s,1H), 7.61(s,1H), 8.01(d,1H,J=8.8 Hz), 8.03(dd,1H,J=1.6, 8.8 Hz), 8.12(d,2H,J=8.8 Hz), 8.15(d,2H,J=8.8 Hz), 8.48(s, 1H)

(C) Methyl 4-{2-[5-(5,7-dimethylnaphthalene-2-yl)pyrrolyl]}benzoate

The title compound was obtained in the same manner as in Synthetic Example 1 (C).

$^1$H-NMR (CDCl$_3$, 400 MHz) δ; 2.48(s,3H), 2.67(s,3H), 3.93(s,3H), 6.72–6.78(m,2H), 7.14(s,1H), 7.49(s,1H), 7.62 (d,2H,J=8.4 Hz), 7.67(dd,1H,J=1.6,8.8 Hz), 7.85(d,1H,J= 1.6 Hz), 7.97(d,1H,J=8.8 Hz), 8.07(d,2H,J=8.4 Hz), 8.82(s, 1H).

(D) 4-{2-[5-(5,7-Dimethylnaphthalene-2-yl)pyrrolyl]}benzoic acid

The title compound was obtained in the same manner as in Synthetic Example 1 (D).

$^1$H-NMR (DMSO-$d_6$, 400 MHZ) δ; 2.42(s,3H), 2.60(s, 3H), 6.79(m,2H), 7.13(s,1H), 7.48(s,1H), 7.84–7.94(m,6H), 8.21(s,1H), 11.5(s,1H)

Synthetic Example 3

4-{2-[5-(5,6,7,8-Tetramethylnaphthalene-2-yl)pyrrolyl]}benzoic acid (A) 2-Acryloyl-5,6,7,8-tetramethylnaphthalene The title compound was obtained in the same manner as in Synthetic Example 1 (A).

$^1$H-NMR (CDCl$_3$, 400 MHz) δ; 2.45(s,3H), 2.46(s,3H), 2.65(s,3H) 2.70(s,3H), 5.97(dd,1H,J=2.0,10.8 Hz), 6.50(dd, 1H,J=1.6,17.2 Hz), 7.36(dd,1H,J=10.8,17.2 Hz), 7.98(dd, 1H,J=1.6,8.8 Hz), 8.11(d,1H,J=8.8 Hz), 8.71(d,1H,J=1.6 Hz).

(B) Methyl 4-[4-(5,6,7,8-tetramethylnaphthalene-2-yl)-4-oxo-butanoyl]benzoate

The title compound was obtained in the same manner as in Method 1 of Synthetic Example 1 (B).

$^1$H-NMR (CDCl$_3$, 400 MHz) δ; 2.45(s,6H), 2.64(s,3H), 2.71(s,3H), 3.52(t,2H,J=6.2 Hz), 3.65(t,2H,J=6.2 Hz), 3.96 (s,3H), 7.92–8.20(m,6H), 8.80(s,1H).

(C) Methyl 4-{2-[5-(5,6,7,8-tetramethylnaphthalene-2-yl)pyrrolyl]}benzoate

The title compound was obtained in the same manner as in Synthetic Example 1 (C).

$^1$H-NMR (CDCl$_3$, 400 MHz) δ; 2.44(s,3H), 2.45(s,3H), 2.64(s,3H), 2.70(s,3H), 3.93(s,3H), 6.73(dd,1H,J=2.4,3.2 Hz), 6.77(dd,1H,J=2.4,3.2 Hz), 7.61–7.67(m,3H), 8.04–8.14 (m,4H), 8.82(brs,1H)

(D) 4-{2-[5-(5,6,7,8-tetramethylnaphthalene-2-yl)pyrrolyl]}benzoic acid

The title compound was obtained in the same manner as in Synthetic Example 1 (D).

$^1$H-NMR (DMSO-$d_6$, 400 MHz) δ; 2.37(s,3H), 2.38(s, 3H), 2.56(s,3H), 2.67(s,3H), 6.79(m,2H), 7.83(dd,1H,J=1.2, 8.8 Hz), 7.89(d,2H,J=8.0 Hz), 7.93(d,2H,J=8.0 Hz), 8.39(d, 1H,J=1.2 Hz), 11.6(s,1H).

Synthetic Example 4

4-{2-[5-(7-Methoxy-8-methylnaphthalene-2-yl)pyrrolyl]}benzoic acid (A) Methyl 4-[4-(7-methoxy-8-methylnaphthalene-2-yl)-4-oxo-butanoyl]benzoate The title compound was obtained in the same manner as in Method 2 of Synthetic Example 1 (B).

$^1$H-NMR (CDCl$_3$, 400 MHz) δ; 2.64(s,3H), 3.53(t,2H,J= 6.0 Hz), 3.65(t,2H,J=6.0 Hz), 3.96(s,3H), 3.98(s,3H), 7.38 (d,1H,J=9.2 Hz), 7.76(d,1H,J=9.2 Hz), 7.85(d,1H,J=8.8 Hz), 7.93(dd,1H,J=1.6,8.8 Hz), 8.12(d,2H,J=8.8 Hz), 8.15(d,2H, J=8.8 Hz), 8.71(m,1H).

(B) Methyl 4-{2-[5-(7-methoxy-8-methylnaphthalene-2-yl)pyrrolyl]}benzoate

The title compound was obtained in the same manner as in Synthetic Example 1 (C).

$^1$H-NMR (CDCl$_3$, 400 MHz) δ; 2.62(s,3H), 3.94(s,3H), 3.97(s,3H), 6.73–6.78(m,2H), 7.24(d,1H,J=8.8 Hz), 7.56 (dd,1H,J=2.0,8.4 Hz), 7.63(d,2H,J=8.4 Hz), 7.70(d,1H,J= 8.8 Hz), 7.81(d,1H,J=8.4 Hz), 8.02(s,1H), 8.07(d,2H,J=8.4 Hz), 8.83(brs,1H).

(C) 4-{2-[5-(7-methoxy-8-methylnaphthalene-2-yl)pyrrolyl]}benzoic acid

The title compound was obtained in the same manner as in Synthetic Example 1 (D).

$^1$H-NMR (DMSO-$d_6$, 400 MHz) δ; 2.56(s,3H), 3.90(s, 3H), 6.81(d,2H,J=2.2 Hz), 7.33(d,1H,J=8.9 Hz), 7.72–7.77 (m,2H), 7.82(d,1H,J=8.4 Hz), 7.90(d,2H,J=8.8 Hz), 7.93(d, 2H,J=8.8 Hz), 8.30(s,1H), 11.6(s,1H).

Synthetic Example 5

4-{2-[5-(7-Methoxy-8-ethylnaphthalene-2-yl)pyrrolyl]}benzoic acid (A) Methyl 4-[4-(7-methoxy-8-ethylnaphthalene-2-yl)-4-oxo-butanoyl]benzoate The title compound was obtained in the same manner as in Method 2 of Synthetic Example 1 (B).

¹H-NMR (CDCl₃, 400 MHz) δ; 1.27(t,3H,J=7.4 Hz), 3.18(q,2H,J=7.4 Hz), 3.54(t,2H,J=6.1 Hz), 3.64(t,2H,J=6.1 Hz), 3.96(s,3H), 3.98(s,3H), 7.39(d,1H,J=9.2 Hz), 7.76(d,2H,J=9.2 Hz), 7.85(d,1H,J=8.4 Hz), 7.92(dd,1H,J=1.6,8.4 Hz), 8.13(d,2H,J=8.4 Hz), 8.16(d,2H,J=8.4 Hz), 8.72(s,1H).

(B) Methyl 4-{2-[5-(7-methoxy-8-ethylnaphthalene-2-yl)pyrrolyl]}benzoate

The title compound was obtained in the same manner as in Synthetic Example 1 (C).

¹H-NMR (CDCl₃, 400 MHz) δ; 1.29(t,3H,J=7.5 Hz), 3.16(q,2H,J=7.5 Hz), 3.94(s,3H), 3.97(s,3H), 6.73–6.78(m,2H), 7.24(d,2H,J=8.8 Hz), 7.54(dd,2H,J=2.0,8.4 Hz), 7.63(d,2H,J=8.0 Hz), 7.70(d,1H,J=8.8 Hz), 7.82(d,1H,J=8.4 Hz), 8.04(s,1H), 8.07(d,2H,J=8.0 Hz), 8.82(brs,1H)

(C) 4-{2-[5-(7-Methoxy-8-ethylnaphthalene-2-yl)pyrrolyl]}benzoic acid

The title compound was obtained in the same manner as in Synthetic Example 1 (D).

¹H-NMR (DMSO-d₆, 400 MHz) δ; 1.18(t,3H,J=7.6 Hz), 3.14(q,2H,J=7.6 Hz), 3.91(s,3H), 6.81(m,2H), 7.33(d,1H,J=8.8 Hz), 7.74(d,2H,J=8.8 Hz), 7.83(d,1H,J=8.8 Hz), 7.91(d,2H,J=8.4 Hz), 7.94(d,2H,J=8.4 Hz), 8.28(s,1H) 18.6(s,1H)

Synthetic Example 6

4-{2-[5-(8-Methylnaphthalene-2-yl)pyrrolyl]}benzoic acid (A) Methyl 4-[4-(8-methylnaphthalene-2-yl)-4-oxo-butanoyl]benzoate The title compound was obtained in the same manner as in Method 2 of Synthetic Example 1 (B).

¹H-NMR (CDCl₃, 400 MHz) δ; 2.79(s,3H), 3.54(t,2H,J=6.4 Hz), 3.66(t,2H,J=6.4 Hz), 3.96(s,3H), 7.40(d,1H,J=8.0 Hz), 7.50(t,1H,J=8.0 Hz), 7.74(d,1H,J=8.0 Hz), 7.92(d,1H,J=8.4 Hz), 8.08(dd,1H,J=2.0,8.4 Hz), 8.12(d,2H,J=8.8 Hz), 8.16(d,2H,J=8.8 Hz), 8.75(s,1H).

(B) Methyl 4-{2-[5-(8-methylnaphthalene-2-yl)pyrrolyl]}benzoate

The title compound was obtained in the same manner as in Synthetic Example 1 (C).

¹H-NMR (CDCl₃, 400 MHz) δ; 2.76(s,3H), 3.94(s,3H), 6.74–6.78(m,2H), 7.34–7.36(m,2H), 7.64(d,2H,J=8.4 Hz), 7.68–7.72(m,2H), 7.88(d,1H,J=8.4 Hz), 8.06–8.10(m,3H), 8.84(brs,1H).

(C) 4-{2-[5-(8-Methylnaphthalene-2-yl)pyrrolyl]}benzoic acid

The title compound was obtained in the same manner as in Synthetic Example 1 (D).

¹H-NMR (DMSO-d₆, 400 MHz) δ; 2.73(s,3H), 6.83(d,2H,J=2.0 Hz), 7.30–7.36(m,2H), 7.70(m,1H), 7.86–7.96(m,6H), 8.37(s,1H), 11.6(s,1H).

Synthetic Example 7

4-{2-[5-(8-Ethylnaphthalene-2-yl)pyrrolyl]}benzoic acid (A) Methyl 4-[4-(8-Ethylnaphthalene-2-yl)-4-oxo-butanoyl]benzoate The title compound was obtained in the same manner as in Method 2 of Synthetic Example 1 (B).

¹H-NMR (CDCl₃, 400 MHz) δ; 1.42(t,3H,J=7.5 Hz), 3.20(q,2H,J=7.5 Hz), 3.55(t,2H,J=6.4 Hz), 3.65(t,2H,J=6.4 Hz), 3.96(s,3H), 7.42(d,1H,J=7.6 Hz), 7.53(t,1H,J=7.6 Hz), 7.74(d,1H,J=8.0 Hz), 7.92(d,1H,J=8.8 Hz), 8.07(dd,1H,J=2.0,8.8 Hz), 8.13(d,2H,J=8.4 Hz), 8.16(d,2H,J=8.4 Hz), 8.81(s,1H).

(B) Methyl 4-{2-[5-(8-ethylnaphthalene-2-yl)pyrrolyl]}benzoate

The title compound was obtained in the same manner as in Synthetic Example 1 (C)

¹H-NMR (CDCl₃, 400 MHz) δ; 1.44(t,3H,J=7.5 Hz), 3.18(q,2H,J=7.5 Hz), 3.94(s,3H), 6.74(dd,1H,J=2.8,3.6 Hz), 6.78(dd,1H,J=2.8,3.6 Hz), 7.36–7.42(m,2H), 7.63(d,2H,J=8.4 Hz), 7.67–7.70(m,2H), 7.89(d,1H,J=8.8 Hz), 8.08(d,2H,J=8.4 Hz), 8.13(s,1H), 8.82(brs,1H).

(C) 4-{2-[5-(8-Ethylnaphthalene-2-yl)pyrrolyl]}benzoic acid

The title compound was obtained in the same manner as in Synthetic Example 1 (D).

¹H-NMR (DMSO-d₆, 400 MHz) δ; 1.35(t,3H,J=7.5 Hz), 3.18(q,2H,J=7.5 Hz), 6.82(s,2H), 7.34–7.37(m,2H), 7.70(m,1H), 7.88–7.96(m,6H), 8.41(s,1H), 11.6(s,1H).

Synthetic Example 8

4-{2-[5-(8-isopropylnaphthalene-2-yl)pyrrolyl]}benzoic acid (A) Methyl 4-[4-(8-isopropylnaphthalene-2-yl)-4-oxo-butanoyl]benzoate The title compound was obtained in the same manner as in Method 2 of Synthetic Example 1 (B).

¹H-NMR (CDCl₃, 400 MHz) δ; 1.44(d,6H,J=7.0 Hz), 3.54(t,2H,J=6.4 Hz), 3.66(t,2H,J=6.4 Hz), 3.87(q,1H,J=7.0 Hz), 3.96(s,3H), 7.50(d,1H,J=8.0 Hz), 7.58(t,1H,J=8.0 Hz), 7.73(d,1H,J=8.0 Hz), 7.92(d,1H,J=8.4 Hz), 8.06(dd,1H,J=1.6,8.8 Hz), 8.12(d,2H,J=8.0 Hz), 8.16(d,2H,J=8.0 Hz), 8.90(s,1H).

(B) Methyl 4-{2-[5-(8-isopropylnaphthalene-2-yl)pyrrolyl]}benzoate

The title compound was obtained in the same manner as in Synthetic Example 1 (C).

¹H-NMR (CDCl₃, 400 MHz) δ; 1.45(d,6H,J=7.2 Hz), 3.83(quint.,1H,J=7.2 Hz), 3.94(s,3H), 6.74(dd,1H,J=2.4,4.0 Hz), 6.78(dd,1H,J=2.4,4.0 Hz), 7.41–7.46(m,2H), 7.63(d,2H,J=8.8 Hz), 7.67–7.70(m,2H), 7.89(d,1H,J=8.4 Hz), 8.07(d,2H,J=8.8 Hz), 8.21(s,1H), 8.82(brs,1H)

(C) 4-{2-[5-(8-Isopropylnaphthalene-2-yl)pyrrolyl]}benzoic acid

The title compound was obtained in the same manner as in Synthetic Example 1 (D).

¹H-NMR (DMSO-d₆, 400 MHz) δ; 1.37(d,6H,J=6.8 Hz), 3.96(quint.,1H,J=6.8 Hz), 6.81(m,2H), 7.37–7.44(m,2H), 7.69(d,1H,J=8.0 Hz), 7.88–7.96(m,6H), 8.48(s,1H), 11.6(s,1H).

Synthetic Example 9

4-{2-[5-(8-Isopropenylnaphthalene-2-yl)pyrrolyl]}benzoic acid (A) Methyl 4-[4-(8-isopropenylnaphthalene-2-yl)-4-oxo-butanoyl]benzoate The title compound was obtained in the same manner as in Method 2 of Synthetic Example 1 (B).

¹H-NMR (CDCl₃, 400 MHz) δ; 2.25(s,3H), 3.52(t,2H,J=6.4 Hz), 3.63(t,2H,J=6.4 Hz), 3.96(s,3H), 5.10(m,1H), 5.51(m,1H), 7.40(dd,1H,J=1.2,6.8 Hz), 7.56(t,1H,J=8.0 Hz), 7.79(d,1H,J=8.4 Hz), 7.91(d,1H,J=8.4 Hz), 8.06(dd,1H,J=2.0,8.8 Hz), 8.11(d,2H,J=8.4 Hz), 8.16(d,2H,J=8.4 Hz), 8.82(s,1H).

(B) Methyl 4-{2-[5-(8-isopropenylnaphthalene-2-yl)pyrrolyl]}benzoate

The title compound was obtained in the same manner as in Synthetic Example 1 (C).

¹H-NMR (CDCl₃, 400 MHz) δ; 2.28(s,3H), 3.94(s,3H), 5.13(m,1H), 5.49(m,1H), 6.72(dd,1H,J=2.8,3.6 Hz), 6.76(dd,1H,J=2.4,3.6 Hz), 7.34(dd,1H,J=1.6,7.2 Hz), 7.41(dd,1H,J=7.2,8.0 Hz), 7.62(d,2H,J=8.8 Hz), 7.70(dd,1H,J=2.0,8.8 Hz), 7.74(d,1H,J=8.0 Hz), 7.88(d,1H,J=8.4 Hz), 8.07(d,2H,J=8.8 Hz), 8.14(s,1H), 8.79(brs,1H).

(C) 4-{2-[5-(8-Isopropenylnaphthalene-2-yl)pyrrolyl]}benzoic acid

The title compound was obtained in the same manner as in Synthetic Example 1 (D).

¹H-NMR (DMSO-d₆, 400 MHz) δ; 2.23(s,3H), 5.07(m,1H), 5.46(m,1H), 6.70(m,1H), 6.81(m,1H), 7.31(d,1H,J=7.2 Hz), 7.40(t,1H,J=8.0 Hz), 7.88–7.95(m,6H), 8.23(s,1H), 11.6(s,1H).

Synthetic Example 10

4-{2-[5-(8-Phenylnaphthalene-2-yl)pyrrolyl]}benzoic acid (A) Methyl 4-[4-(8-phenylnaphthalene-2-yl)-4-oxo-butanoyl]benzoate The title compound was obtained in the same manner as in Method 2 of Synthetic Example 1 (B).

¹H-NMR (CDCl₃, 400 MHz) δ; 3.45(m,4H), 3.95(s,3H), 7.46–7.54(m,6H), 7.66(t,1H,J=8.0 Hz), 7.90(d,1H,J=8.4 Hz), 7.98(d,1H,J=8.8 Hz), 8.06–8.10(m,3H), 8.13(d,2H,J=8.4 Hz), 8.66(s,1H).

(B) Methyl 4-{2-[5-(8-phenylnaphthalene-2-yl)pyrrolyl]}benzoate

The title compound was obtained in the same manner as in Synthetic Example 1 (C).

¹H-NMR (CDCl₃, 400 MHz) δ; 3.92(s,3H), 6.64(dd,1H,J=2.4,3.6 Hz), 6.71(dd,1H,J=2.4,3.6 Hz), 7.44(dd,1H,J=1.6,7.2 Hz), 7.48–7.56(m,8H), 7.72(dd,1H,J=1.6,8.4 Hz), 7.84(d,1H,J=8.4 Hz), 7.94(d,1H,J=8.4 Hz), 8.00(s,1H), 8.03(d,2H,J=8.4 Hz), 8.71(brs,1H).

(C) 4-{2-[5-(8-Phenylnaphthalene-2-yl)pyrrolyl]}benzoic acid

The title compound was obtained in the same manner as in

Synthetic Example 1 (D).

¹H-NMR (DMSO-d₆, 400 MHz) δ; 6.48(m,1H), 6.72(m,1H), 7.41(dd,1H,J=1.2,6.8 Hz), 7.46–7.58(m,6H) 7.78(d,2H,J=8.4 Hz), 7.88(d,2H,J=8.4 Hz), 7.91(d,1H,J=8.4 Hz), 8.00(dd,1H,J=1.2,7.8 Hz), 8.02(d,1H,J=7.8 Hz), 8.09(s,1H), 11.6(s,1H).

Synthetic Example 11

4-{2-[5-(5,8-Dimethylnaphthalene-2-yl)-1-methylpyrrolyl]}benzoic acid (A) Methyl 4-{2-[5-(5,8-dimethylnaphthalene-2-yl)-1-methylpyrrolyl]}benzoate 240 mg of methyl 4-{2-[5-(5,8-dimethylnaphthalene-2-yl)pyrrolyl]}benzoate was dissolved in 5 ml N,N-dimethylformamide in a nitrogen atmosphere, and 33 mg of (60%) sodium hydride was added thereto and stirred for 1 hour. Subsequently, 0.06 ml methyl iodide was added dropwise thereto at 0° C. and stirred at room temperature for 1 hour. An aqueous saturated ammonium chloride solution was added thereto, then the mixture was extracted with ethyl acetate (30 ml×2). The organic layers were combined and washed with brine. It was dried over anhydrous magnesium sulfate and then filtered, and the filtrate was concentrated to give 300 mg of the title compound as a crude product.

¹H-NMR (CDCl₃, 400 MHz) δ; 2.70(s,6H), 3.72(s,3H), 3.94(s,3H), 6.47(d,1H,J=3.6 Hz), 6.49(d,1H,J=3.6 Hz), 7.21–7.26(m,2H), 7.59(d,2H,J=8.0 Hz), 7.66(dd,1H,J=1.6,8.4 Hz), 8.06–8.12(m,4H).

(B) 4-{2-[5-(5,8-Dimethylnaphthalene-2-yl)-1-methylpyrrolyl]}benzoic acid

The title compound was obtained in the same manner as in Synthetic Example 1 (D).

¹H-NMR (DMSO-d₆, 400 MHz) δ; 2.62(s,3H), 2.66(s,3H), 3.71(s,3H), 6.48(m,2H), 7.24(d,1H,J=6.8 Hz), 7.26(d,1H,J=6.8 Hz), 7.68(d,2H,J=8.0 Hz), 7.73(d,1H,J=7.6 Hz), 7.99(d,2H,J=8.0 Hz), 8.07(m,2H).

Synthetic Example 12

4-{2-[5-(5,8-Dimethpylnaphthalene-2-yl)-1-isoproplpyrrolyl]}benzoic acid (A) Methyl 4-{2-[5-(5,8-dimethylnaphthalene-2-yl)-1-isopropylpyrrolyl]}benzoate 0.23 g of methyl 4-[4-(5,8-dimethylnaphthalene-2-yl)-4-oxo-butanoyl]benzoate was dissolved in 4 ml acetic acid, and 4 ml isopropylamine was added thereto at room temperature and heated under reflux for 2 hours. After the reaction solution was left standing for cooling to room temperature, water was added thereto, then the mixture was extracted with ethyl acetate (30 ml×2). The organic layers were combined and washed with an aqueous saturated sodium bicarbonate solution and then with brine. It was dried over anhydrous magnesium sulfate and filtered. The filtrate was concentrated, and then the resulting crude product which was purified by silica gel column chromatography to give 95 mg of the title compound.

¹H-NMR (CDCl₃, 400 MHz) δ; 1.30(d,6H,J=7.0 Hz), 2.69(s,3H), 2.71(s,3H), 3.96(s,3H), 4.58(quint.,1H,J=7.0 Hz), 6.29(s,2H), 7.23–7.28(m,2H), 7.58(d,2H,J=8.2 Hz), 7.65(dd,1H,J=1.6,8.4 Hz), 8.05(d,1H,J=8.4 Hz), 8.08–8.11(m,3H).

(B) 4-{2-[5-(5,8-Dimethylnaphthalene-2-yl)-1-isopropylpyrrolyl]}benzoic acid

The title compound was obtained in the same manner as in Synthetic Example 1 (D).

¹H-NMR (DMSO-d₆, 400 MHz) δ; 1.22(d,6H,J=7.0 Hz), 2.63(s,6H), 4.50(quint.,1H,J=7.0 Hz), 6.23(s,2H), 7.27(q, AB type, 2H,J=6.8 Hz), 7.58(d,2H,J=8.0 Hz), 7.64(dd,1H, J=1.6,8.8 Hz), 7.99(m,3H), 8.06(d,1H,J=8.8 Hz), 12.9(brs.1H).

Synthetic Example 13

4-{2-[5-(4,7-Dimethylbenzofuran-2-yl)pyrrolyl]}benzoic acid (A) methyl 4-[4-(4,7-dimethylbenzofuran-2-yl)-4-oxo-butanoyl]benzoate 22.6 g of anhydrous potassium carbonate and 14.8 ml bromoacetaldehyde diethyl acetal were added to 100 ml solution of 10 g 2,5-dimethylphenol in N,N-dimethylformamide and heated under stirring at 150° C. for 2.5 hours. After the mixture was left standing for cooling to room temperature, it was extracted with ethyl acetate. The organic layer was washed with brine and then dried over anhydrous magnesium sulfate. The solvent was evaporated, and the resulting residue was purified by silica gel column chromatography to give 18 g ether compound as a colorless oil.

The resulting oil was dissolved in 100 ml toluene, and 50 g of polyphosphoric acid was added thereto and heated under stirring at 90° C. for 1 hour in a nitrogen atmosphere. After the mixture was left standing for cooling to room temperature, it was poured into ice-cold water and extracted with ethyl acetate. The organic layer was washed with brine and then dried over anhydrous magnesium sulfate. The solvent was evaporated, and the resulting residue was purified by silica gel column chromatography to give 3.5 g of 4,7-dimethylbenzofuran as a yellow oil.

18.4 ml n-butyl lithium (1.56 M solution in hexane) was added to 50 ml solution of 3.5 g 4,7-dimethylbenzofuran in anhydrous tetrahydrofuran at −35° C. in a nitrogen atmosphere. After stirring for 15 minutes, 5.6 ml N,N-dimethylformamide was added dropwise thereto, and the temperature was raised to room temperature. Ethyl acetate was added to the reaction mixture, and the organic layer was washed with brine and then dried over anhydrous magnesium sulfate. The solvent was evaporated, and the resulting crude crystals were washed with n-hexane to give 2.3 g of 4,7-dimethylbenzofuran-2-carbaldehyde as a pale yellow solid.

$^1$H-NMR (CDCl$_3$, 400 MHz) δ; 2.53(s,6H), 7.02(d,1H,J=6.8 Hz), 7.20(d,1H,J-6.8 Hz), 7.59(s,1H), 9.85(s,1H).

Using the resulting 4,7-dimethylbenzofuran-2-carbaldehyde, the title compound was obtained in the same manner as in Method 2 of Synthetic Example 1 (B).

$^1$H-NMR (CDCl$_3$, 400 MHz) δ; 2.50(s,3H), 2.51(s,3H), 3.45–3.55(m,4H), 3.94(s,3H), 7.00(d,1H,J=6.8 Hz), 7.16(d, 1H,J=6.8 Hz), 7.62(s,1H), 8.09(d,2H,J=8.4 Hz), 8.14(d,2H, J=8.4 Hz).

(B) Methyl 4-{2-[5-(4,7-dimethylbenzofuran-2-yl)pyrrolyl]}benzoate

The title compound was obtained in the same manner as in Synthetic Example 1 (C).

$^1$H-NMR (CDCl$_3$, 400 MHz) δ; 2.48(s,3H), 2.55(s,3H), 3.93(s,3H), 6.72–6.77(m,2H), 6.83(s,1H), 6,93(d,1H,J=6.8 Hz), 6.97(d,1H,J=6.8 Hz), 7.63(d,2H,J=8.4 Hz), 8.07(d,2H, J=8.4 Hz), 9.00(brs,1H).

(C) 4-{2-[5-(4,7-Dimethylbenzofuran-2-yl)pyrrolyl]}benzoic acid

The title compound was obtained in the same manner as in Synthetic Example 1 (D).

$^1$H-NMR (DMSO-d$_6$, 400 MHz) δ; 2.43(s,3H), 2.46(s, 3H), 6.71(t,1H,J=2.4 Hz), 6.84(t,1H,J=2.4 Hz), 6.92(d,1H, J=7.2 Hz), 6.96(d,1H,J=7.2 Hz), 7.23(s,1H), 7.89(d,2H,J= 8.4 Hz), 7.95(d,2H,J=8.4 Hz), 11.81(brs.1H), 12.85(brs,1H).

Synthetic Example 14

4-{2-[5-(4,7-Dichlorobenzofuran-2-yl) pyrrolyl]}benzoic acid

The title compound was obtained in the same manner as in Synthetic Example 1.

$^1$H-NMR (DMSO-d$_6$, 400 MHz) δ; 6.83(t,1H,J=2.4 Hz), 6.89(t,1H,J=2.4 Hz), 7.35(d,1H,J=7.2 Hz), 7.38(d,1H,J=7.2 Hz), 7.39(s,1H), 7.91(d,2H,J=8.4 Hz), 7.97(d,2H,J=8.4 Hz), 12.02(brs,1H), 12.86(brs,1H).

Synthetic Example 15

4-{2-[5-(7-Chlorobenzofuran-2-yl)pyrrolyl]}benzoic acid

The title compound was obtained in the same manner as in Synthetic Example 1.

$^1$H-NMR (DMSO-d$_6$, 400 MHz) δ; 6.76(t,1H,J=3.2 Hz), 6.86(t,1H,J=3.2 Hz), 7.23(t,1H,J=7.6 Hz), 7.29(s,1H), 7.33 (dd,1H,J=0.8, 7.6 Hz), 7.61(dd,1H,J=0.8, 7.6 Hz), 7.90(d, 2H,J=8.4 Hz), 7.95(d,2H,J=8.4 Hz), 11.96(s,1H), 12.83(brs, 1H).

Synthetic Example 16

4-{2-[5-(7-n-Propylbenzofuran-2-yl)pyrrolyl]}benzoic acid

The title compound was obtained in the same manner as in Synthetic Example 1.

$^1$H-NMR (DMSO-d$_6$, 400 MHz) δ; 0.95(t,3H,J=7.2 Hz), 1.75(sect,2H,J=7.2 Hz), 2.87(t,2H,J=7.2 Hz), 6.71(t,1H,J= 3.2 Hz), 6.84(t,1H,J=3.2 Hz), 7.06(dd,1H,J=1.2,7.6 Hz), 7.13(t,1H,J=7.6 Hz), 7.17(s,1H), 7.44(dd,1H,J=1.2,7.6 Hz), 7.88(d,2H,J=8.4 Hz), 7.95(d,2H,J=8.4 Hz), 11.82(s,1H), 12.80(brs,1H).

Synthetic Example 17

4-{2-[5-(4-Methyl-7-ethylbenzofuran-2-yl)pyrrolyl]}benzoic acid

The title compound was obtained in the same manner as in Synthetic Example 1.

$^1$H-NMR (DMSO-d$_6$, 400 MHz) δ; 1.29(t,3H,J=7.6 Hz), 2.45(s,3H), 2.88(q,2H,J=7.6 Hz), 6.70(m,1H), 6.83(m,1H), 6.95(d,1H,J=7.2 Hz), 6.98(d,1H,J=7.2 Hz), 7.23(s,1H), 7.89 (d,2H,J=8.8 Hz), 7.94(d,2H,J=8.8 Hz), 11.80(s,1H), 12.82 (brs,1H).

Snythetic Example 18

4-{2-[5-(4-Methyl-7-7-n-propylbenzofuran-2-yl) pyrrolyl]}benzoic acid

The title compound was obtained in the same manner as in Synthetic Example 1.

$^1$H-NMR (DMSO-d$_6$, 400 MHz) δ; 0.93(t,3H), J=7.6 Hz), 1.73(sect,2H,J=7.6 Hz), 2.45(s,3H), 2.83(t,2H,J=7.6 Hz), 6.70(m,1H), 6.83(m,1H), 6.94(d,1H,J=7.2 Hz), 6.95(d,1H, J=7.2 Hz), 7.22(s,1H), 7.89(d,2H,J=8.4 Hz), 7.94(d,2H,J= 8.4 Hz), 11.81(s,1H), 12.83(brs,1H).

Synthetic Example 19

4-{2-[5-(4-Chloro-7-methylbenzofuran-2-yl) pyrrolyl]}benzoic acid

The title compound was obtained in the same manner as in Synthetic Example 1.

$^1$H-NMR (DMSO-d$_6$, 400 MHz) δ; 2.48(s,3H), 6.78–6.82 (m,1H) 6.85–6.88(m,1H), 7.09(d,1H,J=7.6 Hz), 7.21(d,1H, J=7.6 Hz), 7.29(s,1H), 7.90(d,2H,J=8.4 Hz), 7.96(d,2H,J= 8.4 Hz), 11.91(brs,1H).

Synthetic Example 20

4-{2-[5-(4-Chloro-7-ethylbenzofuran-2-yl)pyrolyl]}benzoic acid

The title compound was obtained in the same manner as in Synthetic Example 1.

$^1$H-NMR (DMSO-$d_6$, 400 MHz) δ; 1.30(t,3H,J=7.5 Hz), 2.90(q,2H,J=7.5 Hz), 6.79(dd,1H,J=2.4, 3.6 Hz), 6.86(dd, 1H,J=2.4, 3.6 Hz), 7.11(d,1H,J=8.0 Hz), 7.23(d,1H,J=8.0 Hz), 7.29(s,1H), 7.89(d,2H,J=8.8 Hz), 7.95(d,2H,J=8.4 Hz), 11.90(brs,1H).

Synthetic Example 21

4-{2-[5-(4-Chloro-7-n-porpylbenzofuran-2-yl)pyrrolyl]}benzoic acid

The title compound was obtained in the same manner as in Synthetic Example 1.

$^1$H-NMR (DMSO-$d_6$, 400 MHz) δ; 0.94(t,3H,J=7.2 Hz), 1.68–1.77(m,2H), 2.86(t,2H,J=7.2 Hz), 6.77–6.80(m,1H), 6.84–6.88(m,1H), 7.09(d,1H,J=8.4 Hz), 7.22(d,1H,J=8.4 Hz), 7.28(s,1H), 7.89(d,2H,J=8.8 Hz), 7.95(d,2H,J=8.8 Hz), 11.90(brs,1H).

Synthetic Example 22

4-{2-[5-(5-Chloro-7-methylbenzofuran-2-yl)pyrrolyl]}benzoic acid

The title compound was obtained in the same manner as in Synthetic Example 1.

$^1$H-NMR (DMSO-$d_6$, 400 MHz) δ; 2.48(s,3H), 6.74–6.77 (m,1H), 6.83–6.86(m,1H), 7.10–7.13(m,1H), 7.17(s,1H), 7.52–7.54(m,1H), 7.88(d,2H,J=8.4 Hz), 7.95(d,2H,J=8.8 Hz), 11.89(brs,1H).

Synthetic Example 23

4-{2-[5-(5-Chloro-7-ethylbenzofuran-2-yl)pyrrolyl]}benzoic acid

The title compound was obtained in the same manner as in Synthetic Example 1.

$^1$H-NMR (DMSO-$d_6$, 400 MHz) δ; 1.30(t,3H,J=7.6 Hz), 2.90(q,2H,J=7.6 Hz), 6.74(dd,1H,J=1.6, 3.6 Hz), 6.84(dd, 1H,J=1.2,3.6 Hz), 7.12(s,1H), 7.17(s,1H), 7.54(s,1H), 7.89 (d,2H,J=8.4 Hz), 7.94(d,2H,J=8.4 Hz), 11.89(s,1H).

Synthetic Example 24

4-{2-[5-(5-Chloro-7-n-propylbenzofuran-2-yl)pyrrolyl]}benzoic acid

The title compound was obtained in the same manner as in Synthetic Example 1.

$^1$H-NMR (DMSO-$d_6$, 400 MHz) δ; 1.94(t,3H,J=7.6 Hz), 1.74(sect,2H,J=7.6 Hz), 2.86(t,2H,J=7.6 Hz), 6.74(m,1H), 6.84(m,1H), 7.10(d,1H,J=2.4 Hz), 7.18(s,1H), 7.54(d,1H,J= 2.4 Hz), 7.89(d,2H,J=8.4 Hz), 7.94(d,2H,J=8.4 Hz), 11.91 (s,1H).

Synthetic Example 25

4-{2-[5-(5-Fluoro-7-ethylbenzofuran-2-yl)pyrrolyl]}benzoic acid

The title compound was obtained in the same manner as in Synthetic Example 1.

$^1$H-NMR (DMSO-$d_6$, 400 MHz) δ; 1.31(t,3H,J=7.6 Hz), 2.91(q,2H,J=7.6 Hz), 6.74(t,1H,J=3.6 Hz), 6.84(t,1H,J=3.2 Hz), 6.94(dd,1H,J=2.0,10.0 Hz), 7.25(dd,1H,J=2.4, 8.8 Hz), 7.29(s,1H), 7.94(brs,4H), 12.04(brs,1H).

Synthetic Example 26

4-{2-[5-(5-Fluoro-7-n-propylbenzofuran-2-yl)pyrrolyl]}benzoic acid

The title compound was obtained in the same manner as in Synthetic Example 1.

$^1$H-NMR (DMSO-$d_6$, 400 MHz) δ; 0.95(t,3H,J=7.2 Hz), 1.74(q,2H,J=7.2 Hz), 2.86(t,2H,J=7.2 Hz), 6.73(dd,1H,J= 2.0,3.6 Hz), 6.84(dd,1H,J=2.4,3.6 Hz), 6.93(dd,1H,J=2.0, 10.4 Hz), 7.22–7.28(m,2H), 7.90–7.96(brs,4H), 12.00(s, 1H).

Synthetic Example 27

4-{2-[5-(4,7-Difluorobenzofuran-2-yl)pyrrolyl]}benzoic acid 10 g of 2,5-difluorophenol was dissolved in 120 ml dimethylformaldehyde, 21 g of potassium carbonate and 8.57 ml allyl bromide were added in this order thereto at room temperature and then the resulting mixture was stirred at 80° C. for 1 hour. After water was added to the reaction mixture, it was extracted with ethyl acetate. The organic layer was washed with brine, dried over anhydrous magnesium sulfate and then evaporated. The resulting residue was subjected to silica gel chromatography (developing solvent: 5% ethyl acetate/n-hexane) to give 13 g of 2,5-difluorophenol allyl ether as a colorless oil.

$^1$H-NMR (CDCl$_3$, 400 MHz) δ; 4.58(d,2H,J=5.2 Hz), 5.33(dd,1H,J=2.4,8.4 Hz), 5.44(dd,1H, d, J=2.4,17.2 Hz), 5.98–6.10(m,1H), 6.55–6.60(m,1H), 6.70(ddd,1H,J=3.2,6.8, 10.0 Hz), 7.01(ddd,1H,J=5.2,8.8,10.0 Hz).

13 g 2,5-difluorophenol allyl ether was dissolved in 90 ml N,N-dimethylaniline and stirred at 170° C. for 5 hours in a nitrogen stream. The reaction solution was poured into 10% aqueous hydrogen chloride solution and then extracted with ethyl acetate. The organic layer was washed with brine, dried over anhydrous magnesium sulfate and then evaporated The resulting residue was subjected to silica gel chromatography (developing solvent: 7% ethyl acetate/n-hexane) to give 7.8 g of 2-allyl-3,6-difluorophenol as a colorless oil.

$^1$H-NMR (CDCl$_3$, 400 MHz) δ; 3.44(dd,2H,J=1.2,6.0 Hz), 5.05–5.09(m,1H), 5.26–5.28(m,1H), 5.90–5.99(m,1H), 6.56(dt,1H,J=4.4,9.2 Hz), 6.91(dt,1H,J=5.2,9.2 Hz).

7.0 g 2-allyl-3,6-difluorophenol was dissolved in 100 ml dichloromethane, and after 3-chloroperbenzoic acid was added thereto at 0° C. in a nitrogen stream, the mixture was stirred at room temperature for 2 hours. After water was added to the reaction mixture, it was extracted with dichloromethane. The organic layer was washed with a saturated aqueous sodium bicarbonate and brine, dried over anhydrous magnesium sulfate and then evaporated to give 7.2 g epoxide as a crude product. The resulting 7.2 g of epoxide was dissolved in 30 ml dimethyl sulfoxide and 10 ml water, potassium hydroxide was added thereto at room temperature and then the mixture was stirred for 4 hours. Ethyl acetate was added to the reaction mixture, and the organic layer was washed with brine. It was dried over anhydrous magnesium sulfate and then evaporated, and the resulting residue was subjected to silica gel chromatography (developing solvent: 20% ethyl acetate/n-hexane) to give 1.2 g fluoro-2,3-dihydro-2-hydroxymethylbenzofuran as a colorless oil.

¹H-NMR (CDCl₃, 400 MHz) δ; 3.25(dd,1H,J=6.7,16 Hz), 3.33(dd,1H,J=8.0,16.0 Hz), 3.75–3.83(m,1H), 3.90–3.97(m, 1H), 5.04–5.13(m,1H), 6.49(ddd,1H,J=2.8,10.0,11.2 Hz), 6.87(dt,1H,J=4.4,10.0 Hz).

4,7-Difluoro-2,3-dihydro-2-hydroxymethylbenzofuran (1.2 g) was dissolved in 6 ml pyridine, then 0.73 ml acetic anhydride was added thereto at 0° C. in a nitrogen stream, and the mixture was stirred at room temperature for 17 hours. The reaction solution was poured into 10% aqueous hydrogen chloride and extracted with ethyl acetate. The organic layer was washed with brine, dried over anhydrous magnesium sulfate and then evaporated. The resulting residue was subjected to silica gel chromatography (developing solvent: 5% ethyl acetate/n-hexane) to give 750 mg 2-acetoxymethyl-4,7-difluoro-2,3-dihydrobenzofuran as a colorless oil.

¹H-NMR (CDCl₃, 400 MHz) δ; 2.17(s,3H), 3.08(dd,1H, J=7.2,15.6 Hz), 3.39(dd,1H,J=10.0,15.6 Hz), 4.28(dd,1H,J= 6.4,12 Hz), 4.36(dd,1H,J=3.6,12 Hz), 5.13–5.20(m,1H), 6.51(ddd,1H,J=2.8,10.0,10.8 Hz), 6.89(dt,1H,J=4.4,10.0 Hz).

750 mg 2-acetoxymethyl-4,7-difluoro-2,3-dihydrobenzofuran was dissolved in 15 ml carbon tetrachloride, 582 mg of N-bromosuccinic imide and 10 mg of azodiisopropylnitrile were added in this order thereto, and then the mixture was heated under reflux for 1 hour. The reaction solution was filtered through a glass filter, and then the resulting filtrate was concentrated. To the resulting oil was added ethyl acetate. The organic layer was washed with brine, dried over anhydrous magnesium sulfate and then evaporated to give 800 mg bromide as a crude product. The resulting bromide was dissolved in 6 ml tert-butyl alcohol, and 3.3 ml potassium tert-butoxide (1.0 M solution in tert-butyl alcohol) was added thereto at room temperature in a nitrogen stream and stirred at room temperature for 2 hours. Ethyl acetate was added to the reaction solution, and the organic layer was washed with brine. It was dried over anhydrous magnesium sulfate and then evaporated, and the resulting residue was subjected to silica gel chromatography (developing solvent: 10% ethyl acetateln-hexane) to give 252 mg 2-acetoxymethyl-4,7-difluorobenzofuran as a colorless oil.

¹H-NMR (CDCl₃, 400 MHz) δ; 2.14(s,3H), 5.20(s,2H), 6.84(dt,1H,J=3.2,8.8 Hz), 6.89(d,1H,J=2.4 Hz), 6.98(ddd, 1H,J=4.0,8.8 Hz).

2-Acetoxymethyl-4,7-difluorobenzofuran (252 mg) was dissolved in 5 ml methanol, 455 mg potassium carbonate was added thereto at room temperature, and the mixture was stirred for 2 hours at the same temperature. Ethyl acetate was added to the reaction solution, and the organic layer was washed with brine. It was dried over anhydrous magnesium sulfate and then evaporated, and the resulting residue was subjected to silica gel chromatography (developing solvent: 5% ethyl acetate/n-hexane) to give 161 mg 4,7-difluoro-2-hydroxybenzofuran as a colorless oil.

¹H-NMR (CDCl₃, 400 MHz) δ; 4.80(d,2H,J=4.0 Hz), 6.80(d,1H,J=2.8 Hz), 6.83(dt,1H,J=2.8,8.4 Hz), 6.95(ddd, 1H,J=4.0,8.4,10.0 Hz).

Oxazalyl chloride (0.26 ml) was added to 0.42 ml dimethyl sulfoxide and 7 ml dichloromethane at −78° C. and stirred for 3 minutes at the same temperature. 272 mg of the 4,7-difluoro-2-hydroxybenzofuran was added thereto at the same temperature and stirred for 40 minutes. After 1.2 ml triethylamine was added to the reaction mixture, the temperature was raised to room temperature, and the mixture was stirred at room temperature for 30 minutes. After water was added to the reaction mixture, it was extracted with ethyl acetate. The organic layer was washed with brine, dried over anhydrous magnesium sulfate and then evaporated. The resulting residue was subjected to silica gel chromatography (developing solvent: 5% ethyl acetate/n-hexane) to give 169 mg of 4,7-difluorobenzofuran-2-carbaldehyde as a colorless solid.

¹H-NMR (CDCl₃, 400 MHz) δ; 6.96(dt,1H,J=2.8,8.8 Hz), 7.21(ddd,1H,J=4.0,8.8,9.6 Hz), 7.66(d,1H,J=2.4 Hz), 9.92 (s,1H).

The title compound was obtained by use of the aldehyde compound in the same manner as in Example 1.

¹H-NMR (DMSO-d₆, 400 MHz) δ; 6.82(dd,1H,J=2.4,3.6 Hz), 6.86(dd,1H,J=2.4,3.6 Hz), 7.08(dd,1H,J=3.2,8.8 Hz), 7.19(dd,1H,J=3.2,8.8 Hz), 7.42(d,1H,J=2.4 Hz), 7.92(d,2H, J=8.4 Hz), 7.96(d,2H,J=8.4 Hz), 12.08(s,1H).

Synthetic Example 28

4-{2-[5-(5-Chloro-7-isopropenylbenzofuran-2-yl) pyrrolyl]}benzoic acid

The title compound was obtained in the same manner as in Synthetic Example 1.

¹H-NMR (DMSO-d₆, 400 MHz) δ; 2.25(s,3H), 5.48(s, 1H), 5.93(s,1H), 6.74(m,1H), 6.84(m,1H), 7.23(m,2H), 7.67 (m,1H), 7.88(d,2H,J=8.4 Hz), 7.94(d,2H,J=8.4 Hz), 11.96 (s,1H), 12.87(brs,1H).

Synthetic Example 29

4-{2-[5-(5-Chloro-7-isopropylbenzofuran-2-yl) pyrrolyl]}benzoic acid

The title compound was obtained in the same manner as in Synthetic Example 1.

¹H-NMR (DMSO-d₆, 400 MHz) δ; 1.34(d,6H,J=7.2 Hz), 3.44(quint,1H,J=7.2 Hz), 6.75(m,1H), 6.84(m,1H), 7.12(m, 1H), 7.18(d,1H,J=0.8 Hz), 7.54(dd,1H,J=1.2,2.0 Hz), 7.89 (d,2H,J=8.0 Hz), 7.94(d,2H,J=8.0 Hz), 11.91(s,1H), 12.88 (brs,1H).

Synthetic Example 30

4-{2-[5-(5-Methyl-7-n-propylbenzofuran-2-yl) pyrrolyl]}benzoic acid

The title compound was obtained in the same manner as in Synthetic Example 1.

¹H-NMR (DMSO-d₆, 400 MHz) δ; 0.94(t,3H,J=7.2 Hz), 1.74(sect,2H,J=7.2 Hz), 2.34(s,3H), 2.82(t,2H,J=7.2 Hz), 6.68(m,1H), 6.83(m,1H), 6.88(s,1H), 7.11(s,1H), 7.22(s, 1H), 7.88(d,2H,J=8.4 Hz), 7.94(d,2H,J=8.4 Hz), 11.81(s, 1H), 12.86(brs,1H).

Synthetic Example 31

4-{2-[5-(5-Methyl-7-isopropenylbenzofuran-2-yl) pyrrolyl]}benzoic acid

The title compound was obtained in the same manner as in Synthetic Example 1.

¹H-NMR (DMSO-d₆, 400 MHz) δ; 2.26(s,3H), 2.38(s, 3H), 5.40(s,1H), 5.88(s,1H), 6.68(m,1H), 6.83(m,1H), 7.08 (s,1H), 7.15(s,1H), 7.36(s,1H), 7.88(d,2H,J=8.4 Hz), 7.94 (d,2H,J=8.4 Hz), 11.84(s,1H), 12.83(brs,1H).

Synthetic Example 32

4-{2-[5-(5-Methyl-7-isopropylbenzofuran-2-yl) pyrrolyl]}benzoic acid

The title compound was obtained in the same manner as in Synthetic Example 1.

¹H-NMR (DMSO-d₆, 400 MHz) δ; 1.34(d,6H,J=6.8 Hz), 2.35(s,3H), 3.40(quint,1H,J=6.8 Hz), 6.68(dd,1H,J=2.4,3.6 Hz), 6.82(dd,1H,J=2.4,3.6 Hz), 6.92(s,1H), 7.10(s,1H), 7.22 (s,1H), 7.88(d,2H,J=8.8 Hz), 7.94(d,2H,J=8.8 Hz), 11.79(s, 1H), 12.82(brs,1H).

Synthetic Example 33

4-{2-[5-(5-Methyl-7-ethylbenzofuran-2-yl)pyrrolyl]}benzoic acid

The title compound was obtained in the same manner as in Synthetic Example 1.

¹H-NMR (DMSO-d₆, 400 MHz) δ; 1.30(t,3H,J=7.6 Hz), 2.35(s,3H), 2.87(q,2H,J=7.6 Hz), 6.69(m,1H), 6.83(m,1H), 6.90(s,1H), 7.11(s,1H), 7.22(s,1H), 7.88(d,2H,J=7.6 Hz), 7.94(d,2H,J=7.6 Hz), 11.81(s,1H), 12.84(brs,1H).

Synthetic Example 34

4-{2-[5-(4-Methyl-7-isopropylbenzofuran-2-yl)pyrrolyl]}benzoic acid

The title compound was obtained in the same manner as in Synthetic Example 1.

¹H-NMR (DMSO-d₆, 400 MHz) δ; 1.33(d,6H,J=6.8 Hz), 2.44(s,3H), 3.41(quint,1H,J=6.8 Hz), 6.70(m,1H), 6.84(m, 1H), 6.95(d,1H,J=7.6 Hz), 7.00(d,1H,J=7.6 Hz), 7.22(s,1H), 7.88(d,2H,J=7.6 Hz), 7.94(d,2H,J=7.6 Hz), 11.80(s,1H), 12.84(brs,1H).

Synthetic Example 35

4-{2-[5-(5-Methoxy-7-ethylbenzofuran-2-yl)pyrrolyl]}benzoic acid

The title compound was obtained in the same manner as in Synthetic Example 1.

¹H-NMR (DMSO-d₆, 400 MHz) δ; 1.30(t,3H,J=7.6 Hz), 2.87(q,1H,J=7.6 Hz), 3.77(s,3H), 6.69(m,2H), 6.83(dd,1H, J=2.4,3.6 Hz), 6.97(d,1H,J=2.4 Hz), 7.12(s,1H), 7.88(d,2H, J=8.4 Hz), 7.94(d,2H,J=8.4 Hz), 11.80(s,1H), 12.83(brs, 1H).

Synthetic Example 36

4-{2-[5-(5-Methoxy-7-n-propylbenzofuran-2-yl)pyrrolyl]}benzoic acid

The title compound was obtained in the same manner as in Synthetic Example 1.

¹H-NMR (DMSO-d₆, 400 MHz) δ; 0.94(t,3H,J=7.2 Hz), 1.74(sect,2H,J=7.6 Hz), 2.82(t,2H,J=7.6 Hz), 3.76(s,3H), 6.66(s,1H), 6.68(m,1H), 6.83(m,1H), 6.98(s,1H), 7.12(d,1H, J=1.6 Hz), 7.88(d,2H,J=8.4 Hz), 7.94(d,2H,J=8.4 Hz), 11.80 (s,1H), 12.83(brs,1H).

Synthetic Example 37

4-{2-[5-(4-Methoxy-7-ethylbenzofuran-2-yl)pyrrolyl]}benzoic acid

The title compound was obtained in the same manner as in Synthetic Example 1.

¹H-NMR (DMSO-d₆, 400 MHz) δ; 1.28(t,3H,J=7.6 Hz), 2.84(q,2H,J=7.6 Hz), 3.87(s,3H), 6.68(s,1H), 6.69(d,1H,J= 8.0 Hz), 6.82(s,1H), 7.01(d,1H,J=8.0 Hz), 7.23(s,1H), 7.87 (d,2H,J=8.0 Hz), 7.94(d,2H,J=8.0 Hz), 11.73(s,1H) , 12.80 (brs,1H).

Synthetic Example 38

4-{2-[5-(4-Methoxy-7-n-propylbenzofuran-2-yl)pyrrolyl]}benzoic acid

The title compound was obtained in the same manner as in Synthetic Example 1.

¹H-NMR (DMSO-d₆, 400 MHz) δ; 0.93(t,3H,J=7.6 Hz), 1.70(m,2H), 2.79(t,2H,J=7.6 Hz), 3.88(s,3H), 6.68(m,2H), 6.82(m,1H), 6.99(d,1H,J=8.0 Hz), 7.23(s,1H), 7.87(d,2H,J= 8.0 Hz), 7.93(d,2H,J=8.0 Hz), 11.73(s,1H), 12.68(brs,1H).

Synthetic Example 39

4-{2-[5-(Indano[4,5-b]furan-2-yl)pyrrolyl]}benzoic acid

The title compound was obtained in the same manner as in Synthetic Example 1.

¹H-NMR (DMSO-d₆, 400 MHz) δ; 2.14(quint,2H,J=7.2 Hz), 2.97(t,2H,J=7.2 Hz), 3.10(t,2H,J=7.2 Hz), 6.68(m,1H), 6.82(m,1H), 7.12(d,1H,J=7.6 Hz), 7.17(s,1H), 7.39(d,1H,J= 7.6 Hz), 7.88(d,2H,J=7.6 Hz), 7.94(d,2H,J=7.6 Hz), 11.81 (s,1H), 12.82(brs,1H).

Synthetic Example 40

4-{2-[5-(6,7-dimethylbenzofuran-2-yl)pyrrolyl]}benzoic acid

The title compound was obtained in the same manner as in Synthetic Example 1.

¹H-NMR (DMSO-d₆, 400 MHz) δ; 2.30(s,3H), 2.42(s, 3H), 6.69– 6.72(m,1H), 6.81–6.84(m,1H), 7.02(d,1H,J=8.4 Hz), 7.11(s,1H), 7.30(d,1H,J=8.4 Hz), 7.88(d,2H,J=8.4 Hz), 7.94(d,2H,J=8.4 Hz), 11.78(s,1H), 12.80(brs,1H).

Synthetic Example 41

4-{2-[5-(7-Phenoxybenzofuran-2-yl)pyrrolyl]}benzoic acid

The title compound was obtained in the same manner as in Synthetic Example 1.

¹H-NMR (DMSO-d₆, 400 MHz) δ; 6.56–6.59(m,1H), 6.79–6.84(m,2H), 7.07–7.21(m,4H), 7.25(s,1H), 7.37–7.44 (m,3H), 7.87(d,2H,J=8.4 Hz), 7.93(d,2H,J=8.4 Hz), 11.91 (s,1H), 12.82(brs,1H).

Synthetic Example 42

4-{2-[5-(4-Fluoro-7-chlorobenzofuran-2-yl)pyrrolyl]}benzoic acid

The title compound was obtained in the same manner as in Synthetic Example 1.

¹H-NMR (DMSO-d₆, 400 MHz) δ; 6.79–6.82(m,1H), 6.86–6.89(m,1H), 7.14(t,1H,J=8.8 Hz), 7.37(dd,1H,J=4.4, 8.4 HZ), 7.38(s,1H), 7.90(d,2H,J=8.4 Hz), 7.96(d,2H,J=8.4 Hz), 11.97(d,1H), 12.86(brs,1H).

Synthetic Example 43

4-{2-[5-(5-Fluoro-7-chlorobenzofuran-2-yl)pyrrolyl]}benzoic acid

The title compound was obtained in the same manner as in Synthetic Example 1.

¹H-NMR (DMSO-d₆, 400 MHz) δ; 6.76–6.80(m,1H), 6.84–6.88(m,1H), 7.29(s,1H), 7.34(dd,1H,J=2.4,8.4 Hz), 7.51(dd,1H,J=2.4,8.4 Hz), 7.90(d,2H,J=8.4 Hz), 7.96(d,2H, J=8.4 Hz), 12.00(s,1H), 12.86(brs,1H).

Synthetic Example 44

4-{2-[5-(7-Trifluoromethylbenzofuran-2-yl)pyrrolyl]}benzoic acid

The title compound was obtained in the same manner as in Synthetic Example 1.

$^1$H-NMR (DMSO-$d_6$, 400 MHz) δ; 6.72–6.75(m,1H), 6.85–6.88(m,1H), 7.35(s,1H), 7.40(t,1H,J=7.6 Hz), 7.56(d,1H,J=7.6 Hz), 7.89(d,2H,J=8.4 Hz), 7.96(d,2H,J=8.4 Hz), 11.98(s,1H), 12.83(brs,1H).

Synthetic Example 45

4-{2-[5-(5,7-Dichlorobenzofuran-2-yl)pyrrolyl]}benzoic acid

The title compound was obtained in the same manner as in Synthetic Example 1.

$^1$H-NMR (DMSO-$d_6$, 400 MHz) δ; 6.76–6.81(m,1H), 6.84–6.89(m,1H), 7.28(s,1H), 7.46(d,1H,J=2.0 Hz), 7.76(d,1H,J=2.0 Hz), 7.89(d,2H,J=8.4 Hz), 7.95(d,2H,J=8.4 Hz), 12.00(brs,1H).

Synthetic Example 46

4-{2-[5-(4,7-Dichloro-3-methylbenzofuran-2-yl)pyrrolyl]}benzoic acid

The title compound was obtained in the same manner as in Synthetic Example 1.

$^1$H-NMR (DMSO-$d_6$, 400 MHz) δ; 2.56(s,3H), 6.69–6.73(m,1H), 6.89–6.93(m,1H), 7.30(d,1H,J=8.8 Hz), 7.39(d,1H,J=8.8 Hz), 7.94(s,4H), 11.97(brs,1H), 12.82(brs,1H).

Synthetic Example 47

4-{2-[5-(3,4,7-Trimethylbenzofuran-2-yl)pyrrolyl]}benzoic acid

The title compound was obtained in the same manner as in Synthetic Example 1.

$^1$H-NMR (DMSO-$d_6$, 400 MHz) δ; 2.50(s,3H), 2.53(s,3H), 2.59(s,3H), 6.57(brs,1H), 6.82–6.88(m,2H), 6.94(d,1H,J=7.2 Hz), 7.90(s,4H), 11.70(brs,1H), 12.80(brs,1H).

Synthetic Example 48

4-{2-[5-(7-Isopropylbenzofuran-2-yl)pyrrolyl]}benzoic acid

The title compound was obtained in the same manner as in Synthetic Example 1.

$^1$H-NMR (DMSO-$d_6$, 400 MHz) δ; 1.36(d,6H,J=7.6 Hz), 3.45(quint,1H,J=7.6 Hz), 6.70–6.73(m,1H), 6.83–6.86(m,1H), 7.09–7.16(m,2H), 7.17(s,1H), 7.43(d,1H,J=7.6 Hz), 7.88(d,2H,J=8.4 Hz), 7.95(d,2H,J=8.4 Hz), 11.83(s,1H), 12.82(brs,1H).

Synthetic Example 49

4-{2-[5-(4,6-Dimethylbenzofuran-2-yl)pyrrolyl]}benzoic acid

The title compound was obtained in the same manner as in Synthetic Example 1.

$^1$H-NMR (DMSO-$d_6$, 400 MHz) δ; 2.35(s,3H), 2.43(s,3H), 6.65–6.68(m,1H), 6.81–6.84(m,1H), 6.87(brs,1H), 7.16–7.21(m,2H), 7.88(d,2H,J=8.4 Hz), 7.93(d,2H,J=8.4 Hz), 11.82(s,1H), 12.79(brs,1H).

Synthetic Example 50

4-{2-[5-(5,7-Dimethylbenzofuran-2-yl)pyrrolyl]}benzoic acid

The title compound was obtained in the same manner as in Synthetic Example 1.

$^1$H-NMR (DMSO-$d_6$, 400 MHz) δ; 2.32(s,3H), 2.45(s,3H), 6.68–6.71(m,1H), 6.80–6.83(m,1H), 6.88(d,1H,J=1.2 Hz), 7.10(s,1H), 7.20(d,1H,J=1.2 Hz), 7.86(d,2H,J=8.4 Hz), 7.93(d,2H,J=8.4 Hz), 11.78(s,1H), 12.80(brs,1H).

Synthetic Example 51

4-{2-[5-(4-Methoxy-7-mehtylbenzofuran-2-yl)pyrrolyl]}benzoic acid

The title compound was obtained in the same manner as in Synthetic Example 1.

$^1$H-NMR (DMSO-$d_6$, 400 MHz) δ; 2.41(s,3H), 3.86(s,3H), 6.66–6.70(m,2H), 6.81–6.85(m,1H), 6.99(d,1H,J=7.6 Hz), 7.24(s,1H), 7.88(d,2H,J=8.4 Hz), 7.94(d,2H,J=8.4 Hz), 11.75(s,1H), 12.80(brs,1H).

Synthetic Example 52

4-{2-[5-(7-Ethoxybenzofuran-2-yl)pyrrolyl]}benzoic acid

The title compound was obtained in the same manner as in Synthetic Example 1.

$^1$H-NMR (DMSO-$d_6$, 400 MHz) δ; 1.40(t,3H,J=7.6 Hz), 4.25(q,2H,J=7.6 Hz), 6.68–6.71(m,1H), 6.81–6.84(m,1H), 6.87(d,1H,J=7.6 Hz), 7.12(t,1H,J=7.6 Hz), 7.16–7.19(m,2H), 7.89(d,2H,J=8.4 Hz), 7.94(d,2H,J=8.4 Hz), 11.87(s,1H), 12.78(brs,1H).

Synthetic Example 53

4-{2-[5-(7-Chloro-4-methylbenzofuran-2-yl)pyrrolyl]}benzoic acid

The title compound was obtained in the same manner as in Synthetic Example 1.

$^1$H-NMR (DMSO-$d_6$, 400 MHz) δ; 6.73–6.76(m,1H), 6.84–6.87(m,1H), 7.05(d,1H,J=8.0 Hz), 7.22(d,1H,J=8.0 Hz), 7.33(s,1H), 7.90(d,2H,J=8.4 Hz), 7.95(d,2H,J=8.4 Hz), 11.93(s,1H), 12.88(brs,1H).

Synthetic Example 54

4-{2-[5-(7-Methoxybenzofuran-2-yl)pyrrolyl]}benzoic acid

The title compound was obtained in the same manner as in Synthetic Example 1.

$^1$H-NMR (DMSO-$d_6$, 400 MHz) δ; 3.93(s,3H), 6.68–6.71(m,1H), 6.81–6.84(m,1H), 6.88(dd,1H,J=1.2, 8.0 Hz), 7.14(t,1H,J=8.0 Hz), 7.18(s,1H), 7.19(dd,1H,J=1.2, 8.0 Hz), 7.89(d,2H,J=8.4 Hz), 7.94(d,2H,J=8.4 Hz), 11.87(s,1H), 12.84(brs,1H).

Synthetic Example 55

4-{2-[5-(7-Ethylbenzofuran-2-yl)pyrrolyl]}benzoic acid

The title compound was obtained in the same manner as in Synthetic Example 1.

¹H-NMR (DMSO-d₆, 400 MHz) δ; 1.30(t,3H,J=7.6 Hz), 2.90(q,2H,J=7.6 Hz), 6.70–6.73(m,1H), 6.82–6.85(m,1H), 7.08(dd,1H,J=0.8,8.0 Hz), 7.14(t,1H,J=8.0 Hz), 7.44(dd,1H, J=0.8,8.0 Hz), 7.88(d,2H,J=8.4 Hz), 7.94(d,2H,J=8.4 Hz), 11.82(s,1H), 12.83(brs,1H).

Synthetic Example 56

4-{2-[5-(7-Phenylbenzofuran-2-yl)pyrrolyl]}benzoic acid

The title compound was obtained in the same manner as in Synthetic Example 1.

¹H-NMR (DMSO-d₆, 400 MHz) δ; 6.68–6.71(m,1H), 6.83–6.86(m,1H), 7.28(s,1H), 7.32(t,1H,J=7.6 Hz), 7.40–7.48(m,2H), 7.56(t,2H,J=7.6 Hz), 7.63(d,1H,J=7.6 Hz), 7.88(d,2H,J=8.4 Hz), 7.92–7.98(m,4H), 11.90(s,1H), 12.84(brs,1H).

Synthetic Example 57

4-{2-[5-(7-Methylbenzofuran-2-yl)pyrrolyl]}benzoic acid

The title compound was obtained in the same manner as in Synthetic Example 1.

¹H-NMR (DMSO-d₆, 400 MHz) δ; 2.52(s,3H), 6.71–6.74 (m,1H), 6.83–6.86(m,1H), 7.06(d,1H, , J=7.2 Hz), 7.12(t, 1H,J=7.2 Hz), 7.18(s,1H), 7.43(d,1H,J=7.2 Hz), 7.89(d,2H, J=8.4 Hz), 7.95(d,2H,J=8.4 Hz), 11.83(s,1H), 12.82(brs, 1H).

Synthetic Example 58

4-{2-[5-(4,5-Dimethylbenzofuran-2-yl)pyrrolyl]}benzoic acid

The title compound was obtained in the same manner as in Synthetic Example 1.

¹H-NMR (DMSO-d₆, 400 MHz) δ; 2.34(s,3H), 2.46(s, 3H), 6.70(dd,1H,J=2.4,3.6 Hz), 6.83(dd,1H,J=2.4,3.6 Hz), 7.11(s,1H), 7.22(s,1H), 7.87–7.95(m,4H), 11.80(s,1H), 12.79(s,1H).

Synthetic Example 59

4-{2-[5-(4-Methylbenzofuran-2-yl)pyrrolyl]}benzoic acid

The title compound was obtained in the same manner as in Synthetic Example 1.

¹H-NMR (DMSO-d₆, 400 MHz) δ; 2.51(s,3H), 6.72–6.73 (m,1H), 6.84–6.85(m,1H), 7.06(d,1H,J=7.2 Hz), 7.12(dd, 1H,J=5.2, 5.2 Hz), 7.10(s,1H), 7.44(d,1H,J=7.6 Hz), 7.89(d, 2H,J=8.4 Hz), 7.95(d,2H,J=8.4 Hz).

Synthetic Example 60

4-{2-[5-(4-Chlorobenzofuran-2-yl)pyrrolyl]}benzoic acid

The title compound was obtained in the same manner as in Synthetic Example 1.

¹H-NMR (DMSO-d₆, 400 MHz) δ; 6.78–6.80(m,1H), 6.86–6.87(m,1H), 7.24–7.33(m,3H), 7.57(d,1H,J=8.0 Hz), 7.92(d,2H,J=8.4 Hz), 7.95(d,2H,J=8.4 Hz), 11.97(s,1H), 12.87(brs,1H).

Synthetic Example 61

4-{2-[5-(5-Chlorobenzofuran-2-yl)pyrrolyl]}benzoic acid

The title compound was obtained in the same manner as in Synthetic Example 1.

¹H-NMR (DMSO-d₆, 400 MHz) δ; 6.74–6.75(m,1H), 6.82–6.84(m,1H), 7.20(s,1H), 7.25(dd,1H,J=2.0,8.4 Hz), 7.58(d,1H,J=8.8 Hz), 7.73(d,1H,J=2.0 Hz), 7.87(brd,2H,J= 8.4 Hz), 7.94(brd,2H,J=8.4 Hz).

Synthetic Example 62

4-{2-[5-(4,7-Dimethylbenzofuran-2-yl)furyl]}benzoic acid

The title compound was obtained in the same manner as in Synthetic Example 1.

¹H-NMR (DMSO-d₆, 400 MHz) δ; 2.46(s,6H), 6.97(d, 1H,J=7.6 Hz), 7.04(d,1H,J=7.6 Hz), 7.11(d,1H,J=4.0 Hz), 7.35(d,1H,J=4.0 Hz), 7.40(s,1H), 7.95(d,2H,J=8.4 Hz), 8.01 (d,2H,J=8.4 Hz).

Synthetic Example 63

4-{2-[5-(4,7-Dimethylbenzofuran-2-yl)thienyl]}benzoic acid

The title compound was obtained in the same manner as in Synthetic Example 1.

¹H-NMR (DMSO-d₆, 400 MHz) δ; 2.42(s,6H), 6.96(d, 1H,J=7.2 Hz), 7.02(d,1H,J=7.2 Hz), 7.38(s,1H), 7.68(d,1H, J=4.0 Hz), 7.76(d,1H,J=4.0 Hz), 7.85(d,2H,J=7.6 Hz), 7.98 (d,2H,J=7.6 Hz).

Synthetic Example 64

4-{2-[5-(4,7-Dichlorobenzofuran-2-yl)furyl]}benzoic acid

The title compound was obtained in the same manner as in Synthetic Example 1.

¹H-NMR (DMSO-d₆, 400 MHz) δ; 7.30(d,1H,J=3.6 Hz), 7.38–7.42(m,2H), 7.47(d,1H,J=8.0 Hz), 7.52(s,1H), 7.97–8.03(m,4H).

Synthetic Example 65

4-{2-[5-(4,7-Dichlorobenzofuran-2-yl)thienyl]}benzoic acid

The title compound was obtained in the same manner as in Synthetic Example 1.

¹H-NMR (DMSO-d₆, 400 MHz) δ; 7.39(d,1H,J=8.0 Hz), 7.45(d,1H,J=8.0 Hz), 7.55(s,1H), 7.80(d,1H,J=4.4 Hz), 7.84–7.90(m,3H), 7.98(d,2H,J=8.4 Hz).

Synthetic Example 66

5-{2-[5-(4,7-Dimethylbenzofuran-2-yl)pyrrolyl]}thiophene-2-carboxylic acid

The title compound was obtained in the same manner as in Synthetic Example 1.

¹H-NMR (DMSO-d₆, 400 MHz) δ; 2.43(s,3H), 2.45(s, 3H), 6.62–6.65(m,1H), 6.66–6.69(m,1H), 6.92(d,1H,J=7.6 Hz), 6.96(d,1H,J=7.6 Hz), 7.19(s,1H), 7.45(d,1H,J=3.6 Hz), 7.67(d,1H,J=3.6 Hz), 11.96(brs,1H), 12.97(brs,1H).

Synthetic Example 67

4-{2-[5-(2,3,4,7-Tetramethylbenzofuran-5-yl)pyrrolyl]}benzoic acid

The title compound was obtained in the same manner as in Synthetic Example 1.

¹H-NMR (DMSO-d₆, 400 MHz) δ; 2.28(s,3H), 2.35(s,3H), 2.37(s,3H), 2.57(s,3H), 6.16(brs,1H), 6.75(brs,1H), 7.06(s,1H), 7.80(d,2H,J=8.4 Hz), 7.86(d,2H,J=8.4 Hz), 11.36(brs,1H), 12.69(brs,1H).

Synthetic Example 68

4-{2-[5-(2,3-Dimethylbenzofuran-5-yl)pyrrolyl]}benzoic acid

The title compound was obtained in the same manner as in Synthetic Example 1.

¹H-NMR (DMSO-d₆, 400 MHz) δ; 2.18(s,3H), 2.35(s,3H), 6.59(brs,1H), 6.73(brs,1H), 7.42(d,1H,J=8.2 Hz), 7.61(dd,1H,J=2.0,8.2 Hz), 7.82–7.94(m,5H), 11.36(brs,1H), 12.76(brs,1H).

Synthetic Example 69

4-{2-[5-(7-Chlorobenzothiophene-2-yl)pyrrolyl]}benzoic acid

The title compound was obtained in the same manner as in Synthetic Example 1.

¹H-NMR (DMSO-d₆, 400 MHz) δ; 6.65–6.68(m,1H), 6.80–6.83(m,1H), 7.38–7.42(m,2H), 7.76–7.82(m,1H), 7.80(s,1H), 7.89(d,2H,J=8.4 Hz), 7.94(d,2H,J=8.4 Hz), 11.87(s,1H), 12.82(brs,1H).

Synthetic Example 70

4-{2-[5-(5,7-Dimethylbenzothiophene-2-yl)pyrrolyl]}benzoic acid

The title compound was obtained in the same manner as in Synthetic Example 1.

¹H-NMR (DMSO-d₆, 400 MHz) δ; 2.36(s,3H), 2.42(s,3H), 6.54–6.56(m,1H), 6.77–6.79(m,1H), 6.96(s,1H), 7.43(s,1H), 7.71(s,1H), 7.88(d,2H,J=8.4 Hz), 7.93(d,2H,J=8.4 Hz), 11.76(s,1H), 12.76(brs,1H).

Synthetic Example 71

4-{2-[5-(7-n-Propylbenzothiophene-2-yl)pyrrolyl]}benzoic acid

The title compound was obtained in the same manner as in Synthetic Example 1.

¹H-NMR (DMSO-d₆, 400 MHz) δ; 0.96(t,3H,J=7.2 Hz), 1.75(sect,2H,J=7.2 Hz), 2.78(t,2H,J=7.2 Hz), 6.56–6.59(m,1H), 6.78–6.81(m,1H), 7.13(d,1H,J=7.2 Hz), 7.30(t,1H,J=7.2 Hz), 7.63(d,1H,J=7.2 Hz), 7.78(s,1H), 7.89(d,2H,J=8.4 Hz), 7.93(d,2H,J=8.4 Hz), 11.77(s,1H), 12.78(brs,1H).

Synthetic Example 72

4-{2-[5-(5-Fluoro-7-methylbenzothiophene-2-yl)pyrrolyl]}benzoic acid

The title compound was obtained in the same manner as in Synthetic Example 1.

¹H-NMR (DMSO-d₆, 400 MHz) δ; 3.32(s,3H), 6.59–6.62(m,1H), 6.79–6.82(m,1H), 7.05(dd,1H,J=2.4, 9.0 Hz), 7.48(dd,1H,J=2.4, 9.0 Hz), 7.77(s,1H), 7.89(d,2H,J=8.4 Hz), 7.94(d,2H,J=8.4 Hz), 11.85(s,1H), 12.78(brs,1H).

Synthetic Example 73

4-{2-[5-(5-Chloro-7-methylbenzothiophene-2-yl)pyrrolyl]}benzoic acid

The title compound was obtained in the same manner as in Synthetic Example 1.

¹H-NMR (DMSO-d₆, 400 MHz) δ; 3.30(s,3H), 6.60–6.62(m,1H), 6.79–6.82(m,1H), 7.19(d,1H,J=1.6 Hz), 7.73(d,1H,J=1.6 Hz), 7.75(s,1H), 7.88(d,2H,J=8.4 Hz), 7.94(d,2H,J=8.4 Hz), 11.86(s,1H), 12.80(brs,1H).

Synthetic Example 74

5-{2-[5-(7-Ethylbenzothiophene-2-yl)pyrrolyl]}benzoic acid

The title compound was obtained in the same manner as in Synthetic Example 1.

¹H-NMR (DMSO-d₆, 400 MHz) δ; 1.32(t,3H,J=7.6 Hz), 2.82(q,2H,J=7.6 Hz), 6.57–6.59(m,1H), 6.78–6.81(m,1H), 7.15(d,1H,J=7.6 Hz), 7.31(t,1H,J=7.6 Hz), 7.64(d,1H,J=7.6 Hz), 7.79(s,1H), 7.89(d,2H,J=8.4 Hz), 7.94(d,2H,J=8.4 Hz), 11.78(s,1H), 12.83(brs,1H).

Synthetic Example 75

4-{2-[5-(7-Chloro-4-methylbenzothiophene-2-yl)pyrrolyl]}benzoic acid

The title compound was obtained in the same manner as in Synthetic Example 1.

¹H-NMR (DMSO-d₆, 400 MHz) δ; 2.56(s,3H), 6.65–6.67(m,1H), 6.80–6.83(m,1H), 7.20(d,1H,J=7.6 Hz), 7.29(d,1H,J=7.6 Hz), 7.89(d,2H,J=8.4 Hz), 7.93(s,1H), 7.95(d,2H,J=8.4 Hz), 11.83(s,1H), 12.82(brs,1H).

Synthetic Example 76

4-{2-[5-(7-Isopropylbenzothiophene-2-yl)pyrrolyl]}benzoic acid

The title compound was obtained in the same manner as in Synthetic Example 1.

¹H-NMR (DMSO-d₆, 400 MHz) δ; 1.33(d,6H,J=7.6 Hz), 3.10(quint,1H,J=7.6 Hz), 6.56–6.59(m,1H), 6.78–6.81(m,1H), 7.20(d,1H,J=7.6 Hz), 7.33(t,1H,J=7.6 Hz), 7.63(d,1H,J=7.6 Hz), 7.78(s,1H), 7.89(d,2H,J=8.4 Hz), 7.94(d,2H,J=8.4 Hz), 11.78(s,1H) 12.82(brs,1H).

Synthetic Example 77

4-{2-[5-(4,7-Dimethylbenzothiophene-2-yl)pyrrolyl]}benzoic acid

The title compound was obtained in the same manner as in Synthetic Example 1.

¹H-NMR (DMSO-d₆, 400 MHz) δ; 2.42(s,3H), 2.54(s,3H), 6.56–6.59(m,1H), 6.78–6.81(m,1H), 7.02(d,1H,J=6.8 Hz), 7.08(d,1H,J=6.8 Hz), 7.89(s,1H), 7.90(d,2H,J=8.4 Hz), 7.94(d,2H,J=8.4 Hz), 11.76(s,1H), 12.83(brs,1H).

Synthetic Example 78

4-{2-[5-(4,7-Dichlorobenzothiophene-2-yl)pyrrolyl]}benzoic acid

The title compound was obtained in the same manner as in Synthetic Example 1.

¹H-NMR (DMSO-d₆, 400 MHz) δ; 6.73–6.76(m,1H), 6.82–6.85(m,1H), 7.41(d,1H,J=8.0 Hz), 7.49(d,1H,J=8.0 Hz), 7.91(d,2H,J=8.4 Hz), 7.96(d,2H,J=8.4 Hz), 7.98(s,1H) 11.98(s,1H), 12.86(brs,1H).

Synthetic Example 79

4-{2-[5-(3,4,7-Trimethylbenzothiophene-2-yl)pyrrolyl]}benzoic acid

The title compound was obtained in the same manner as in Synthetic Example 1.

¹H-NMR (DMSO-d₆, 400 MHz) δ; 2.40(s,3H), 2.66(s,3H), 2.72(s,3H), 6.38–6.41(m,1H), 6.79–6.82(m,1H), 6.94–7.10(m,2H), 7.78–7.96(m,4H), 11.65(s,1H).

Synthetic Example 80

4-{2-[5-(8-Methoxymethylnaphthalene-2-yl)pyrrolyl]}benzoic acid

The title compound was obtained in the same manner as in Synthetic Example 1.

¹H-NMR (DMSO-d₆, 400 MHz) δ; 3.41(s,3H), 4.97(s,2H), 6.81(m,1H), 6.83(m,1H), 7.40(t,1H,J=7.6 Hz), 7.50(d,1H,J=6.8 Hz), 7.81(d,1H,J=8.0 Hz), 7.90–7.97(m,6H), 8.34(s,1H), 11.63(s,1H), 12.83(brs,1H).

Synthetic Example 81

4-{2-[5-(8-Ethoxynaphthalene-2-yl)pyrrolyl]}benzoic acid

The title compound was obtained in the same manner as in Synthetic Example 1.

¹H-NMR (DMSO-d₆, 400 MHz) δ; 1.51(t,3H,J=6.8 Hz), 4.26(q,2H,J=6.8 Hz), 6.73(m,1H), 6.83(m,1H), 6.95(d,1H,J=7.6 Hz), 7.34(t,1H,J=8.0 Hz), 7.41(d,1H,J=8.0 Hz), 7.86(d,1H,J=8.8 Hz), 7.92–7.95(m,5H), 8.48(s,1H), 11.70(s,1H).

Synthetic Eample 82

4-{2-[5-(8-Isopropoxynaphthalene-2-yl)pyrrolyl]}benzoic acid

The title compound was obtained in the same manner as in Synthetic Example 1.

¹H-NMR (DMSO-d₆, 400 MHz) δ; 1.43(d,6H,J=6.0 Hz), 4.82(quint,1H,J=6.0 Hz), 6.71(m,1H), 6.82(m,1H), 7.33(t,1H,J=8.0 Hz), 7.39(d,1H,J=7.6 Hz), 7.85(d,1H,J=8.8 Hz), 7.93(m,5H), 8.44(s,1H), 11.70(s,1H).

Synthetic Example 83

4-{2-[5-(8-Methoxynaphthalene-2-yl)pyrrolyl]}benzoic acid

The title compound was obtained in the same manner as in Synthetic Example 1.

¹H-NMR (DMSO-d₆, 400 MHz) δ; 4.01(s,3H), 6.76(m,1H), 6.82(m,1H), 6.97(d,1H,J=7.6 Hz), 7.36(t,1H,J=8.0 Hz), 7.42(d,1H,J=8.0 Hz), 7.85(d,1H,J=8.8 Hz), 7.90–7.96(m,5H), 8.55(s,1H), 11.69(s,1H).

Synthetic Example 84

4-{2-[5-(8-(2-Furyl)naphthalene-2-yl)pyrrolyl]}benzoic acid

The title compound was obtained in the same manner as in Synthetic Example 1.

¹H-NMR (DMSO-d₆, 400 MHz) δ; 6.72(dd,1H,J=2.0,3.6 Hz), 6.75(dd,1H,J=1.6,3.2 Hz), 6.83(dd,1H,J=2.0,3.6 Hz), 7.05(d,1H,J=3.2 Hz), 7.50(t,1H,J=8.0 Hz), 7.74(dd,1H,J=1.2,7.2 Hz), 7.88–7.94(m,5H), 8.01(s,2H), 8.62(s,1H), 11.70(s,1H).

Synthetic Example 85

4-{2-[5-(7-Hydroxy-8-isopropenylnaphthalene-2-yl)pyrrolyl]}benzoic acid

The title compound was obtained in the same manner as in Synthetic Example 1.

¹H-NMR (DMSO-d₆, 400 MHz) δ; 2.10(s,3H), 4.89(m,1H), 5.49(m,1H), 6.61(dd,1H,J=2.4,4.0 Hz), 6.79(dd,1H,J=2.4,3.6 Hz), 7.09(dd,1H,J=2.0,8.4 Hz), 7.64(d,1H,J=9.2 Hz), 7.71(d,1H,J=8.8 Hz), 7.89(d,2H,J=8.4 Hz), 7.92(d,2H,J=8.4 Hz), 8.01(s,1H), 9.40(s,1H), 11.66(s,1H).

Synthetic Example 86

4-{2-[5-(8-(1-Methoxyethyl)naphthalene-2-yl)pyrrolyl]}benzoic acid

The title compound was obtained in the same manner as in Synthetic Example 1.

¹H-NMR (DMSO-d₆, 400 MHz) δ; 1.50(d,3H,J=6.0 Hz), 3.24(s,3H), 5.32(q,1H,J=6.4 Hz), 6.82(s,2H), 7.45(t,1H,J=7.6 Hz), 7.53(d,1H,J=6.8 Hz), 7.78(d,1H,J=7.6 Hz), 7.89–7.97(m,6H), 8.41(s,1H), 11.58(s,1H).

Synthetic Example 87

4-{2-[5-(8-(2-Thienyl)naphthalene-2-yl)pyrrolyl]}benzoic acid

The title compound was obtained in the same manner as in Synthetic Example 1.

¹H-NMR (DMSO-d₆, 400 MHz) δ; 6.62(m,1H), 6.81(m,1H), 7.29(m,1H), 7.45(m,1H), 7.49(t,1H,J=7.6 Hz), 7.57(d,1H,J=7.2 Hz), 7.73(m,1H), 7.85–7.94(m,5H), 8.03(s,2H), 8.47(s,1H), 11.66(s,1H).

Synthetic Example 88

4-{2-[5-(5-Methoxy-8-isopropenylnaphthalene-2-yl)pyrrolyl]}benzoic acid

The title compound was obtained in the same manner as in Synthetic Example 1.

¹H-NMR (DMSO-d₆, 400 MHz) δ; 2.20(s,3H), 3.96(s,3H), 5.04(s,1H), 5.42(s,1H), 6.70(m,1H), 6.81(m,1H), 6.87(d,1H,J=8.0 Hz), 7.24(d,1H,J=8.0 Hz), 7.88–7.96(m,5H), 8.19(m,2H), 11.66(s,1H).

Synthetic Example 89

4-{2-[5-(5-Methoxy-8-isopropylnaphthalene-2-yl)pyrrolyl]}benzoic acid

The title compound was obtained in the same manner as in Synthetic Example 1.

¹H-NMR (DMSO-d₆, 400 MHz) δ; 1.33(d,6H,J=6.8 Hz), 3.85(quint,1H,J=6.8 Hz), 3.93(s,3H), 6.82(s,2H), 6.86(d,1H,J=8.0 Hz), 7.32(d,1H, LJ=8.0 Hz), 7.86–7.96(m,5H), 8.16(d,1H,J=8.4 Hz), 8.41(s,1H), 11.62(s,1H).

Synthetic Example 90

4-{2-[5-(5-Methoxy-8-ehtylnaphthalene-2-yl)pyrrolyl]}benzoic acid

The title compound was obtained in the same manner as in Synthetic Example 1.

¹H-NMR (DMSO-d₆, 400 MHz) δ; 1.31(t,3H,J=7.2 Hz), 3.09(q,2H,J=7.2 Hz), 3.93(s,3H), 6.80–6.84(m,3H), 7.25(d,1H,J=8.0 Hz), 7.88–7.96(m,5H), 8.15(d,1H,J=8.8 Hz), 8.33(s,1H).

Synthetic Example 91

4-{2-[5-(5-Methoxy-8-methylnaphthalene-2-yl)pyrrolyl]}benzoic acid

The title compound was obtained in the same manner as in Synthetic Example 1.

¹H-NMR (DMSO-d₆, 400 MHz) δ; 2.63(s,3H), 3.92(s, 3H), 6.77–6.82(m,3H), 7.24(d,1H,J=8.0 Hz), 7.86–7.95(m, 5H), 8.13(d,1H,J=8.8 Hz), 8.28(s,1H), 11.62(s,1H).

Synthetic Example 92

4-{2-[5-(7-Chloro-5-methoxybenzofuran-2-yl)pyrrolyl]}benzoic acid

The title compound was obtained in the same manner as in Synthetic Example 1.

¹H-NMR (DMSO-d₆, 400 MHz) δ; 3.80(s,3H), 6.72–6.75(m,1H), 6.84–6.86(m,1H), 6.95(d,1H,J=2.0 Hz), 7.18(d,1H,J=2.4 Hz), 7.22(s,1H), 7.89(d,2H,J=8.4 Hz), 7.95(d,2H,J=8.4 Hz), 11.94(brs,1H).

Synthetic Example 93

4-{2-[5-(7-Chloro-5-methylbenzofuran-2-yl)pyrrolyl]}benzoic acid

The title compound was obtained in the same manner as in Synthetic Example 1.

¹H-NMR (DMSO-d₆, 400 MHz) δ; 2.37(s,3H), 6.71–6.75(m,1H), 6.83–6.87(m,1H), 7.17(d,1H,J=0.4 Hz), 7.21(s,1H), 7.40(d,1H,J=0.4 Hz), 7.89(d,2H,J=8.4 Hz), 7.95(d,2H,J=8.8 Hz), 11.93(brs,1H).

Synthetic Example 94

4-{2-[5-(7-Chloro-5-ethylbenzofuran-2-yl)pyrrolyl]}benzoic acid

The title compound was obtained in the same manner as in Synthetic Example 1.

¹H-NMR (DMSO-d₆, 400 MHz) δ; 1.22(d,3H,J=7.5 Hz), 2.67(q,2H,J=7.5 Hz), 6.73(dd,1H,J=2.4,3.6 Hz), 6.85(dd, 1H,J=2.8, 3.2 Hz), 7.18–7.19(m,1H), 7.23(s,1H), 7.43–7.44(m,1H), 7.89(d,2H,J=8.4 Hz), 7.95(d,2H,J=8.8 Hz), 11.93(brs,1H).

Synthetic Example 95

4-{2-[5-(7-Chloro-4,5-dimethylbenzofuran-2-yl)pyrrolyl]}benzoic acid

The title compound was obtained in the same manner as in Synthetic Example 1.

¹H-NMR (DMSO-d₆, 400 MHz) δ; 2.29(s,3H), 2.36(s,3H), 6.70–6.74(m,1H), 6.82–6.86(m,1H), 7.15(s,1H), 7.31(s,1H), 7.89(d,2H,J=7.6 Hz), 7.95(d,2H,J=7.6 Hz), 11.91(brs,1H).

Synthetic Example 96

4-{2-[5-(5-Ethyl-7-methylbenzofuran-2-yl)pyrrolyl]}benzoic acid

The title compound was obtained in the same manner as in Synthetic Example 1.

¹H-NMR (DMSO-d₆, 400 MHz) δ; 1.21(t,3H,J=7.6 Hz), 6.63(q,2H,J=7.6 Hz), 6.67–6.72(m,1H), 6.80–6.85(m,1H), 6.88–6.93(m,1H), 7.12(s,1H), 7.22–7.26(m,1H), 7.88(d,2H, J=8.4 Hz), 7.94(d,2H,J=8.4 Hz), 11.80(brs,1H).

Synthetic Example 97

4-{2-[5-(7-Chloro-5-isopropenylbenzofuran-2-yl)pyrrolyl]}benzoic acid

The title compound was obtained in the same manner as in Synthetic Example 1.

¹H-NMR (DMSO-d₆, 400 MHz) δ; 2.16(s,3H), 5.13–5.14(m,1H), 5.47–5.48(m,1H), 6.74–6.78(m,1H), 6.84–6.88(m, 1H), 7.28(s,1H), 7.47(d,1H,J=1.6 Hz), 7.73(d,1H,J=1.6 Hz), 7.90(d,2H,J=8.4 Hz), 7.95(d,2H,J=8.8 Hz), 11.97(brs,1H).

Synthetic Example 98

4-{2-[5-(5,7-Dichloro-3-methylbenzofuran-2-yl)pyrrolyl]}benzoic acid

The title compound was obtained in the same manner as in Synthetic Example 1.

¹H-NMR (DMSO-d₆, 400 MHz) δ; 2.35(s,3H), 6.66–6.70(m,1H), 6.80–6.84(m,1H), 7.45–7.49(m,1H), 7.68–7.72(m,1H), 7.80–7.90(m,4H), 11.84(brs,1H).

Synthetic Example 99

4-{2-[5-(7-Chloro-4-ethylbenzofuran-2-yl)pyrrolyl]}benzoic acid

The title compound was obtained in the same manner as in Synthetic Example 1.

¹H-NMR (DMSO-d₆, 400 MHz) δ; 1.28(t,3H,J=7.6 Hz), 2.83(q,2H,J=7.6 Hz), 6.74–6.76(m,1H), 6.84–6.87(m,2H), 7.07(d,1H,J=8.0 Hz), 7.25(d,1H,J=8.0 Hz), 7.37(s,1H), 7.90(d,2H,J=8.4 Hz), 7.95(d,2H,J=8.4 Hz), 11.91(brs,1H).

synthetic Example 100

4-{2-[5-(4,5,7-Trimethylbenzofuran-2-yl)pyrrolyl]}benzoic acid

The title compound was obtained in the same manner as in Synthetic Example 1.

¹H-NMR (DMSO-d₆, 400 MHz) δ; 2.26(s,3H), 2.35(s,3H), 2.43(s,3H), 6.67–6.71(m,1H), 6.81–6.85(m,1H), 6.87(s,1H), 7.21(s,1H), 7.88(d,2H,J=8.4 Hz), 7.94(d,2H,J=8.0 Hz), 11.78(brs,1H).

Synthetic Example 101

4-{2-[5-(6-Chloro-7-n-propylbenzofuran-2-yl)pyrrolyl]}benzoic acid

The title compound was obtained in the same manner as in Synthetic Example 1.

¹H-NMR (DMSO-d₆, 400 MHz) δ; 0.96(t,3H,J=7.6 Hz), 1.64–1.76(m,2H), 2.95–3.03(m,2H), 6.73–6.76(m,1H), 6.83–6.87(m,1H), 7.19(s,1H), 7.26(d,1H,J=8.8 Hz), 7.47(d, 1H,J=8.8 Hz), 7.89(d,2H,J=8.0 Hz), 7.96(d,2H,J=8.4 Hz), 11.87(brs,1H).

Synthetic Example 102

4-{2-[5-(4-Chloro-7-n-butylbenzofuran-2yl)pyrrolyl]}benzoic acid

The title compound was obtained in the same manner as in Synthetic Example 1.

¹H-NMR (DMSO-d₆, 400 MHz) δ; 0.92(t,3H,J=7.6 Hz), 1.29–1.38(m,2H), 1.64–1.74(m,2H), 2.84–2.92(m,2H), 6.75–6.79(m,1H), 6.83–6.87(m,2H), 7.08(d,1H,J=7.7 Hz), 7.22(d,1H,J=7.7 Hz), 7.28(s,1H), 7.88(d,2H,J=8.8 Hz), 7.96(d,2H,J=8.8 Hz), 11.90(brs,1H).

Synthetic Example 103

4-{2-[5-(3,5-Dichloro-4,7-dimethylbenzofuran-2-yl)pyrrolyl]}benzoic acid

The title compound was obtained in the same manner as in Synthetic Example 1.

¹H-NMR (DMSO-d₆, 400 MHz) δ; 2.53(s,3H), 2.69(s,3H), 6.93(dd,1H,J=2.4, 4.0 Hz), 7.01(dd,1H,J=2.4, 4.0 Hz), 7.27(s,1H), 7.95(s,4H), 11.94(brs,1H).

Synthetic Example 104

4-{2-[5-(3-Chloro-4,7-dimethylbenzofuran-2-yl)pyrrolyl]}benzoic acid (A) Methyl 4-{2-[5-(3-chloro-4,7-dimethylbenzofuran-2-yl)pyrrolyl]}benzoate 0.30 g of methyl 4-{2-[5-(4,7-dimethylbenzofuran-2-yl)pyrrolyl]}benzoate was dissolved in 10 ml N,N-dimethylformamide, then 0.13 g of N-chlorosuccinimide was added thereto, and the mixture was stirred at room temperature for 14 hours. 30 ml ethyl acetate was added to the reaction solution, and the organic layer was washed with brine and then dried over anhydrous magnesium sulfate. After the drying agent was filtered off, the filtrate was concentrated and the resulting crude product was purified by silica gel column chromatography. The resulting solid was washed with methanol to give 0.12 g of the title compound as pale yellow crystals.

¹H-NMR (CDCl₃, 400 MHz) δ; 2.50(s,3H), 2.71(s,3H), 3.92(s,3H), 6.77–6.80(m,1H), 6.91(d,1H,J=7.6 Hz), 6.98(d,1H,J=7.6 Hz), 7.01–7.04(m,1H), 7.63(d,2H,J=8.4 Hz), 8.08(d,2H,J=8.4 Hz), 9.23(brs,1H).

(B) 4-{2-[5-(3-Chloro-4,7-dimethylbenzofuran-2-yl)pyrrolyl]}benzoic acid

The title compound was obtained in the same manner as in Synthetic Example 1 (D).

¹H-NMR (DMSO-d₆, 400 MHz) δ; 2.52(s,3H), 2.65(s,3H), 6.90–6.93(m,1H), 6.95–6.99(m,2H), 7.04–7.08(m,1H), 7.95(s,4H), 11.89(brs,1H).

Synthetic Example 105

4-{2-[5-(4,7-Diethylbenzofuran-2-yl)pyrrolyl]}benzoic acid

The title compound was obtained in the same manner as in Synthetic Example 1.

¹H-NMR (DMSO-d₆, 400 MHz) δ; 1.27(t,3H,J=7.6 Hz), 1.30(t,3H,J=7.6 Hz), 2.81(q,2H,J=7.6 Hz), 2.88(q,2H,J=7.6 Hz), 6.70(dd,1H,J=2.4,4.0 Hz), 6.83(dd,1H,J=2.8, 3.6 Hz), 6.96(d,1H,J=7.6 Hz), 7.01(d,1H,J=7.6 Hz), 7.27(s,1H), 7.88(d,2H,J=8.4 Hz), 7.94(d,2H,J=8.8 Hz), 11.78(brs,1H).

Synthetic Example 106

4-{2-[5-(5-Chloro-7-fluorobenzofuran-2-yl)pyrrolyl]}benzoic acid

The title compound was obtained in the same manner as in Synthetic Example 1.

¹H-NMR (DMSO-d₆, 400 MHz) δ; 6.75–6.84(m,2H), 7.25(s,1H), 7.33(dd,1H,J=2.4,8.8 Hz), 7.60(d,1H,J=2.4 Hz), 7.85(d,2H,J=8.4 Hz), 7.94(d,2H,J=8.4 Hz), 12.00(s,1H).

Synthetic Example 107

4-{2-[5-(7-Ethynylbenzofuran-2-yl)pyrrolyl]}benzoic acid

The title compound was obtained in the same manner as in Synthetic Example 1.

¹H-NMR (DMSO-d₆, 400 MHz) δ; 4.55(s,1H), 6.73(dd,1H,J=2.4, 4.0 Hz), 6.85(dd,1H,J=2.4,4.0 Hz), 7.23(t,1H,J=8.0 Hz), 7.26(s,1H), 7.36(dd,1H,J=4.2,8.0 Hz), 7.69(dd,1H,J=1.2, 8.0 Hz), 7.89(d,2H,J=8.4 Hz), 7.95(d,2H,J=8.4 Hz), 11.94(brs,1H).

Synthetic Example 108

4-{2-[5-(7-(2-Methoxyethyl)benzofuran-2-yl)pyrrolyl]}benzoic acid

The title compound was obtained in the same manner as in Synthetic Example 1.

¹H-NMR (DMSO-d₆, 400 MHz) δ; 3.14(t,2H,J=7.2 Hz), 3.27(s,3H), 3.70(t,2H,J=7.2 Hz), 6.73(dd,1H,J=2.4,3.6 Hz), 6.84(dd,1H,J=2.4,3.6 Hz), 7.11–7.16(m,2H), 7.18(s,1H), 7.46(dd,1H,J=2.0,6.8 Hz), 7.89(d,2H,J=8.4 Hz), 7.94(d,2H,J=8.4 Hz), 11.85(s,1H), 12.83(brs,1H).

Synthetic Example 109

4-{2-[5-(5-Fluoro-7-methylbenzofuran-2-yl)pyrrolyl]}benzoic acid

The title compound was obtained in the same manner as in Synthetic Example 1.

¹H-NMR (DMSO-d₆, 400 MHz) δ; 2.43(s,3H), 6.75(brs,1H), 6.85(brs,1H), 6.93(d,1H,J=10.0 Hz), 7.19(s,1H), 7.26(d,1H,J=6.8 Hz), 7.89(d,2H,J=8.0 Hz), 7.95(d,2H,J=8.0 Hz), 11.90(s,1H).

Synthetic Example 110

4-{2-[5-(4-Fluoro-7-methylbenzofuran-2-yl)pyrrolyl]}benzoic acid

The title compound was obtained in the same manner as in Synthetic Example 1.

¹H-NMR (DMSO-d₆, 400 MHz) δ; 2.42(s,3H), 6.72(brs,1H), 6.84(brs,1H), 7.06(t,1H,J=8.0 Hz), 7.19(s,1H), 7.44(dd,1H,J=6.0,8.0 Hz), 7.88(d,2H,J=8.0 Hz), 7.94(d,2H,J=8.0 Hz), 11.85(brs,1H).

Synthetic Example 111

4-{2-[5-(7-Bromo-4-fluorobenzofuran-2-yl)pyrrolyl]}benzoic acid

The title compound was obtained in the same manner as in Synthetic Example 1.

¹H-NMR (DMSO-d₆, 400 MHz) δ; 6.78(dd,1H,J=2.4,3.6 Hz), 6.87(dd,1H,J=2.4,3.6 Hz), 7.09(t,1H,J=9.2 Hz), 7.48(dd,1H,J=4.8,8.4 Hz), 7.49(s,1H), 7.93(d,2H,J=8.8 Hz), 7.96(d,2H,J=8.8 Hz), 12.20(brs,1H).

Synthetic Example 112

2-{2-[5-(4,7-Dimethylbenzofuran-2-yl)pyrrolyl]}pyridine-5-carboxylic acid

The title compound was obtained in the same manner as in Synthetic Example 1.

¹H-NMR (DMSO-d₆, 400 MHz) δ; 2.44(s,3H), 2.46(s,3H), 6.72–6.76(m,1H), 6.92(d,1H,J=8.0 Hz), 6.96(d,1H,J=8.0 Hz), 7.04–7.09(m,1H), 7.51(s,1H), 7.93(d,1H,J=7.6 Hz), 8.20(dd,1H,J=2.4,7.6 Hz), 9.02(d,1H,J=2.4 Hz), 12.26(brs,1H).

Synthetic Example 113

4-{2-[5-(4,6,7-Trimethylbenzofuran-2-yl)pyrrolyl]}benzoic acid

The title compound was obtained in the same manner as in Synthetic Example 1.

¹H-NMR (DMSO-d₆, 400 MHz) δ; 2.29(s,3H), 2.38(s, 3H) 2.40(s,3H), 6.69(brs,1H), 6.81–6.84(m,2H), 7.17(s,1H), 7.86–7.95(m,4H), 11.76((brs,1H), 12.82(brs,1H).

Synthetic Example 114

6-{2-[5-(4,7-Dimethylbenzofuran-2-yl)pyrrolyl]}-2-naphthoic acid

The title compound was obtained in the same manner as in Synthetic Example 1.

¹H-NMR (DMSO-d₆, 400 MHz) δ; 2.46(s,3H), 2.47(s, 3H), 6.73(brd,1H,J=3.6 Hz), 6.90(brd,1H,J=3.7 Hz), 6.92(d, 1H,J=6.8 Hz), 6.96(d,1H,J=6.8 Hz), 7.25(s,1H), 7.93(d,1H, J=8.4 Hz), 7.97(d,1H,J=8.4 Hz), 8.01(d,1H,J=8.4 Hz), 8.10 (d,1H,J=8.8 Hz), 8.35(s,1H), 8.53(s,1H), 11.88(brs,1H).

Synthetic Example 115

4-{2-[5-(4,7-Dimethylbenzofuran-2-yl)pyrrolyl]}-1-naphthoic acid

The title compound was obtained in the same manner as in Synthetic Example 1.

¹H-NMR (DMSO-d₆, 400 MHz) δ; 2.41(s,3H), 2.47(s, 3H), 6.58(t,1H,J=3.0 Hz), 6.81(t,1H,J=3.0 Hz), 6.93(ABq, 2H,J=9.0 Hz), 7.18(s,1H), 7.58–7.70(m,2H), 7.72(d,1H,J= 9.0 Hz), 8.17(d,1H,J=9.0 Hz), 8.40(d,1H,J=9.0 Hz), 8.77(d, 1H,J=9.0 Hz).

Synthetic Example 116

2,5-Dimethyl-4-{2-[5-(4,7-dimethylbenzofuran-2-yl) pyrrolyl]}benzoic acid

The title compound was obtained in the same manner as in Synthetic Example 1.

¹H-NMR (DMSO-d₆, 400 MHz) δ; 2.41(s,3H), 2.42(s, 3H), 2.47(s,3H), 2.55(s,3H), 6.48(dd,1H,J=2.5, 3.0 Hz), 6.71(dd,1H,J=2.5,3.0 Hz), 6.92(ABq, 2H,J=7.0 Hz), 7.18(s, 1H), 7.46(brs,1H), 7.75(brs,1H).

Synthetic Example 117

5-{2-[5-(4,7-Dimethylbenzofuran-2-yl)pyrrolyl]}-2-furancarboxylic acid

The title compound was obtained in the same manner as in Synthetic Example 1.

¹H-NMR (DMSO-d₆, 400 MHz) δ; 2.43(s,3H), 2.45(s, 3H), 6.58(d,1H,J=3.6 Hz), 6.79(d,1H,J=3.6 Hz), 6.87–6.96 (m,3H), 7.01–7.08(brs,1H), 7.18(s,1H).

Synthetic Example 118

3-{2-[5-(4,7-Dimethylbenzofuran-2-yl)pyrrolyl] }benzoic acid

The title compound was obtained in the same manner as in Synthetic Example 1.

¹H-NMR (DMSO-d₆, 400 MHz) δ; 2.49(s,3H), 2.57(s, 3H), 6.70(dd,1H,J=2.5,3.8 Hz), 6.74(dd,1H,J=2.5,3.8 Hz), 6.83(s,1H), 6.93(d,1H,J=7.5 Hz), 6.97(d,1H,J=7.5 Hz), 7.52 (t,1H,J=8.0 Hz), 7.83(d,1H,J=7.5 Hz), 7.96(d,1H,J=7.5 Hz), 8.28(s,1H), 9.03(brs,1H).

Synthetic Example 119

3-Bromo-4-{2-[5-(naphtho[1,2-b]furan-2-yl) pyrrolyl]}benzoic acid

The title compound was obtained in the same manner as in Synthetic Example 1.

¹H-NMR (DMSO-d₆, 400 MHz) δ; 6.86(m,2H), 7.31(s, 1H), 7.51(t,1H,J=7.6 Hz), 7.65(t,1H,J=7.8 Hz), 7.75(s,1H), 7.79(d,1H,J=8.0 Hz), 7.99(dd,1H,J=1.2,8.4 Hz), 8.02(d,1H, J=8.4 Hz), 8.19(s,1H), 8.32(d,1H,J=8.0 Hz), 11.98(brs,1H).

Synthetic Example 120

3-Bromo-4-{2-[5-(4,7-dichlorobenzofuran-2-yl) pyrrolyl]}benzoic acid

The title compound was obtained in the same manner as in Synthetic Example 1.

¹H-NMR (DMSO-d₆, 400 MHz) δ; 6.80(d,1H,J=3.6 Hz), 6.83(d,1H,J=3.6 Hz), 7.34(dd,1H,J=1.0,8.2 Hz), 7.35(s,1H), 7.37(dd,1H,J=0.6,8.6 Hz), 7.70(brd,1H,J=8.4 Hz), 7.94(brd, 1H,J=8.0 Hz), 8.16(brs,1H).

Synthetic Example 121

4-{2-[5-(3,4-Dimethylnaphthalene-1-yl)pyrrolyl] }benzoic acid

The title compound was obtained in the same manner as in Synthetic Example 1.

¹H-NMR (DMSO-d₆, 400 MHz) δ; 2.54(s,3H), 2.65(s, 3H), 6.57(dd,1H,J=2.8,2.8 Hz), 6.85(dd,1H,J=3.2,3.2 Hz), 7.43(s,1H), 7.47(dd,1H,J=7.6,7.6 Hz), 7.55(dd,1H,J=7.2,7.2 Hz), 7.62(d,1H,J=8.4 Hz), 8.11(d,4H,J=8.0 Hz), 8.68(brs, 1H).

Synthetic Example 122

4-{2-[5-(5,8-Dimethylnaphthalene-2-yl)pyrrolyl] }benzoic acid

The title compound was obtained in the same manner as in Synthetic Example 1.

¹H-NMR (DMSO-d₆, 400 MHz) δ; 2.61(s,3H), 2.67(s, 3H), 7.23(d,1H,J=7.2 Hz), 7.26(d,1H,J=7.6 Hz), 7.64(d,1H, J=4.0 Hz), 7.70(d,2H,J=8.0 Hz), 7.73(d,1H,J=3.6 Hz), 7.91 (d,3H,J=8.4 Hz), 8.06(d,1H,J=8.8 Hz), 8.21(s,1H).

Synthetic Example 123

4-{2-[5-(5,8-Dimethylnaphthalene-2-yl)furyl] }benzoic acid

The title compound was obtained in the same manner as in Synthetic Example 1.

¹H-NMR (DMSO-d₆, 400 MHz) δ; 2.61(s,3H), 2.70(s, 3H), 7.24(d,1H,J=6.8 Hz), 7.27(d,1H,J=7.2 Hz), 7.33(s,2H), 7.97(d,2H,J=8.4 Hz), 8.01(d,3H,J=8.4 Hz), 8.07(d,1H,J=8.8 Hz), 8.39(s,1H).

Synthetic Example 124

4-{2-[5-(8-Ethyl-1-methoxynaphthalene-2-yl) pyrrolyl]}benzoic acid

The title compound was obtained in the same manner as in Synthetic Example 1.

¹H-NMR (CDCl₃, 400 MHz) δ; 1.36(t,3H,J=7.2 Hz), 3.35(q,2H,J=7.6 Hz), 3.74(s,3H), 6.77–6.81(m,2H), 7.30–7.40(m,2H), 7.60–7.73(m,5H), 8.10–8.20(m,2H), 10.34(brs,1H).

Synthetic Example 125

4-{2-[5-(8Methyl-1-methoxynaphthalene-2-yl) pyrrolyl]}benzoic acid

The title compound was obtained in the same manner as in Synthetic Example 1.

¹H-NMR (CDCl₃, 400 MHz) δ; 2.97(s,3H), 3.73(s,3H), 6.76–6.80(m,2H), 7.28–7.35(m,2H), 7.61–7.72(m,5H), 8.14 (d,2H,J=8.4 Hz), 10.33(brs,1H).

Synthetic Example 126

4-{2-[5-(5-Acenaphthenyl)pyrrolyl]}benzoic acid

The title compound was obtained in the same manner as in Synthetic Example 1.

¹H-NMR (CDCl₃, 400 MHz) δ; 3.40–3.48(m,4H), 6.64–6.66(m,1H), 6.84–6.86(m,1H), 7.33–7.36(m,2H), 7.50–7.64(m,4H), 8.03(d,1H,J=8.4 Hz), 8.09–8.12(m,2H), 8.76(brs,1H).

Synthetic Example 127

4-{2-[5(5,8-Dimethyl-2H-chromen-3-yl)pyrrolyl}]benzoic acid

The title compound was obtained in the same manner as in Synthetic Example 1.

¹H-NMR (DMSO-d₆, 400 MHz) δ; 2.09(s,3H), 2.34(s, 3H), 4.95(brs,2H), 6.45–6.47(m,1H), 6.67(d,1H,J=7.6 Hz), 6.75–6.77(m,1H), 6.84(d,1H,J=7.6 Hz), 7.24(brs,1H), 7.85–7.94(m,4H).

Synthetic Example 128

4-{2-[5-(5-Isopropyl-8-methyl-2H-chromen-3-yl)pyrrolyl}]benzoic acid

The title compound was obtained in the same manner as in Synthetic Example 1.

¹H-NMR (CDCl₃, 400 MHz) δ; 1.30(d,6H,J =6.8 Hz), 3.28(hept.,1H,J=6.8 Hz), 4.99(d,2H,J=1. 2 Hz), 6.39–6.40 (m,1H), 6.71–6.73(m,1H), 6.81–6.86(m,2H), 6.99(d,1H,J= 8.0 Hz), 7.64(d,2H,J=8.4 Hz), 8.13(d,2H,J=8.4 Hz), 8.70 (brs,1H).

Synthetic Example 129

4-{2-[5-(5-Methyl-2H-chromen-3-yl)pyrrolyl}]benzoic acid

The title compound was obtained in the same manner as in Synthetic Example 1.

¹H-NMR (DMSO-d₆, 400 MHz) δ; 2.14(s,3H), 5.04(brs, 2H), 6.43–6.45(m,1H), 6.75–6.77(m,1H), 6.81(t,1H,J=7.6 Hz), 6.95(t,1H,J=8.0 Hz), 7.09(brs,1H), 7.86–7.93(m,4H), 11.39(s,1H), 12.82(brs,1H).

Synthetic Example 130

4-{2-[5-(5-Ethyl-2H-chromen-3-yl)pyrrolyl}]benzoic acid

The title compound was obtained in the same manner as in Synthetic Example 1.

¹H-NMR (DMSO-d₆, 400 MHz) δ; 1.13(t,3H,J=7.2 Hz), 2.48–2.55(m,2H), 5.02(brs,2H), 6.45(brs,1H), 6.75–7.09(m, 5H), 7.85–7.93(m,4H), 11.39(s,1H), 12.81(s,1H).

Synthetic Example 131

4-{2-[5-(5-Methoxy-2H-chromen-3-yl)pyrrolyl}]benzoic acid

The title compound was obtained in the same manner as in Synthetic Example 1.

¹H-NMR (CDCl₃, 400 MHz) δ; 3.91(s,3H), 5.00(brs,2H), 6.34(brs,1H), 6.50–6.55(m,2H), 6.70(s,1H), 6.95(s,1H), 7.08(dd,1H,J=7.2,7.2HZ), 7.62(d,2H,J=7.6 Hz), 8.11(d,2H, J=8.4 Hz), 8.77(brs,1H).

Synthetic Example 132

4-{2-[5-(8-Methoxy-7-methyl-2H-chromen-3-yl)pyrrolyl}]benzoic acid

The title compound was obtained in the same manner as in Synthetic Example 1.

¹H-NMR (CDCl₃, 400 MHz) δ; 2.16(s,3H), 3.73(s,3H), 5.01(brs,2H), 6.44(m,1H), 6.70–7.77(m,3H), 7.07(s,1H), 7.85–7.93(m,4H), 11.38(brs,1H), 12.80(brs,1H).

Synthetic Example 133

4-{2-[5-(4-Methyl-2H-chromen-6-yl)pyrrolyl}]benzoic acid

The title compound was obtained in the same manner as in Synthetic Example 1.

¹H-NMR (CDCl₃, 400 MHz) δ; 2.10(d,3H,J=1.6 Hz), 4.79(q,2H,J=1.6 Hz), 5.65(m,1H), 6.51(dd,1H,J=2.8,3.6 Hz), 6.74(dd,1H,J=2.8,3.6 Hz), 6.85(d,1H,J=8.0 Hz), 7.29–7.32(m,2H), 7.59(d.2H,J=8.8 Hz), 8.10(d,2H,J=8.4 Hz), 8.60(brs,1H).

Synthetic Example 134

4-{2-[5-(5-Bromo-8-methoxy-2H-chromen-3-yl)pyrrolyl}]benzoic acid

The title compound was obtained in the same manner as in Synthetic Example 1.

¹H-NMR (DMSO-d₆, 400 MHz) δ; 3.75(s,3H), 4.97(brs, 2H), 6.53(brs,1H), 6.79–6.82(m,2H), 7.14(d,1H,J=8.8 Hz), 7.22(brs,1H), 7.91(brs,4H), 11.65(brs,1H), 12.83(brs,1H).

Synthetic Example 135

4-{2-[5-(8-Methoxy-5-methyl-2H-chromen-3-yl)pyrrolyl}]benzoic acid

The title compound was obtained in the same manner as in Synthetic Example 1.

¹H-NMR (CDCl₃, 400 MHz) δ; 2.37(s,3H), 3.88(s,3H), 5.05(brs,2H), 6.40(brs,1H), 6.71–6.72(m,4H), 7.64(d,2H,J= 7.6 Hz), 8.12(d,2H,J=8.0 Hz), 8.68(brs,1H).

Synthetic Example 136

4-{2-[5-(5-Propyl-2H-chromen-3yl)pyrrolyl}]benzoic acid

The title compound was obtained in the same manner as in Synthetic Example 1.

¹H-NMR (CDCl₃, 400 MHz) δ; 0.97(t,3H,J=7.2 Hz), 1.63(tq, 2H,J=7.2,7.2 Hz), 2.59(t,2H,J=7.6 Hz), 5.04(s,2H), 6.36(dd,1H,J=2.4,2.4 Hz), 6.62(brs,1H), 6.86(dd,1H,J=7.6, 7.6 Hz), 6.94–7.01(m,2H), 7.61(d,2H,J=8.4 Hz), 8.11(d,2H, J=8.4 Hz), 8.63(brs,1H).

Synthetic Example 137

4-{2-[5-(5-Chloro-8-methyl-2H-chromen-3-yl)pyrrolyl}]benzoic acid

The title compound was obtained in the same manner as in Synthetic Example 1.

¹H-NMR (CDCl₃, 400 MHz) δ; 2.19(s,3H), 5.05(d,2H,J=1.2 Hz), 6.41(dd,1H,J=3.6,3.6 Hz), 6.71(dd,1H,J=3.6,3.6 Hz), 6.90(brs,3H), 7.64(d,2H,J=8.8 Hz), 8.11(d,1H,J=8.8 Hz), 8.74(brs,1H).

Synthetic Example 138

4-{2-[5-(5,7,8-Trimethyl-2H-chromen-3-yl)pyrrolyl]}benzoic acid

The title compound was obtained in the same manner as in Synthetic Example 1.

¹H-NMR (DMSO-d₆, 400 MHz) δ; 2.02(s,3H), 2.15(s,3H), 2.31(s,33H), 4.91(s,2H), 6.43(brs,1H), 6.60(s,1H), 6.75(brs,1H), 7.23(s,1H), 7.85–7.93(m,4H), 11.35(s,1H), 12.78(brs,1H).

Synthetic Example 139

4-{2-[5-(5,7-Dimethyl-2H-chromen-3-yl)pyrrolyl]}benzoic acid

The title compound was obtained in the same manner as in Synthetic Example 1.

¹H-NMR (DMSO-d₆, 400 MHz) δ; 2.19(s,3H), 2.34(s,3H), 4.90(s,2H), 6.43(dd,1H,J=3.2,3.2 Hz), 6.49(brs,1H), 6.60(brs,1H), 6.75(dd,1H,J=3.2,3.2 Hz), 7.23(brs,1H), 7.86(d,2H,J=8.4 Hz), 7.93(d,2H,J=8.8 Hz).

Synthetic Example 140

4-{2-[5-(7,8-Dimethyl-2H-chromen-3-yl)pyrrolyl]}benzoic acid

The title compound was obtained in the same manner as in Synthetic Example 1.

¹H-NMR (DMSO-d₆, 400 MHz) δ; 2.07(s,3H), 2.19(s,3H), 5.00(s,2H), 6.41–6.43(m,1H), 6.72–6.76(m,2H), 6.84(d,1H,J=7.6 Hz), 7.06(brs,1H), 7.86(d,2H,J=8.4 Hz), 7.91(d,2H,J=8.8 Hz).

Synthetic Example 141

4-{2-[5-(6-Methyl-2H-chromen-3-yl)pyrrolyl]}benzoic acid

The title compound was obtained in the same manner as in Synthetic Example 1.

¹H-NMR (DMSO-d₆, 400 MHz) δ; 2.22(s,3H), 4.97(s,2H), 6.44(dd,1H,J=2.0,2.0 Hz), 6.70(d,1H,J=7.6 Hz), 6.76(dd,1H,J=2.0,2.0 Hz), 6.87–6.89(m,2H), 7.06(s,1H), 7.85–7.93(m,4H), 11.39(s,1H), 12.79(brs,1H).

Synthetic Example 142

4-{2-[5-(5,6-Dimethyl-2H-chromen-3-yl)pyrrolyl]}benzoic acid

The title compound was obtained in the same manner as in Synthetic Example 1.

¹H-NMR (DMSO-d₆, 400 MHz) δ; 2.10(s,3H), 2.19(s,3H), 4.99(s,2H), 6.44(s,1H), 6.73(s,1H), 6.77(brs,2H), 7.04(s,1H), 7.86–7.93(m,4H), 11.38(s,1H), 12.78(brs,1H).

Synthetic Example 143

4-{2-[5-(6-Chloro-2H-chromen-3-yl)pyrrolyl]}benzoic acid

The title compound was obtained in the same manner as in Synthetic Example 1.

¹H-NMR (DMSO-d₆, 400 MHz) δ; 5.05(s,2H), 6.46–6.52(m,1H), 6.74–6.79(m,1H), 6.83(d,1H,J=8.8 Hz), 7.05–7.10(m,3H), 7.86(d,2H,J=8.4 Hz), 7.92(d,2H,J=8.0 Hz), 11.47(s,1H), 12.80(brs,1H).

Synthetic Example 144

4-{2-[5-(7-Chloro-2H-chromen-3-yl)pyrrolyl]}benzoic acid

The title compound was obtained in the same manner as in Synthetic Example 1.

¹H-NMR (DMSO-d₆, 400 MHz) δ; 5.06(s,2H), 6.47(dd,1H,J=2.4,3.2 Hz), 6.77(dd,1H,J=2.4,3.2 Hz), 6.91(d,1H,J=2.0 Hz), 6.96(dd,1H,J=2.0,8.0 Hz), 7.10(d,1H,J=8.0 Hz), 7.10(s,1H), 7.87(d,2H,J=8.4 Hz), 7.92(d,2H,J=8.8 Hz), 11.44(s,1H), 12.81(brs,1H).

Synthetic Example 145

4-{2-[5-(5,6,7-Trimethyl-2H-chromen-3-yl)pyrrolyl]}benzoic acid

The title compound was obtained in the same manner as in Synthetic Example 1.

¹H-NMR (DMSO-d₆, 400 MHz) δ; 2.08(s,2H), 2.18(s,3H), 2.31(s,3H), 4.83(s,2H), 6.43(dd,1H,J=2.8,2.8 Hz), 6.53(s,1H), 6.75(dd,1H,J=3.2,3.2 Hz), 7.86(d,2H,J=8.4 Hz), 7.93(d,2H,J=8.0 Hz), 11.36(s,1H), 12.78(brs,1H).

Synthetic Example 146

4-{2-[5-(5,6,8-Trimethyl-2H-chromen-3-yl)pyrrolyl]}benzoic acid

The title compound was obtained in the same manner as in Synthetic Example 1.

¹H-NMR (DMSO-d₆, 400 MHz) δ; 2.07(s,3H), 2.14(s,3H), 2.26(s,3H), 4.88(s,2H), 6.46(dd,1H,J=2.4,2.4 Hz), 6.75–6.77(m,2H), 7.33(s,1H), 7.87(d,2H,J=8.8 Hz), 7.93(d,2H,J=8.4 Hz), 11.39(s,1H), 12.78(brs,1H).

Synthetic Example 147

4-{2-[5-(5-Chloro-2H-chromen-3-yl)pyrrolyl]}benzoic acid

The title compound was obtained in the same manner as in Synthetic Example 1.

¹H-NMR (DMSO-d₆, 400 MHz) δ; 5.04(brs,2H), 6.54(dd,1H,J=2.8,2.8 Hz), 6.29(dd,1H,J-2.8,2.8 Hz), 6.82(d,1H,J=8.4 Hz), 7.02–7.10(m,2H), 7.37(brs,1H), 7.90–7.95(m,4H), 11.63(s,1H), 12.81(brs,1H).

Synthetic Example 148

4-{2-[5-(8-Methyl-2H-chromen-3-yl)pyrrolyl]}benzoic acid

The title compound was obtained in the same manner as in Synthetic Example 1.

¹H-NMR (CDCl₃, 400 MHz) δ; 2.13(brs,2H), 5.03(brs,2H), 6.43–6.45(m,1H), 6.75–6.77(m,1H), 6.81(dd,1H,J=7.2,7.2 Hz), 6.92–6.96(m,2H), 7.08(brs,1H), 7.85–7.93(m,4H).

Synthetic Example 149

4-{2-[5-(8-Trifluoromethyl-2H-chromen-3-yl)pyrrolyl]}benzoic acid

The title compound was obtained in the same manner as in Synthetic Example 1.

¹H-NMR (DMSO-d₆, 400 MHz) δ; 5.17(s,2H), 6.53(brs, 1H), 6.79(brs,1H), 7.07(dd,1H,J=7.6, 7.6 Hz), 7.16(s,1H), 7.36–7.38(m,2H), 7.86–7.94(m,4H), 11.49(s,1H), 12.80(brs, 1H).

Synthetic Example 150

4-{2-[5-(3-Fluoro-4,7-dimethylbenzofuran-2-yl)pyrrolyl]}benzoic acid (A) Methyl 4-{2-[5-(3-fluoro-4,7-dimethylbenzofuran-2-yl)pyrrolyl]}benzoate 0.20 g of methyl 4-{2-[5-(4,7-dimethylbenzofuran-2-yl)pyrrolyl]}benzoate was dissolved in 5 ml anhydrous tetrahydrofuran, then 0.20 g of N-fluoro-3,5-dichloropyridinium triflate was added thereto, and the mixture was stirred at room temperature for 30 minutes. The reaction solution was poured into a cold aqueous saturated sodium bicarbonate solution, 50 ml ethyl acetate was added thereto, and the organic layer was washed with brine and then dried over anhydrous magnesium sulfate. After the drying agent was filtered off, the filtrate was concentrated and the resulting crude product was purified by silica gel column chromatography to give 0.05 g of the title compound as pale yellow crystals.

¹H-NMR (CDCl₃, 400 MHz) δ; 2.48(s,3H), 2.60(s,3H), 3.94(s,3H), 6.75–6.79(m,2H), 6.92(d,1H,J=7.6 Hz), 6.99(d,1H,J=7.6 Hz), 7.62(d,2H,J=8.4 Hz), 8.07(d,2H,J=8.4 Hz), 8.92(brs,1H).

(B) 4-{2-[5-(3-Fluoro-4,7-dimethylbenzofuran-2-yl)pyrrolyl]}benzoic acid

The title compound was obtained in the same manner as in Synthetic Example 1 (D).

¹H-NMR (DMSO-d₆, 400 MHz) δ; 2.45(s,3H), 2.53(s, 3H), 6.63–6.66(m,1H), 6.89–6.92(m,1H), 6.98(d,1H,J=7.2 Hz), 7.06(d,1H,J=7.2 Hz), 7.93(s,4H), 11.87(s,1H), 12.83(brs,1H).

Synthetic Example 151

4-{2-[5-(3-Bromo-4,7-dimethylbenzofuran-2-yl)pyrrolyl]}benzoic acid (A) Methyl 4-{2-[5-(3-bromo-4,7-dimethylbenzofuran-2-yl)pyrrolyl]}benzoate The title compound was produced in the same manner as for the 3-chloro compound by use of N-bromosuccinimide in place of N-chlorosuccinimide.

¹H-NMR (CDCl₃, 400 MHz) δ; 2.50(s,3H), 2.73(s,3H), 3.93(s,3H), 6.77–6.80(m,1H), 6.91(d,1H,J=7.6 Hz), 6.98(d, 1H,J=7.6 Hz), 7.11–7.14(m,1H), 7.63(d,2H,J=8.4 Hz), 8.08 (d,2H,J=8.4 Hz), 9.38(brs,1H).

(B) 4-{2-[5-(3-Bromo-4,7-dimethylbenzofuran-2-yl)pyrrolyl]}benzoic acid

The title compound was obtained in the same manner as in Synthetic Example 1 (D).

¹H-NMR (DMSO-d₆, 400 MHz) δ; 2.50(s,3H), 2.67(s, 3H), 6.88–6.91(m,1H), 6.96(d,1H,J=7.2 Hz), 7.03–7.07(m, 2H), 7.92(s,4H), 11.86(s,1H), 12.83(brs,1H).

Synthetic Example 152

4-{2-[5-(6,7-Dichlorobenzofuran-2-yl)pyrrolyl]}benzoic acid

The title compound was obtained in the same manner.

¹H-NMR (DMSO-d₆, 400 MHz) δ; 6.76–6.79(m,1H), 6.85–6.88(m,1H), 7.30(s,1H), 7.47(d,1H,J=8.4 Hz), 7.64(d, 1H,J=8.4 Hz), 7.89(d,2H,J=8.4 Hz), 7.96(d,2H,J=8.4 Hz), 11.98(s,1H), 12.85(brs,1H).

Synthetic Example 153

4-{2-[5-(3-Chloro-5,7-dimethylbenzofuran-2-yl)pyrrolyl]}benzoic acid

The title compound was obtained in the same manner as in Synthetic Example 1.

¹H-NMR (DMSO-d₆, 400 MHz) δ; 2.37(s,3H), 2.51(s, 3H), 6.90–6.97(m,2H), 7.02(brs,1H), 7.16(brs,1H), 7.94(s, 4H), 11.91(s,1H), 12.85(brs,1H).

Synthetic Example 154

4-{2-[5-(3-Chloro-7-propylbenzofuran-2-yl)pyrrolyl]}benzoic acid

The title compound was obtained in the same manner as in Synthetic Example 1.

¹H-NMR (DMSO-d₆, 400 MHz) δ; 0.95(t,3H,J=7.6 Hz), 1.70–1.82(m,2H), 2.94(t,2H,J=7.6 Hz), 6.91–6.94(m,1H), 6.96–6.99(m,1H), 7.22(dd,1H,J=1.2,7.6 Hz), 7.29(t,1H,J= 7.6 Hz), 7.38(dd,1H,J=1.2,7.6 Hz), 7.93(s,4H), 11.90(s,1H), 12.89(brs,1H).

Synthetic Example 155

4-{2-[5-(3-Fluoro-5,7-dimethylbenzofuran-2-yl)pyrrolyl]}benzoic acid

The title compound was obtained in the same manner as in Synthetic Example 1.

¹H-NMR (DMSO-d₆, 400 MHz) δ; 2.35(s,3H), 2.46(s, 3H), 6.61–6.64(m,1H), 6.85–6.88(m,1H), 7.00(brs,1H), 7.22(brs,1H), 7.89(s,4H), 11.86(s,1H), 12.83(brs,1H).

Synthetic Example 156

4-{2-[5-(5-Fluoro-3,7-dimethylbenzofuran-2-yl)pyrrolyl]}benzoic acid

The title compound was obtained in the same manner as in Synthetic Example 1.

¹H-NMR (DMSO-d₆, 400 MHz) δ; 2.33(s,3H), 2.53(s, 3H), 6.64–6.67(m,1H), 6.87–6.90(m,1H), 6.95(dd,1H,J=2.0, 10.4 Hz), 7.22(dd,1H,J=2.0,10.4 Hz), 7.93(s,4H), 11.73(s, 1H), 12.84(brs,1H).

Synthetic Example 157

4-{2-[5-(5-Fluoro-4,7-dimethylbenzofuran-2-yl)pyrrolyl]}benzoic acid

The title compound was obtained in the same manner as in Synthetic Example 1.

¹H-NMR (DMSO-d₆, 400 MHz) δ; 2.34(s,3H), 2.46(s, 3H), 6.71–6.74(m,1H), 6.83–6.86(m,1H), 6.90(d,1H,J=10.8 Hz), 7.26(s,1H), 7.89(d,2H,J=8.4 Hz), 7.95(d,2H,J=8.4 Hz), 11.84(s,1H), 12.83(brs,1H).

Synthetic Example 158

4-{2-[5-(5-Fluoro-3,4,7-Trimethylbenzofuran-2yl)pyrrolyl]}benzoic acid

The title compound was obtained in the same manner as in Synthetic Example 1.

¹H-NMR (DMSO-d₆, 400 MHz) δ; 2.48(s,6H), 2.50(s, 3H), 6.59–6.62(m,1H), 6.85–6.88(m,1H), 6.92(d,1H,J=10.8 Hz), 7.92(s,4H), 11.72(s,1H), 12.80(brs,1H).

Synthetic Example 159

4-{2-[5-(3,5-Difluro-4,7-dimethylbenzofuran-2-yl)pyrrolyl]}benzoic acid

The title compound was obtained in the same manner as in Synthetic Example 1.

¹H-NMR (DMSO-d₆, 400 MHz) δ; 2.42(s,3H), 2.48(s, 3H), 6.65–6.68(m,1H), 6.89–6.92(m,1H), 7.03(d,1H,J=10.8 Hz), 7.93(s,4H), 11.91(s,1H), 12.85(brs,1H).

Synthetic Example 160

4-{2-[5-(3-Chloro-5-fluoro-4,7-(dimethylbenzofuran-2-yl)pyrrolyl]}benzoic acid

The title compound was obtained in the same manner as in Synthetic Example 1.

¹H-NMR (DMSO-d₆, 400 MHz) δ; 2.48(s,3H), 2.52(s, 3H), 6.91–6.94 (m,1H), 6.98–7.01(m,1H), 7.04(d,1H,J=10.8 Hz), 7.95(s,4H), 11.92(s,1H), 12.86(brs,1H).

Synthetic Example 161

4-{2-[5-(7-Ethoxy-5-fluoro-4-methylbenzofuran-2-yl)pyrrolyl]}benzoic acid

The title compound was obtained in the same manner as in Synthetic Example 1.

¹H-NMR (DMSO-d₆, 400 MHz) δ; 1.38(t,3H,J=7.6 Hz), 2.29(s,3H), 4.20(q,2H,J=7.6 Hz), 6.69–6.72(m,1H), 6.77(d,1H,J=10.8 Hz), 6.81–6.84(m,1H), 7.26(s,1H), 7.89(d,2H,J=8.4 Hz), 7.94(d,2H,J=8.4 Hz), 11.88(s,1H), 12.80(brs,1H).

Synthetic Example 162

4-{2-[5-(7-Ethyl-5-fluoro-4-methylbenzofuran-2-yl)pyrrolyl]}benzoic acid

The title compound was obtained in the same manner as in Synthetic Example 1.

¹H-NMR (DMSO-d₆, 400 MHz) δ; 1.27(t,3H,J=7.6 Hz), 2.34(s,3H), 2.85(q,2H,J=7.6 Hz), 6.71–6.74(m,1H), 6.83–6.86(m,1H), 6.91(d,1H,J=10.8 Hz), 7.88(d,2H,J=8.4 Hz), 7.95(d,2H,J=8.4 Hz), 11.83(s,1H), 12.86(brs,1H).

Synthetic Example 163

4-{2-[5-(7-Ethyl-3,5-difluoro-4-methylbenzofuran-2-yl)pyrrolyl]}benzoic acid

The title compound was obtained in the same manner as in Synthetic Example 1.

¹H-NMR (DMSO-d₆, 400 MHz) δ; 1.28(t,3H,J=7.6 Hz), 2.43(s,3H) 2.90(q,2H,J=7.6 Hz), 6.65–6.68(m,1H), 6.86–6.89(m,1H), 7.04(d,1H,J=11.2 Hz), 7.85–7.96(m,4H), 11.87(s,1H), 12.85(brs,1H).

Synthetic Example 164

4-{2-[5-(7-Chloro-4-fluorobenzothiophene-2-yl)pyrrolyl]}benzoic acid

The title compound was obtained in the same manner as in Synthetic Example 1.

¹H-NMR (DMSO-d₆, 400 MHz) δ; 6.71–6.74(m,1H), 6.81–6.84(m,1H), 7.27(t,1H,J=8.8 Hz), 7.42(dd,1H,J=4.4, 8.8 Hz), 7.90(d,2H,J=8.4 Hz), 7.95(d,2H,J=8.4 Hz), 11.40(s,1H), 12.81(brs,1H).

Synthetic Example 165

4-{2-[5-(3,5-Dichloro-7-methylbenzothiophene-2-yl)pyrrolyl]}benzoic acid

The title compound was obtained in the same manner as in Synthetic Example 1.

¹H-NMR (DMSO-d₆, 400 MHz) δ; 2.52(s,3H), 6.87–6.94 (m,2H), 7.38(brs,1H), 7.61(brs,1H), 7.90(s,4H), 11.81(s, 1H), 12.85(brs,1H).

Synthetic Example 166

4-{2-[5-(3-Chloro-5-fluoro-7-methylbenzothiophene-2-yl)pyrrolyl]}benzoic acid

The title compound was obtained in the same manner as in Synthetic Example 1.

¹H-NMR (DMSO-d₆, 400 MHz) δ; 2.53(s,3H), 6.88–6.94 (m,4H), 7.24(dd,1H,J=2.4,9.6 Hz), 7.40(dd,1H,J=2.4,9.6 Hz), 7.93(s,4H), 11.80(s,1H), 12.87(brs,1H).

Synthetic Example 167

4-{2-[5-(7-fluoro-4-trifluoromethylbenzofuran-2-yl)pyrrolyl]}benzoic acid

The benzofuran site was synthesized in the same manner as in Synthetic Example 27. The other was obtained in the same manner as in Synthetic Example 1.

¹H-NMR (DMSO-d₆, 400 MHz) δ; 6.87–6.92(m,2H), 7.35(dd,1H,J=10.0,10.4 Hz), 7.53(brs,1H), 7.62(dd,1H,J=3.6,8.8 Hz), 7.93(d,2H,J=8.8 Hz), 7.96(d,2H,J=8.8 Hz).

Synthetic Example 168

4-{2-[5-(3-Chloro-5-fluoro-7-methylbenzofuran-2-yl)pyrrolyl]}benzoic acid

The title compound was obtained in the same manner as in Synthetic Example 1.

¹H-NMR (DMSO-d₆, 400 MHz) δ; 2.57(s,3H), 6.91–6.94 (m,1H), 6.96–7.02(m,1H), 7.09(dd,1H,J=2.7,11.0 Hz), 7.17 (dd,1H,J=2.3,8.0 Hz), 7.95(brs,4H), 12.0(s,1H).

Synthetic Example 169

4-{2-[5-(3-Chloro-7-ethyl-5-fluorobenzofuran-2-yl)pyrrolyl]}benzoic acid

The title compound was obtained in the same manner as in Synthetic Example 1.

¹H-NMR (DMSO-d₆, 400 MHz) δ; 1.30(t,3H,J=8.0 Hz), 3.00(q,2H,J=7.2 Hz), 6.90–6.93(m,1H), 6.98–7.00(m,1H), 7.12(dd,1H,J=2.9,10.4 Hz), 7.18(dd,1H,J=2.4,8.8 Hz), 7.93 (d,2H,J=8.0 Hz), 7.96(d,2H,J=8.0 Hz), 11.96(brs,1H).

Synthetic Example 170

4-{2-[5-(3-Chloro-5-fluoro-7-propylbenzofuran-2-yl)pyrrolyl]}benzoic acid

The title compound was obtained in the same manner as in Synthetic Example 1.

¹H-NMR (DMSO-d₆, 400 MHz) δ; 0.96(t,3H,J=6.8 Hz), 1.72–1.80(m,2H), 2.96(t,2H,J=7.2 Hz), 6.90–6.93(m,1H), 6.98–7.01(m,1H), 7.10(dd,1H,J=2.0,10.4 Hz), 7.18(dd,1H, J=2.0, 7.6 Hz), 7.92(d,2H,J=8.4 Hz), 7.96(d,2H,J=8.4 Hz), 11.88(brs,1H).

Synthetic Example 171

4-{2-[5-(3-Chloro-5-fluoro-7-propylbenzofuran-2-yl)pyrrolyl]}benzoic acid

The title compound was obtained in the same manner as in Synthetic Example 1.

$^1$H-NMR (DMSO-d$_6$, 400 MHz) δ; 0.94(t,3H,J=7.0 Hz), 1.73–1.80(m,2H), 2.90–2.98(m,2H), 7.01(d,1H,J=2.8 Hz), 7.13(dd,1H,J=2.6,10.4 Hz), 7.22(dd,1H,J=2.4,8.0 Hz), 7.88 (d,2H,J=8.4 Hz), 8.05(d,2H,J=8.4 Hz).

Synthetic Example 172

4-{2-[5-(3-Bromo-5-fluoro-7-methylbenzofuran-2-yl)pyrrolyl]}benzoic acid

The title compound was obtained in the same manner as in Synthetic Example 1.

$^1$H-NMR (DMSO-d$_6$, 400 MHz) δ; 2.58(s,3H), 6.92–6.94 (m,1H), 7.06–7.16(m,3H), 7.95(brs,4H), 12.00(s,1H).

Synthetic Example 173

4-{2-[5-(7-Ethyl-5-fluoro-3-methylbenzofuran-2-yl) pyrrolyl]}benzoic acid

The title compound was obtained in the same manner as in Synthetic Example 1.

$^1$H-NMR (DMSO-d$_6$, 400 MHz) δ; 1.31(t,3H,J=7.6 Hz), 2.33(s,3H), 2.97(q,2H,J=7.6 Hz), 6.64–6.66(m,1H), 6.86–6.89(m,1H), 6.97(dd,1H,J=2.4,10.0 Hz), 7.22(dd,1H, J=2.4,8.8 Hz), 7.91(d,2H,J=8.4 Hz), 7.93(d,2H,J=8.4 Hz), 11.73(s,1H), 12.82(brs,1H).

Synthetic Example 174

4-{2-[5-(3,5-Difluoro-7-ethylbenzofuran-2-yl) pyrrolyl]}benzoic acid

The title compound was obtained in the same manner as in Synthetic Example 1.

$^1$H-NMR (DMSO-d$_6$, 400 MHz) δ; 1.32(t,3H,J=7.6 Hz), 2.96(q,2H,J=7.6 Hz), 6.68–6.71(m,1H), 6.91(dd,1H,J=2.4, 3.6 Hz), 7.10(dd,1H,J=2.4,10.4 Hz), 7.30(dd,1H,J=2.4,8.0 Hz), 7.94(brs,4H), 11.95(s,1H), 12.86(brs,1H).

Synthetic Example 175

4-{2-[5-(4-Ethyl-5-fluoro-7-methylbenzofuran-2-yl) pyrrolyl]}benzoic acid

The title compound was obtained in the same manner as in Synthetic Example 1.

$^1$H-NMR (DMSO-d$_6$, 400 MHz) δ; 1.23(t,3H,J=7.6 Hz), 2.46(s,3H), 2.79(q,4H,J=7.6 Hz), 6.72–6.75(m,1H), 6.84–6.86(m,1H), 6.90(d,1H,J=10.8 Hz), 7.30(s,1H), 7.89 (d,2H,J=8.4 Hz), 7.95(d,2H,J=8.4 Hz), 11.84(brs,1H)

Synthetic Example 176

4-{2-[5-(4,7-Diethyl-3,5-difluorobenzofuran-2-yl) pyrrolyl]}benzoic acid

The title compound was obtained in the same manner as in Synthetic Example 1.

$^1$H-NMR (DMSO-d$_6$, 400 MHz) δ; 1.23(t,3H,J=7.2 Hz), 1.30(t,3H,J=7.2 Hz), 2.82–2.88(m,2H), 2.92(q,2H,J=7.2 Hz), 6.67–6.70(m,1H), 6.90–6.92(m,1H), 7.05(d,1H,J=11.2 Hz), 7.94(s,4H), 11.90(brs,1H).

Synthetic Example 177

4-{2-[5-(3-Bromo-4,7-diethyl-5-fluorobenzofuran-2-yl)pyrrolyl]}benzoic acid

The title compound was obtained in the same manner as in Synthetic Example 1.

$^1$H-NMR (DMSO-d$_6$, 400 MHz) δ; 1.22(t,3H,J=7.6 Hz), 1.30(t,3H,J=7.6 Hz), 2.97(q,2H,J=7.6 Hz), 3.03–3.10(m, 2H), 6.90–6.92(m,1H), 7.07(d,1H,J=11.2 Hz), 7.09–7.12(m, 1H), 7.93(d,2H,J=8.4 Hz), 7.96(d,2H,J=8.4 Hz), 11.90(brs, 1H).

Synthetic Example 178

4-{2-[5-(3,5-Dichloro-7-methylbenzofuran-2-yl) pyrrolyl]}benzoic acid

The title compound was obtained in the same manner as in Synthetic Example 1.

$^1$H-NMR (DMSO-d$_6$, 400 MHz) δ; 2.58(s,3H), 6.92–6.95 (m,1H), 7.00–7.02(m,1H), 7.27–7.29(m,1H), 7.40–7.42(m, 1H), 7.96(s,4H), 12.00(s,1H).

Synthetic Example 179

4-{2-[5-(3,5-Dichloro-7-ethylbenzofuran-2-yl) pyrrolyl]}benzoic acid

The title compound was obtained in the same manner as in Synthetic Example 1.

$^1$H-NMR (DMSO-d$_6$, 400 MHz) δ; 1.33(t,3H,J=7.7 Hz), 3.00(q,2H,J=7.7 Hz), 6.94(dd,1H,J=2.8,4.0 Hz), 7.01(dd, 1H,J=2.0,3.6 Hz), 7.29(d,1H,J=2.0 Hz), 7.42(d,1H,J=1.6 Hz), 7.96(s,4H), 11.99(brs,1H)

Synthetic Example 180

4-{2-[5-(3-Fluoro-4,5,7-trimethylbenzofuran-2-yl) pyrrolyl]}benzoic acid

The title compound was obtained in the same manner as in Synthetic Example 1.

$^1$H-NMR (DMSO-d$_6$, 400 MHz) δ; 2.26(s,3H), 2.43(s, 3H), 2.45(s,3H), 6.61–6.65(m,1H), 6.88–6.90(m,1H), 6.97–7.00(m,1H), 7.93(s,4H), 11.84(brs,1H).

Synthetic Example 181

4-{2-[5-(3-Chloro-4,5,7-trimethylbenzofuran-2-yl) pyrrolyl]}benzoic acid

The title compound was obtained in the same manner as in Synthetic Example 1.

$^1$H-NMR (DMSO-d$_6$, 400 MHz) δ; 2.27(s,3H), 2.50(s, 3H), 2.57(s,3H), 6.89–6.92(m,1H), 6.94–6.97(m,1H), 6.98–7.00(m,1H), 7.94(s,4H), 11.85(brs,1H).

Synthetic Example 182

4-{2-[5-(3-Bromo-4,5,7-trimethylbenzofuran-2-yl) pyrrolyl]}benzoic acid

The title compound was obtained in the same manner as in Synthetic Example 1.

$^1$H-NMR (DMSO-d$_6$, 400 MHz) δ; 2.27(s,3H), 2.50(s, 3H), 2.61(s,3H), 6.88–6.91(m,1H), 6.98–7.00(m,1H), 7.04–7.07(m,1H), 7.94(s,4H), 11.85(brs,1H).

Synthetic Example 183

4-{2-[5-(5-Fluoro-4-methylbenzofuran-2-yl) pyrrolyl]}benzoic acid

The title compound was obtained in the same manner as in Synthetic Example 1.

¹H-NMR (DMSO-d₆, 400 MHz) δ; 2.40(s,3H), 6.72–6.75 (m,1H), 6.83–6.86(m,1H), 7.04(dd,1H,J=9.2,9.6 Hz), 7.29 (s,1H), 7.39(dd,1H,J=3.6,8.4 Hz), 7.90(d,2H,J=8.4 Hz), 7.95(d,2H,J=8.4 Hz), 11.93(brs,1H).

Synthetic Example 184

4-{2-[5-(5-Chloro-4,7-dimethylbenzofuran-2-yl)pyrrolyl]}benzoic acid

The title compound was obtained in the same manner as in Synthetic Example 1.

¹H-NMR (DMSO-d₆, 400 MHz) δ; 3.24(s,3H), 3.39(s,3H), 6.73–6.75(m,6H), 6.84–6.86(m,1H), 7.12(s,1H), 7.27 (s,1H), 7.88–7.90(d,2H,J=8.8 Hz), 7.94–7.96(d,2H,J=8.8 Hz), 11.59(brs,1H).

Synthetic Example 185

4-{2-[5-(5Chloro-3-fluoro-4,7-dimethylbenzofuran-2-yl)pyrrolyl]}benzoic acid

The title compound was obtained in the same manner as in Synthetic Example 1.

¹H-NMR (DMSO-d₆, 400 MHz) δ; 2.49(s,3H), 2.54(s,3H), 6.68–6.69(m,1H), 6.91–6.92(m,1H), 7.26(s,1H), 7.94 (s,4H), 17.59(brs,1H).

Synthetic Example 186

4-{2-[5-(3-Bromo-5-chloro-4,7dimethylbenzofuran-2-yl)pyrrolyl]}benzoic acid

The title compound was obtained in the same manner as in Synthetic Example 1.

¹H-NMR (DMSO-d₆, 400 MHz) δ; 2.53(s,3H), 2.73(s,3H), 6.91–6.92(m,1H), 7.10–7.11(m,1H), 7.27(s,1H), 7.95 (s,4H), 11.59(brs,1H).

Synthetic Example 187

4-{2-[5-(5-Chloro-3,4,7-trimethylbenzofuran-2-yl)pyrrolyl]}benzoic acid

The title compound was obtained in the same manner as in Synthetic Example 1.

¹H-NMR (DMSO-d₆, 400 MHz) δ; 2.52(s,3H), 2.62(s,3H), 3.29(s,3H), 6.61–6.62(m,1H), 6.86–6.88(m,1H), 7.15 (s,1H), 7.89–7.91(d,2H,J=8.8 Hz), 7.92–7.94(d,2H,J=8.8 Hz), 11.56(brs,1H).

Synthetic Example 188

4-{2-[5-(5-Chloro-4-methylbenzofuran-2-yl)pyrrolyl]}benzoic acid

The title compound was obtained in the same manner as in Synthetic Example 1.

¹H-NMR (DMSO-d₆, 400 MHz) δ; 2.48(s,3H), 6.75–6.76 (m,1H), 6.84–6.86(m,1H), 7.12(d,1H,J=1.2 Hz), 7.17(s,1H), 7.54(d,1H,J=1.6 Hz), 7.88–7.96(m,4H), 11.90(s,1H), 12.80 (brs,1H).

Synthetic Example 189

4-{2-[5-(7-Chloro-5-fluoro-4-propylbenzofuran-2-yl)pyrrolyl]}benzoic acid

The title compound was obtained in the same manner as in Synthetic Example 1.

¹H-NMR (DMSO-d₆, 400 MHz) δ; 0.94(t,3H,J=7.2 Hz), 1.66(q,2H,J=7.2 Hz), 2.78(t,2H,J=7.2 Hz), 6.74–6.77(m, 1H), 6.82–6.85(m,1H), 7.29(d,1H,J=10.0 Hz), 7.41(s,1H), 7.87(d,2H,J=8.4 Hz), 7.95(d,2H,J=8.4 Hz), 11.91(brs,1H).

Synthetic Example 190

4-{2-[5-(5-Fluoro-6-methylbenzofuran-2-yl)pyrrolyl]}benzoic acid

The title compound was obtained in the same manner as in Synthetic Example 1.

¹H-NMR (DMSO-d₆, 400 MHz) δ; 2.31(s,3H), 6.68–6.72 (m,1H), 6.82–6.85(m,1H), 7.15(s,1H), 7.40(d,1H,J=10.0 Hz), 7.47(d,1H,J=6.4 Hz), 7.88(d,2H,J=8.4 Hz), 7.94(d,2H, J=8.4 Hz), 11.90(brs,1H).

Synthetic Example 191

4-{2-[5-(5,7-Difluorobenzofuran-2-yl)pyrrolyl]}benzoic acid

The title compound was obtained in the same manner as in Synthetic Example 1.

¹H-NMR (DMSO-d₆, 400 MHz) δ; 6.78–6.81(m,1H), 6.85–6.88(m,1H), 7.18–7.25(m,1H), 7.29(d,1H,J=3.2 Hz), 7.37(dd,1H,J=2.4,8.4 Hz), 7.89(d,2H,J=8.4 Hz), 7.95(d,2H, J=8.8 Hz), 12.02(brs,1H).

Synthetic Example 192

4-{2-[5-(4-Ethyl-5-fluorobenzofuran-2-yl)pyrrolyl]}benzoic acid

The title compound was obtained in the same manner as in Synthetic Example 1.

¹H-NMR (DMSO-d₆, 400 MHz) δ; 1.25(t,3H,J=7.6 Hz), 2.80–2.88(m,2H), 6.72–6.75(m,1H), 6.83–6.86(m,1H), 7.00–7.06(m,1H), 7.33(s,1H), 7.38–7.42(m,1H), 7.89(d,2H, J=8.8 Hz), 7.95(d,2H,J=8.8 Hz), 11.91(brs,1H).

Synthetic Example 193

4-{2-[5-(5-Chloro-7-ehtyl-3-fluorobenzofuran-2-yl)pyrrolyl]}benzoic acid

The title compound was obtained in the same manner as in Synthetic Example 1.

¹H-NMR (DMSO-d₆, 400 MHz) δ; 1.32(t,3H,J=7.6 Hz), 2.69(q,2H,J=7.6 Hz), 6.69–6.72(m,1H), 6.90–6.93(m,1H), 7.26–7.28(m,1H), 7.54–7.57(m,1H), 7.90–7.96(m,4H), 11.95(brs,1H).

Synthetic Example 194

4-[2-{5-(5-Chloro-7-methylmethylenedioxymethylbenzofuran-2-yl)pyrrolyl}]benzoic acid The title compound was obtained in the same manner as in Synthetic Example 1.

¹H-NMR (DMSO-d₆, 400 MHz) δ; 3.36(s,3H), 4.74(s, 2H), 4.85(s,2H), 6.74–6 75(m,1H), 6.85–6.87(m,1H), 7.22 (s,1H), 7.25(d,1H,J=2 Hz), 7.69(d,1H,J=2 Hz), 7.88(d,2H, J=8.4 Hz), 7.95(d,2H,J=8.4 Hz), 11.93(brs,1H).

Synthetic Example 195

4-[2-{5-(5-Chloro-7-nitrilebenzofuran-2-yl)pyrrolyl}]benzoic acid

The title compound was obtained in the same manner as in Synthetic Example 1.

¹H-NMR (DMSO-d₆, 400 MHz) δ; 6.87–6.88(m,1H), 6.92–6.93(m,1H), 7.26(s,1H), 7.64(s,1H), 7.89(d,2H,J=8.4 Hz), 7.92(s,1H), 8.00(d,2H,J=8.4 Hz), 12.09(brs,1H).

Synthetic Example 196

4-[2-{5-(7-Chloro-4-ethyl-5-fluorobenzofuran-2-yl)pyrrolyl}]benzoic acid

The title compound was obtained in the same manner as in Synthetic Example 1.

¹H-NMR (DMSO-d₆, 400 MHz) δ; 1.22(t,3H,J=7.2 Hz), 2.81(q,2H,J=7.2 Hz), 6.76–6.79(m,1H), 6.86–6.89(m,1H), 7.30(d,1H,J=10.0 Hz), 7.42(s,1H), 7.90(d,2H,J=8.4 Hz), 7.96(d,2H,J=8.4 Hz), 11.96(s,1H), 12.84(brs,1H).

Synthetic Example 197

4-[2-{5-(3-Methoxymethyl-5,6,7,8-tetrahydro-5,5,8,8-tetramethylnaphthalene-2-yl)pyrrolyl}]benzoic acid (A) 3,4-Dihydroxymethyl-5,6,7,8-tetrahydro-5,5,8,8-tetramethylnaphthalene 7 g of aluminum chloride was added by portions to 200 ml solution of 50 g 2,5-dichloro-2,5-dimethylhexane in orthoxylene at 0° C. under stirring. After the mixture was stirred at the same temperature for 15 minutes, it was poured into ice-cold water and extracted with ethyl acetate. The organic layer was washed with brine, dried over anhydrous magnesium sulfate and then evaporated to give 60 g of 2,3,5,5,8,8-hexamethyl-5,6,7,8-tetrahydronaphthalene as a brown oil.

128 g of N-bromosuccinic acid and 300 mg of bisazoisobutyronitrile were added to 300 ml solution of 60 g of the unpurified 2,3,5,5,8,8-hexamethyl-5,6,7,8-tetrahydronaphthalene in carbon tetrachloride, and the mixture was stirred under heating at 80° C. for 2 hours. The reaction mixture was cooled to 0° C., 300 ml hexane was added thereto, and then the mixture was filtered through a glass filter. The filtrate was evaporated to give 110 g of 3,4-dibromomethyl-5,5,8,8-tetramethyl-5,6,7,8-tetrahydronaphthalene as a brown oil.

50 g of sodium carbonate was added at room temperature to a mixed solution of 400 ml water and 400 ml dioxane containing 10 g of the unpurified 3,4-dibromomethyl-5,5,8,8-tetramethyl-5,6,7,8-tetrahydronaphthalene, and the mixture was heated under reflux for 11 hours. The dioxane was removed, and then the residue was extracted with ethyl acetate. The organic layer was washed with brine, dried over anhydrous magnesium sulfate and then evaporated. The resulting residue was subjected to silica gel column chromatography to give 1.6 g of the title compound as a yellow oil.

¹H-NMR (CDCl₃, 400 MHz) δ; 1.46(s,12H), 1.68(s,4H), 3.50(brs,2H), 4.64(br s,4H), 7.24(s,4H).

(B) 2,3-(Methoxy-methylenedimethyloxy)-5,6,7,8-tetrahydro-5,5,8,8-tetramethylnaphthalene 1.8 ml trimethyl o-formate and 20 mg D-10-camphor sulfonic acid were added at room temperature to 40 ml solution of 2.1 g 3,4-dihydroxymethyl-5,6,7,8-tetrahydro-5,5,8,8-tetramethylnaphthalene in dichloromethane under stirring. The resulting mixture was stirred for 17.5 hours at the same temperature. Further, 1.8 ml trimethyl o-formate and 20 mg D-10-camphor sulfonic acid were added thereto at room temperature, and then the resulting mixture was stirred for 4 hours at the same temperature. Water was added to the reaction mixture, and then it was extracted with ethyl acetate. The organic layer was washed with brine and an aqueous saturated sodium bicarbonate solution, dried over anhydrous magnesium sulfate and then evaporated. The resulting residue was subjected to silica gel column chromatography to give 1.95 g of the title compound as a yellow oil.

¹H-NMR (CDCl₃, 400 MHz) δ; 1.26(s,12H), 1.48(s,4H), 3.46(s,3H), 4.66(d, J=14 Hz, 2H), 5.04(d, J=14 Hz, 2H), 5.45(s,1H), 7.02(s,2H), 7.02(s,2H).

(C) 3-Hydroxymethoxy-2-methoxymethoxymethyl-5,6,7,8-tetrahydro-5,5,8,8-tetramethylnaphthalene A 1.0 M solution (4.53 ml) of diisobutyl aluminum in hexane was added dropwise to 20 ml solution of 657 mg 2,3-(methoxy-methylenedimethyloxy)-5,6,7,8-tetrahydro-5,5,8,8-tetramethylnaphthalene in dichloromethane at −78° C. under stirring. The temperature was raised to room temperature over 1 hour and the mixture was further stirred for 1 hour at the same temperature. The reaction mixture was poured into 30 ml of 2 N aqueous sodium hydroxide and then extracted with ethyl acetate. The organic layer was washed with brine, dried over anhydrous magnesium sulfate and then evaporated. The resulting residue was subjected to silica gel column chromatography to give 491 mg of the title compound as a yellow oil.

¹H-NMR (CDCl₃, 400 MHz) δ; 1.28(s,12H), 1.64(s4H), 3.42(s,3H), 4.65(d,J=6.4 Hz,2H), 4.67(s,2H), 4.72(s,2H), 7.26(s,1H), 7.33(s,1H).

(D) 3-methoxymethyl-2-methoxymethoxymethyl-5,6,7,8-tetrahydro-5,5,8,8-tetramethylnaphthalene 2 ml solution of 491 mg 3-hydroxymethyl-2-methoxymethoxymethyl-5,6,7,8-tetrahydro-5,5,8,8-tetramethyl10naphthalene in dimethylformamide was added to 8 ml suspension of 87 mg sodium hydride in dimethylformamide at 0° C. under stirring. The reaction mixture was stirred at room temperature for 30 minutes, then 0.261 ml methyl iodide was added thereto at 0° C., and the mixture was stirred at room temperature for additional 3 hours. An aqueous saturated ammonium chloride solution was added to the reaction mixture followed by extracting with ethyl acetate. The organic layer was washed with brine and dried over anhydrous magnesium sulfate. Then, the residue obtained under reduced pressure was subjected to silica gel column chromatography to give 294 mg of the title compound as a yellow oil.

¹H-NMR (CDCl₃, 400 MHz) δ; 1.28(s,12H), 1.66(s,4H), 3.00(s,3H), 3.04(s,4H), 4.48(d,J=6.8 Hz,2H), 4.62(s,2H), 4.71(s,2H), 7.29(s,1H), 7.30(s,1H).

(E) 2-hydroxymethyl-3-methoxymethyl-5,6,7,8-tetrahydro-5,5,8,8-tetramethylnaphthalene 1.0 ml of 10% aqueous hydrogen chloride was added at room temperature to 5 ml solution of 294 mg 3-methoxymethyl-2-methoxymethoxymethyl-5,6,7,8-tetrahydro-5,5,8,8-tetramethylnaphthalene in methanol. After the mixture was heated under reflux for 1 hour, methanol was distilled off. Ethyl acetate was added to the residue, and the resulting mixture was washed with brine. The organic layer was dried over anhydrous magnesium sulfate, and then the residue obtained under reduced pressure was subjected to silica gel column chromatography to give 290 mg of the title compound as a yellow oil.

¹H-NMR (CDCl₃, 400 MHz) δ; 1.28(s,12H), 1.68(s,4H), 3.44(s,3H), 4.52(s,2H), 4.60(s,2H), 7.23(s,1H), 7.31(s,1H).

(F) 3-methoxymethyl-5,6,7,8-tetrahydro-5,5,8,8-tetramethylnaphthalene-2-carbaldehyde 0.321 ml dimethyl sulfoxide was added to 5 ml solution of 0.198 ml oxazalyl chloride in dichloromethane at −78° C., and the mixture was stirred at the same temperature for 5 minutes. 2 ml solution of 290 mg 2-hydroxymethyl-3-methoxymethyl-5,6,7,8-tetrahydro-5,5,8,8-tetramethylnaphthalene in dichloromethane was added to the mixture at −78° C., and the mixture was further stirred at the same temperature for 40 minutes. After 0.946 ml triethylamine was added to the reaction mixture at −78° C., the temperature was raised to room temperature over 45 minutes. After water was added thereto, the reaction solution was extracted with ethyl acetate. The organic layer was washed with brine and dried over anhydrous magnesium sulfate. Then, the residue obtained under reduced pressure was subjected to silica gel column chromatography to give 190 mg of the title compound as a yellow oil.

¹H-NMR (CDCl₃, 400 MHz) δ; 1.32(s,12H), 1.72(s,4H), 3.40(s,3H), 3.48(s,3H), 4.47(s,2H), 4.81(s,2H), 7.50(s,1H), 7.80(s,1H).

(G) methyl 4-{4-[2-(3-methoxymethyl-5,6,7,8-tetrahydro-5,5,8,8-tetramethylnaphthalenyl)]-4-oxo-1-butanoyl}benzoate 156 mg of methyl 4-acryloylbenzoate (WO97/34869), 101 mg of 3-benzyl-5-(2-hydroxyethyl)thiazolium chloride and 0.315 ml triethylamine were added at room temperature to 6 ml solution of 190 mg 3-methoxymethyl-5,6,7,8-tetrahydro-5,5,8,8-tetramethylnaphthalene-2-carbaldehyde in dimethylformamide. The mixture was heated at 80° C. for 1 hour under stirring followed by adding water thereto and extracting with ethyl acetate. The organic layer was washed with brine and dried over anhydrous magnesium sulfate. Then, the residue obtained under reduced pressure was subjected to silica gel column chromatography to give 91 mg of the title compound as a yellow oil.

¹H-NMR (CDCl₃, 400 MHz) δ; 1.30(s,6H), 1.34(s,6H), 1.72(s,4H), 3.40–3.45(m,7H), 3.94(s,3H), 4.70(s,2H), 7.55(s,1H), 7.83(s,1H), 8.00(d,J=8.4 Hz,2H), 8.15(d, J=8.4 Hz, 2H).

(H) methyl 4-{2-[5-(3-methoxymethyl-5,6,7,8-tetrahydro-5,5,8,8-tetramethylnaphthalene-2-yl)pyrrolyl]}benzoate 183 mg of ammonium acetate was added at room temperature to 6 ml solution of 107 mg methyl 4-{4-[2-(3-methoxymethyl-5,6,7,8-tetrahydro-5,5,8,8-tetramethylnaphthalenyl)]-4-oxo-1-butanoyl}benzoate in methanol. The mixture was heated under reflux for 8 hours. After methanol was distilled off, water was added thereto followed by the extraction with ethyl acetate. The organic layer was washed with brine and dried over anhydrous magnesium sulfate. Then, the residue obtained under reduced pressure was purified by silica gel column chromatography to give 46 mg of the title compound as a yellow solid.

¹H-NMR (CDCl₃, 400 MHz) δ; 1.32(s,12H), 1.72(s,4H), 3.54(s,3H), 3.92(s,3H), 4.50(s,2H), 6.53(dd,J=2.4,3.6 Hz,1H), 6.75(dd,J=3.6, 2.4 Hz,1H), 7.27(s,1H), 7.54(d,J= 8.4 Hz,2H), 7.57(s,1H), 8.03(d,J=8.4 Hz,2H).

(I) 4-{2-[5-(3-methoxymethyl-5,6,7,8-tetrahydro-5,5,8,8-tetramethylnaphthalene-2-yl)pyrrolyl]}benzoic acid 0.5 ml of 5 N NaOH was added at room temperature to 4 ml solution of 46 mg methyl 4-{2-[5-(3-methoxymethyl-5,6,7,8-tetrahydro-5,5,8,8-tetramethylnaphthalene-2-yl)pyrrolyl]}benzoate in methanol. After the mixture was heated under reflux for 30 minutes, 10 ml water and 1 ml of 10% aqueous HCl were added thereto. The resulting crystals were filtered, washed with water and hexane, and then dried to give 35 mg of the title compound.

¹H-NMR (DMSO-d₆, 400 MHz) δ; 1.24(s,6H), 1.28(s, 6H), 1.68(s,4H), 3.30(s,3H), 4.20(s,2H), 6.32–6.35(m,1H), 6.75–6.77(m,1H), 7.39(s,1H), 7.41(s,1H), 7.76(d,J=8.4 Hz,2H), 7.90(d,J=8.4 Hz,2H).

Synthetic Example 198

4-{2-[5-(5,6,7,8-Tetrahydro-3,5,5,8,8-pentamethylnaphthalene-2-yl)pyrrolyl]}benzoic acid 3,5,5,8,8-Pentamethyl-5,6,7,8-tetrahydronaphthalene was synthesized according to the synthetic method described above by use of 3,5,5,8,8-pentamethyl-5,6,7,8-tetrahydronaphthalene-2-carbaldehyde as an intermediate obtained by vilsmeier reaction (JP-A 9-71566; Referential Example 3).

¹H-NMR (DMSO-d₆, 400 MHz) δ; 1.24(s,6H), 1.26(s, 6H), 1.63(s,4H), 2.30(s,3H), 6.20–6.22(m,1H), 6.72–6.74 (m,1H), 7.19(s,1H), 7.29(s,1H), 7.78(d,J=8.0 Hz,2H), 7.89 (d,J=8 Hz,2H).

In the utilities of the present invention described above, preferably the disease is nephritis, idiopathic thrombocytopenic purpura or autoimmune anemia, the nephritis is glomerulonephritis or lupus nephritis, the disease is systematic erythematosus, nephritis, idiopathic thrombocytopenic purpura or autoimmune anemia, the disease is glomerulonephritis or lupus nephritis, and the disease is lupus nephritis.

The retinoic acid receptor (RAR) agonist used for the utilities of the present invention is preferably a retinoic acid receptor subtype α (RAR^α) agonist.

What is claimed is:

1. A method of treating nephritis or lupus nephritis comprising administering to a subject in need of same an effective a compound of the following formula or a pharmacologically acceptable salt thereof or a hydrate of the salt:

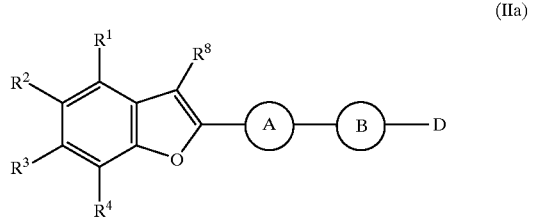

(IIa)

where $R^1$, $R^2$, $R^3$, $R^4$ and $R^8$ each represents hydrogen, halogeno, optionally substituted lower alkyl, optionally substituted cycloalkyl, optionally substituted aryl, optionally substituted heteroaryl, optionally substituted lower alkoxy, optionally substituted aryloxy, optionally substituted heteroaryloxy, optionally substituted cycloalkylalkyl, optionally substituted arylalkyl, optionally substituted heteroarylalkyl, optionally substituted cycloalkyloxy, optionally substituted cycloalkylalkyloxy, optionally substituted arylalkyloxy, optionally substituted heteroarylalkyloxy, optionally substituted alkenyl or optionally substituted alkynyl, or alternatively two of $R^1$, $R^2$, $R^3$, $R^4$ and $R^8$ adjacent to each other together with the carbon atoms to which they are bonded respectively may form a ring which may contain a heteroatom or be substituted; A represents an optionally substituted pyrrole ring, B represents an optionally substituted aromatic hydrocarbon ring or an optionally substituted unsaturated heterocycle; and D represents an optionally protected carboxyl.

2. The method as claimed in claim 1, wherein B represents an optionally substituted phenyl group or pyridyl group.

3. The method of claim 1, wherein the compound is selected from the group consisting of 4-{2-[5-(4,7-dimethylbenzofuran-2-yl)pyrrolyl]}benzoic acid; 4-{2-[5-(7-fluoro-4-trifluoromethylbenzofuran-2-yl)pyrrolyl]}benzoic acid; 4-{2-[5-(3-fluoro-4,7-dimethylbenzofuran-2-yl)pyrrolyl]}benzoic acid; and 4-{2-[5-(7-ethyl-4-methylbenzofuran-2-yl)pyrrolyl]}benzoic acid.

4. The method as claimed in claim 1, wherein nephritis is treated.

5. The method as claimed in claim 1, wherein lupus nephritis is treated.

6. A method of claim 1, wherein the compound is

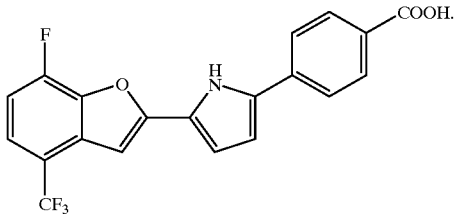

7. A method of treating nephritis or lupus nephritis comprising administering to a subject in need of same an effective amount of a compound selected from the group consisting of 4-{2-[5-(4,7-dimethylbenzofuran-2-yl) pyrrolyl]}benzoic acid; 4-{2-[5-(7-fluoro-4-trifluoromethylbenzofuran-2-yl)pyrrolyl]}benzoic acid; 4-{2-[5-(3-fluoro-4,7-dimethylbenzofuran-2-yl)pyrrolyl]}benzoic acid; and 4-{2-[5-(7-ethyl-4-methylbenzofuran-2-yl)pyrrolyl]}benzoic acid.

* * * * *